United States Patent
Stockel et al.

(10) Patent No.: US 10,995,350 B2
(45) Date of Patent: May 4, 2021

(54) PURINE ALKALOID-PRODUCING MICROORGANISMS AND METHODS OF MAKING AND USING THE SAME

(71) Applicant: MOgene Green Chemicals LLC, St. Louis, MO (US)

(72) Inventors: Jana Stockel, St. Louis, MO (US); Abhay Kumar Singh, Chesterfield, MO (US); Himadri Pakrasi, St. Louis, MO (US); Ganesh Murthy Kishore, Creve Coeur, MO (US)

(73) Assignee: MOgene Green Chemicals LLC, St. Louis, MO (US)

( * ) Notice: Subject to any disclaimer, the term of this patent is extended or adjusted under 35 U.S.C. 154(b) by 0 days.

(21) Appl. No.: 15/466,534

(22) Filed: Mar. 22, 2017

(65) Prior Publication Data

US 2017/0275660 A1    Sep. 28, 2017

Related U.S. Application Data

(60) Provisional application No. 62/312,298, filed on Mar. 23, 2016.

(51) Int. Cl.
| | |
|---|---|
| *C12N 9/10* | (2006.01) |
| *C12N 9/14* | (2006.01) |
| *C12P 17/18* | (2006.01) |
| *C12N 15/52* | (2006.01) |

(52) U.S. Cl.
CPC .......... *C12P 17/182* (2013.01); *C12N 9/1007* (2013.01); *C12N 9/1085* (2013.01); *C12N 9/14* (2013.01); *C12N 15/52* (2013.01); *C12Y 201/0116* (2013.01); *C12Y 201/01158* (2013.01); *C12Y 201/01159* (2013.01); *C12Y 205/01006* (2013.01); *C12Y 303/01001* (2013.01)

(58) Field of Classification Search
CPC .................. C12N 9/10; C12N 15/8243; C12Y 201/01158; C12Y 201/01159; C12Y 303/01001; C12P 17/12; C12P 17/182
USPC ........... 435/468, 320.1, 252.2, 191, 193, 118
See application file for complete search history.

(56) References Cited

U.S. PATENT DOCUMENTS

| | | | |
|---|---|---|---|
| 4,683,195 | A | 7/1987 | Mullis et al. |
| 4,683,202 | A | 7/1987 | Mullis |
| 4,800,159 | A | 1/1989 | Mullis et al. |
| 4,965,188 | A | 10/1990 | Mullis et al. |
| 2017/0275660 | A1 | 9/2017 | Stockel et al. |

OTHER PUBLICATIONS

Ashihara et al Trend Plant Sci 2001, 6(9) pp. 407-413.*
Peifer et al. Microb Cell fact 2012, 11:138, pp. 1-14.*
Devos et al., (Proteins: Structure, Function and Genetics, 2000, vol. 41: 98-107.*
Witkowski et al., (Biochemistry 38:11643-11650, 1999.*
Kisselev L., (Structure, 2002, vol. 10: 8-9.*
Whisstock et al., (Quarterly Reviews of Biophysics 2003, vol. 36 (3): 307-340.*
Markham et al. Cell mol life Sci,2009, 66, pp. 636-648.*
Chenna et al., "Multiple sequence alignment with the Clustal series of programs," *Nucleic Acids Res.*, 31(13):3497-3500, Jul. 1, 2003.
Dayhoff et al., "A model of evolutionary change in proteins," in Atlas of Protein Sequence and Structure, M.O. Dayhoff, Ed., pp. 345-352, National Biomedical Research Foundation, Washington, DC, 1978.
Dueber et al., "Synthetic protein scaffolds provide modular control over metabolic flux," *Nature Biotechnol.* 27(8):753-759, Aug. 2009.
Jin et al., "Metabolic Engineering of *Saccharomyces cerevisiae* for Caffeine and Theobromine Production," *Plos One* 9(8):e105368, Aug. 2014, 11 pages.
Lambert et al., "Stir bar sorptive extraction based on restricted access material for the direct extraction of caffeine and metabolites in biological fluids," *J. Chromatogr A.* 1075(1-2):43-49, May 1, 2005.
Li et al., "Modularly assembled designer TAL effector nucleases for targeted gene knockout and gene replacement in eukaryotes," *Nucleic Acids Res.* 39(14):6315-6325, Aug. 2011.
Mali et al., "Cas9 as a versatile tool for engineering biology," *Nature Methods* 10(10):957-963, Oct. 2013.
Mizuno et al., "Isolation of a new dual-functional caffeine synthases gene encoding an enzyme for the conversion of 7-methylxanthosine to caffeine from coffee (*Coffea arabica* L.)," *FEBS Lett.* 534(1-3):75-81, Jan. 16, 2003.
NCBI Accession No. AB031280, "*Camellia sinensis* TCS1 mRNA for caffeine synthase, complete cds," Aug. 31, 2000, 2 pages.
NCBI Accession No. AB048793, "*Coffea arabica* CaXMT1 mRNA for xanthosine methyltransferase, complete cds," Dec. 6, 2005, 2 pages.
NCBI Accession No. AB048794, "*Coffea arabica* CaMXMT1 mRNA for 7-methylxanthine N-methyltransferase, complete cds," Dec. 6, 2005, 2 pages.
NCBI Accession No. AB086414, "*Coffea arabica* CCS1 mRNA for caffeine synthase 1, complete cds," Sep. 16, 2006, 2 pages.

(Continued)

*Primary Examiner* — Robert B Mondesi
*Assistant Examiner* — Mohammad Y Meah
(74) *Attorney, Agent, or Firm* — Fish & Richardson P.C.

(57) ABSTRACT

Provided herein are microorganisms that include one or more heterologous nucleic acid selected from the group of a sequence encoding a 7-methylxanthosine synthase, a sequence encoding a theobromine synthase; and a sequence encoding a caffeine synthase, where the microorganism is capable of producing one or more purine alkaloid in a culture medium, when the microorganism is cultured under conditions sufficient to produce the one or more purine alkaloid. Also provided compositions and kits that include at least one of these microorganisms, and methods of producing one or more purine alkaloid that include culturing one of these microorganisms under conditions sufficient to produce the one or more purine alkaloid.

13 Claims, 6 Drawing Sheets

Specification includes a Sequence Listing.

(56) References Cited

OTHER PUBLICATIONS

Nehlig et al., "Caffeine and the central nervous system: mechanisms of action, biochemical, metabolic and psychostimulant effects," *Brain Res Rev.* 17(2):139-170, May-Aug. 1992.

Uefuji et al., "Molecular Cloning and Functional Characterization of Three Distinct N-Methyltransferases Involved in the Caffeine Biosynthetic Pathway in Coffee Plants," *Plant Physiol.* 132(1):372-380, May 2003.

Wright et al., "High-frequency homologous recombination in plants mediated by zinc-finger nucleases," *Plant J.* 44:693-705, 2005.

Zakataeva et al., "Wild-type and feedback-resistant phosphoribosyl pyrophosphate synthetases from *Bacillus amyloliquefaciens*: purification, characterization, and application to increase purine nucleoside production," *Appl. Microbiol. Biotechnol.* 93(5):2023-2033, Mar. 2012.

Zhou et al., "Binding of purine nucleotides to two regulatory sites results in synergistic feedback inhibition of glutamine 5-phosphoribosylpyrophosphate amidotransferase," *J. Biol. Chem.* 269(9):6784-6789, Mar. 4, 1994.

\* cited by examiner

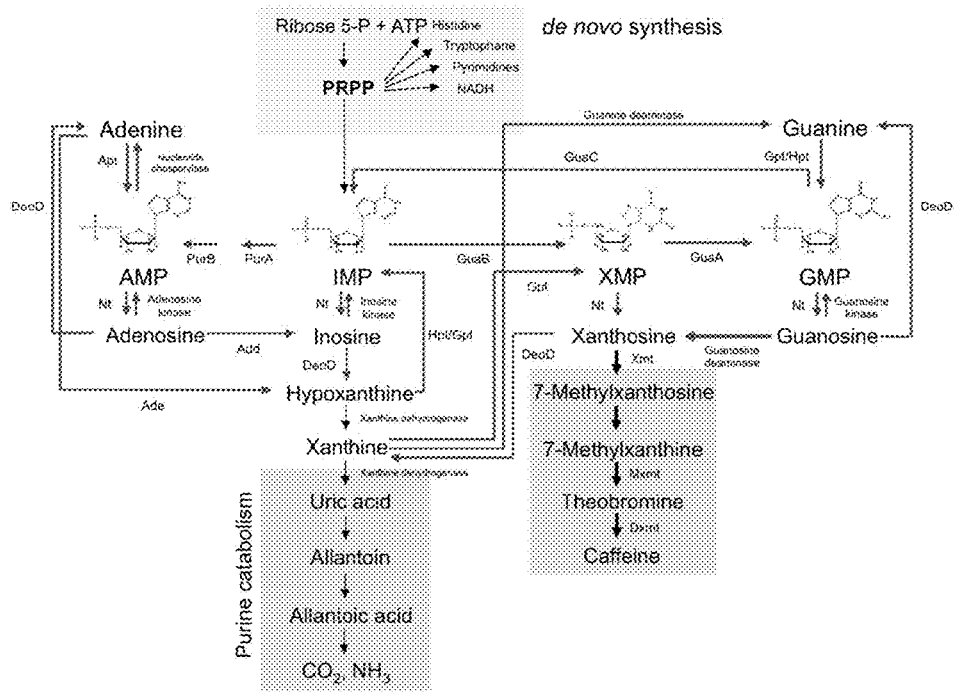

FIG. 1

| Enzyme | Origin | Specific activity | Km | pH | Reference |
|---|---|---|---|---|---|
| CaXMT 7-Methylxanthosine synthase | *Coffea arabica* | | Xanthosine: 78 μM S-adenosylmethionine: 13 μM | | Uefuji et al., 2003 |
| CaMXMT Theobromine synthase | *Coffea arabica* AB048794 | | 7-Methylxanthine: 251 μM S-adenosylmethionine: 14 μM | | |
| CCS1 Caffeine synthase | *Coffea arabica* AB086414 | | Theobromine: 157 μM | | Mizuno et al., 2003 |
| TCS Caffeine synthase | *Camellia sinensis* | 5.7 nkat mg⁻¹ protein 0.7 nkat mg⁻¹ protein 2.7 nkat mg⁻¹ protein * ammonium sulfate fractionation and hydroxyapatite, anion exchange, adenosine-agarose and gel filtration chromatography | Paraxanthine: 24 μM Theobromine: 186 μM 7-Methylxanthine: 344 μM S-adenosylmethionine: 21 μM | 8.5 | Kato et al., 1999 |

FIG. 2

PURINE ALKALOID-PRODUCING MICROORGANISMS AND METHODS OF MAKING AND USING THE SAME

CROSS-REFERENCE TO RELATED APPLICATIONS

This application claims priority to U.S. Provisional Patent Application Ser. No. 62/312,298, filed Mar. 23, 2016, which is incorporated by reference in its entirety.

TECHNICAL FIELD

This disclosure generally relates to biotechnology methods for producing one or more purine alkaloids and compositions including one or more of these produced purine alkaloids.

BACKGROUND

Purine alkaloids are secondary metabolites produced in certain plants from purine nucleotides. These alkaloids are known to be present in more than 100 species across 13 orders of plant kingdom (Ashihara and Crozier, Adv. Bot. Res. 30, 118-205, 1999). Caffeine is the well-known member of the purine alkaloids. Other purine alkaloids are also pharmaceutically important and include, e.g., xanthine, methylxanthine, theobromine, and theophylline.

Caffeine is a central nervous system stimulant of the methylxanthine class (Nehlig et al., Brain Res. Brain Res. Rev. 17(2):139-170, 1992), and is the world's most widely consumed psychoactive drug. Caffeine reversibly blocks the action of adenosine on its receptor and consequently prevents the onset of drowsiness induced by adenosine. Caffeine also stimulates certain portions of the autonomic nervous system. The most well-known natural source of caffeine is the coffee bean. Caffeine is also chemically synthesized (known as synthetic caffeine) and used for human consumption. Beverages containing caffeine are ingested to relieve or prevent drowsiness and to improve performance. To make these beverages, caffeine is extracted by steeping the plant product in water, a process called infusion, as well as other methods that utilize organic solvents such as dichloromethane. Caffeine-containing beverages, such as coffee, tea, and colas, are very popular; in 2005, 90% of North American adults consumed caffeine daily (Lovett, New Scientist website, www.newscientist.com, Sep. 21, 2005). Energy drinks containing higher amount of caffeine are also very popular in certain market segments.

SUMMARY

Applicants discovered that specific genetic modifications to microorganisms allow the resulting microorganisms to produce one or more purine alkaloids. Based on this discovery provided herein are microorganisms that can be used to produce one or more purine alkaloid, and methods of producing one or more purine alkaloid using one or more of these microorganisms.

Provided herein are microorganisms including one or more heterologous nucleic acid selected from the group of: a sequence encoding a 7-methylxanthosine synthase; a sequence encoding a theobromine synthase; and a sequence encoding a caffeine synthase, where the microorganism is capable of producing one or more purine alkaloid in a culture medium, when the microorganism is cultured under conditions sufficient to produce the one or more purine alkaloid. In some embodiments of these microorganisms, the culture medium includes one or more of the following: a carbon source; a nitrogen source (e.g., a nitrogen source selected from the group of nitrate, ammonium, and urea); a one-carbon donor (e.g., a one-carbon donor selected from the group of S-adenosyl-methionine, glycine betaine, methionine, and 2-hydroxy-4-(methylthio) butanoate); and a nucleobase (e.g., a nucleobase selected from the group of adenine, guanine, xanthine, and hypoxanthine), a nucleoside (e.g., a modified nucleoside, e.g., inosine or xanthosine; or a nucleoside selected from the group of adenosine, deoxyadenosine, guanosine, inosine, and deoxyguanosine), or a nucleotide (e.g., a nucleotide selected from the group of adenine triphosphate (ATP), inosine monophosphate, guanosine 5'-triphosphate (GTP), and xanthosine monophosphate). In some embodiments of any of the microorganisms described herein, the carbon source is selected from the group of: $CO_2$, acetate, glycerol, a sugar, a hydrocarbon (e.g., methane), formic acid, or an alcohol (e.g., methanol). In some embodiments of any of the microorganisms described herein, the nucleobase, the nucleoside, or the nucleotide is a nucleobase, a nucleoside, or a nucleotide present in plant nucleic acid hydrolysate or spent yeast hydrolysate. In some embodiments of any of the microorganisms described herein, the one or more purine alkaloid is selected from the group of: theobromine, paraxanthine, caffeine, theophylline, and theacrine.

In some embodiments of any of the microorganisms described herein, the microorganism is capable of secreting or releasing the one or more purine alkaloid into the culture medium, when the microorganism is cultured under conditions sufficient to produce the one or more purine alkaloid. In some embodiments of any of the microorganisms described herein, the microorganism is capable of producing the one or more purine alkaloid in the cytosol, when the microorganism is cultured under conditions sufficient to produce the one or more purine alkaloid. In some embodiments of any of the microorganisms described herein, the microorganism is a prokaryote (e.g., a prokaryote selected from the group of *E. coli, Corynebacterium ammoniagenes, Bacillus subtilis, Methylomicrobium buryatense, Synechocystis* 6803, and *Rhodopseudomonas palustris*). In some embodiments of any of the microorganisms described herein, the microorganism is a eukaryote (e.g., a yeast species, e.g., a yeast species selected from the group of *Saccharomyces cerevisiae, Pichia pastoris, Ashbya gossypii*, and *Pichia kudriavzevii*).

In some embodiments of any of the microorganisms described herein, the microorganism further includes one or more heterologous nucleic acid selected from the group consisting of: (i) a sequence encoding a S-adenosyl-methionine synthetase; (ii) a sequence encoding a S-adenosyl-L-homocysteine hydrolase; (iii) a sequence encoding a methionine synthase; (iv) a sequence encoding an adenosine deaminase; (v) a sequence encoding an adenine phosphoribosyltransferase; (vi) a sequence encoding a methylenetetrahydrofolate (THF) reductase; (vii) a sequence encoding a glycine decarboxylase; (viii) a sequence encoding a serine hydroxymethyltransferase; (ix) a sequence encoding a formate-tetrahydrofolate ligase; (x) a sequence encoding a dihydrofolate reductase; (xi) a sequence encoding a GTP cyclohydrolase; (xii) a sequence encoding a aminodeoxychorismate synthase; (xiii) a sequence encoding a dihydrofolate synthase; (xiv) a sequence encoding a transporter of one or both of methionine and 2-hydroxy-4-methylthiobutanoic acid; (xv) a sequence encoding a guanosine deaminase; (xvi) a sequence encoding a xanthine, adenine, or guanine phosphoribosyl transferase; (xvii) a sequence encoding a GTP cyclohydrolase; (xviii) a sequence encoding an aminodeoxychorismate synthase; (xix) a sequence encoding a dihydrofolate synthase; (xx) a sequence encoding 5' nucleotidase ushA; (xxi) a sequence encoding 5-phospho-α-D-ribosyl-1-pyrophosphate synthetase; (xxii) a sequence encoding a 5-phospho-α-D-ribosyl-1-pyrophosphate amidotransferase; and (xxiii) a sequence encoding an inosine 5-monophosphate dehydrogenase. In some embodiments of any of the microorganisms described herein, the S-adenosyl-methionine synthetase is a feed-back resistant enzyme (e.g., a cobalamin-independent enzyme and utilizes methyl-THF as methyl donor). In some embodiments of any of the microorganisms described herein, the methionine synthase is a betaine-homocysteine S-methyltransferase and utilizes glycine betaine as methyl donor. In some embodiments of any of the microorganisms described herein, the methylene-THF reductase is a feedback-resistant enzyme. In some embodiments of any of the microorganisms described herein, the dihydrofolate reductase is a feedback-resistant enzyme. In some embodiments of any of the microorganisms described herein, the 5-phospho-α-D-ribosyl-1-pyrophosphate synthetase is a feedback resistant enzyme. In some embodiments of any of the microorganisms described herein, the 5-phospho-α-D-ribosyl-1-pyrophosphate amidotransferase is a feedback-resistant enzyme.

In some embodiments of any of the microorganisms described herein, the microorganism is capable of producing methyl-THF when the microorganism is cultured (i) in a culture medium including a substrate that is toxic if unmethylated, and (ii) under conditions sufficient to produce methyl-THF. In some embodiments of any of the microorganisms described herein, the microorganism is capable of producing methylene-THF when cultured (i) in a culture medium including glycine and folic acid, and (ii) under conditions sufficient to produce methylene-THF. In some embodiments of any of the microorganisms described herein, the microorganism is capable of producing one-carbon THF intermediates when cultured (i) in a culture medium including methanol, and (ii) under conditions sufficient to produce one-carbon THF intermediates. In some embodiments of any of the microorganisms described herein, the microorganism is capable of overproducing folate when cultured in a culture medium including one or more of: methotrexate, trimethoprim, pemetrexed, proguanil, and primethamine. In some embodiments of any of the microorganisms described herein, the microorganism includes one or more of: a sequence encoding a modified GMP synthetase, a sequence encoding a modified adenylosuccinate synthetase, a sequence encoding a modified guanosine kinase, a sequence encoding a modified purine repressor, a sequence encoding a modified purine nucleoside phosphorylase, a sequence encoding a modified xanthine dehydrogenase, and a sequences encoding a modified glucose-6-. In some embodiments of any of the microorganisms described herein, one or more of the modified GMP synthetase, the modified adenylosuccinate synthetase, the modified guanosine kinase, the modified purine repressor, the modified purine nucleoside phosphorylase, the modified xanthine dehydrogenase, and the modified glucose-6-phosphate isomerase have decreased activity as compared to the corresponding wild type enzyme. In some embodiments of any of the microorganisms described herein, the microorganism does not include one or more of: a sequence encoding an active GMP synthetase, a sequence encoding an active adenylosuccinate synthetase, a sequence encoding an active guanosine kinase, a sequence encoding an active purine repressor, a sequence encoding an active purine nucleoside phosphorylase, a sequence encoding an active xanthine dehydrogenase, and a sequence encoding an active glucose-6-phosphate isomerase. In some embodiments of any of the microorganisms described herein, the microorganism has an increased rate of conversion of 5-phospho-α-D-ribosyl-1-pyrophosphate to xanthosine 5-monophosphate, through an intermediate of inosine 5-monophosphate, as compared to the rate of the conversion in a wildtype cell. In some embodiments of any of the microorganisms described herein, two or more of the 7-methylxanthosine synthase, the theobromine synthase, and the caffeine synthase are co-located in the microorganism. In some embodiments of any of the microorganisms described herein, two or more of the following enzymes are co-localized in the microorganism: (i) the S-adenosyl-methionine synthetase; (ii) the S-adenosyl-L-homocysteine hydrolase; (iii) the methionine synthase; (iv) the adenosine deaminase; (v) the adenine phosphoribosyltransferase; (vi) the methylene-tetrahydrofolate (THF) reductase; (vii) the glycine decarboxylase; (viii) the serine hydroxymethyltransferase; (ix) the formate-tetrahydrofolate ligase; (x) the dihydrofolate reductase; (xi) the GTP cyclohydrolase; (xii) the aminodeoxychorismate synthase; (xiii) the dihydrofolate synthase; (xiv) the transporter of one or both of methionine and 2-hydroxy-4-methylthio-butanoic acid; (xv) the guanosine deaminase; (xvi) the xanthine, adenine, or guanine phosphoribosyl transferase; (xvii) the GTP cyclohydrolase; (xviii) the aminodeoxychorismate synthase; (xix) the dihydrofolate synthase; (xx) the 5' nucleotidase ushA; (xxi) the 5-phospho-α-D-ribosyl-1-pyrophosphate synthetase; (xxii) the 5-phospho-α-D-ribosyl-1-pyrophosphate amidotransferase; and (xxiii) the inosine 5-monophosphate dehydrogenase. In some embodiments of any of the microorganisms described herein, the microorganism has one or both of an increased level of S-adenosyl methionine and an increased rate of recycling of S-adenosyl homocysteine, as compared to a corresponding wildtype microorganism.

Also provided herein are compositions that include any one of the microorganisms described herein. Some embodiments of these compositions further include a storage medium (e.g., a storage medium including one or both of dimethylsulfoxide and glycerol).

Also provided herein are kits that include a vial including any of the compositions described herein. Some embodiments of these kits further include instructions for culturing the microorganism.

Also provided are methods of producing one or more purine alkaloid that include culturing any of the microorganisms described herein in a culture medium under conditions sufficient to produce the one or more purine alkaloid; and harvesting the one or more purine alkaloid. In some embodiments of any of these methods, the one or more purine alkaloid is harvested from the culture medium. In some embodiments of any of the methods described herein, the culturing results in the production of a culture medium including a total concentration of at least 0.2 mg/mL (e.g., at least 0.5 mg/mL, at least 1 mg/mL, or at least 2 mg/mL) of the one or more purine alkaloid. In some embodiments of any of the methods described herein, the one or more purine alkaloid is theobromine, caffeine, theophylline, and theacrine. In some embodiments of any of the methods described herein, the culture medium includes: (i) a one-carbon donor, and (ii) a nucleobase, a nucleoside, or a nucleotide. In some embodiments of any of the methods described herein, the culture medium includes: (i) a carbon source, and (ii) a nitrogen source.

Also provided herein are compositions that include a lysate of any of the microorganisms described herein. Also provided herein are compositions that include a cell-free lysate including proteins produced by any of the microorganisms described herein. Also provided herein are compositions that include any of the cell-free lysates described herein mixed with a lysate of another microorganism. Also provided herein are methods of producing one or more purine alkaloid that include: mixing any of the compositions including a lysate described herein with one or more substrate(s) to generate a mixture; and incubating the mixture under conditions sufficient to produce the one or more purine alkaloid; and harvesting the one or more purine alkaloid. In some embodiments of any of the methods described herein, the incubating results in the production of a mixture comprising a total concentration of least 0.2 mg/mL (e.g., at least 0.5 mg/mL, at least 1 mg/mL, or at least 2 mg/mL) of the one or more purine alkaloid. In some embodiments of any of the methods described herein, the one or more purine alkaloid is theobromine, paraxanthine, caffeine, theophylline, and theacrine. In some embodiments of any of the methods described herein, the one or more substrate(s) comprise(s): (i) a one-carbon donor, and (ii) a nucleobase, a nucleoside, or a nucleotide. In some embodiments of any of the methods described herein, the one or more substrate(s) include(s): (i) a carbon source, and (ii) a nitrogen source. In some embodiments of any of the methods described herein, the one or more substrates is a nucleobase, a nucleoside, or a nucleotide present in a plant nucleic acid hydrolysate or spent yeast hydrolysate.

Some embodiments of these methods further include adding the harvested one or more purine alkaloid to an animal feed or food product (e.g., a beverage).

Unless otherwise defined, all technical and scientific terms used herein have the same meaning as commonly understood by one of ordinary skill in the art to which the methods and compositions of matter belong. Although methods and materials similar or equivalent to those described herein can be used in the practice or testing of the methods and compositions of matter, suitable methods and materials are described below. In addition, the materials, methods, and examples are illustrative only and not intended to be limiting. All publications, patent applications, patents, and other references mentioned herein are incorporated by reference in their entirety.

DESCRIPTION OF DRAWINGS

FIG. 1 is a schematic presentation of the cellular pathways and the engineered pathways involved in the production of caffeine in *E. coli*.

FIG. 2 is a table showing the recombinant enzymes expressed and tested in the *E. coli* strains in Example 1.

DETAILED DESCRIPTION

Figure 3:
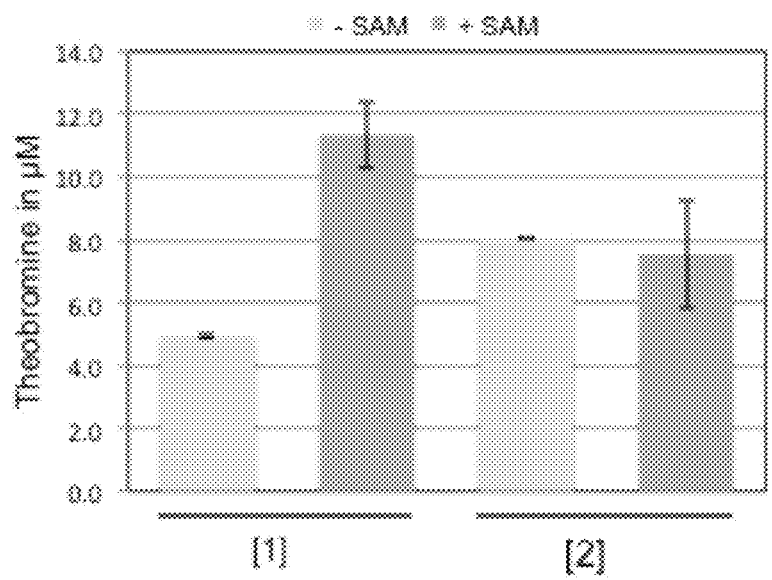
FIG. 3 is a graph showing the production of theobromine using *E. coli* containing construct [1] (expressing *Coffea arabica* 7-methylxanthosine synthase, *Coffea arabica* theobromine synthase, and *Camellia sinensis* caffeine synthase) or *E. coli* containing construct [2] (expressing *Coffea arabica* 7-methylxanthosine synthase, *Coffea arabica* theobromine synthase, and *Coffea arabica* caffeine synthase) following culture in the presence of 500 µM xanthosine and in the presence or absence of 300 µM S-adenosyl-methionine.

Approximately, 90% of caffeine consumed in food/feed are obtained using a chemical based method. This is because cost of extracting caffeine from natural plant sources is very high. However, chemical method is non-sustainable and environmentally unfriendly. Development of a commercial bioprocess using engineered biocatalysts for producing purine alkaloids has not been accomplished due to the complexity of synthesizing such chemicals which involves interactions of multiple primary and secondary metabolic pathways involving several native enzymes as well as non-native enzymes. Provided herein are several different modified (e.g., recombinant) microorganisms (e.g., bacteria and yeast) that exhibit (e.g., increased or optimized) production of one or more purine alkaloid. As discussed herein, these modifications can be accomplished by several methods including mutagenesis (e.g., random or targeted mutagenesis) of one or more endogenous nucleic acids in the microorganism and/or use of chemical mutagens and/or recombinant technology (e.g., introduction of one or more heterologous nucleic acids into the microorganism) and/or a combination of these methods.

More specifically, provided herein are microorganisms that include one or more (e.g., two or three) heterologous nucleic acid selected from the group of: a sequence encoding a 7-methylxanthosine synthase, a sequence encoding a theobromine synthase, and a sequence encoding a caffeine synthase, where the microorganism is capable of producing one or more (e.g., two, three, four, or five) purine alkaloid (e.g., any of the purine alkaloids described herein) in a culture medium, when the microorganism is cultured under conditions sufficient to produce the one or more purine alkaloid. Also provided are compositions that include microbial cell extracts or cell free extracts containing enzymes capable of producing one or more (e.g., two, three, four, or five) purine alkaloid (e.g., any of the purine alkaloids described herein) in a medium and under conditions sufficient to produce the one or more purine alkaloid. Also provided are compositions that include one of the microorganisms provided herein, and kits comprising a vial or container including any of the compositions provided herein. Also provided are methods of producing one or more (e.g., two, three, four, or five) purine alkaloid (e.g., any of the purine alkaloids described herein) that include culturing any of the microorganisms provided herein in a culture medium under conditions sufficient to produce the one or more purine alkaloid, and harvesting the one or more purine alkaloid (e.g., from the microorganism and/or the culture medium).

Non-limiting aspects of the microorganisms, compositions, kits, and methods are described herein. As can be appreciated by those skilled in the art, various aspects described below can be used in any combination.

Purine Alkaloids

The microorganisms provided herein are capable of producing one or more (e.g., two, three, four, or five) purine alkaloid when cultured in a culture medium and under conditions sufficient to produce the one or more purine alkaloid. Non-limiting examples of purine alkaloids that can be produced using any of the microorganisms described herein or in any of the methods described herein include: paraxanthine, methylxanthine, caffeine, theobromine, theophylline, and theacrine. Additional examples of purine alkaloids that can be produced by any of the microorganisms described herein or in any of the methods described herein are known in the art.

Microorganisms

Provided herein are microorganisms that include one or more (e.g., two or three) heterologous nucleic acid selected from the group of: a sequence encoding a 7-methylxanothosine synthase, a sequence encoding a theobromine synthase, and a sequence encoding caffeine synthase, where the microorganism is capable of producing one or more (e.g., two, three, four, or five) purine alkaloid in a culture medium (e.g., any of the exemplary culture media described herein), wherein the microorganism is cultured under conditions sufficient to produce the one or more purine alkaloid (e.g., any of the exemplary culturing conditions described herein). Non-limiting examples of sequences of a 7-methylxanothosine synthase, a theobromine synthase, and a caffeine synthase are listed in Table 1. Non-limiting examples of a sequence encoding a 7-methylxanothosine synthase, a sequence encoding a theobromine synthase, and a sequence encoding caffeine synthase are listed in Table 1. In some examples of any of the microorganisms described herein, one or more (e.g., two or three) of the heterologous sequence encoding a 7-methylxanothosine synthase, the heterologous sequence encoding a theobromine synthase, and the heterologous sequence encoding caffeine synthase can be integrated into the genome of the microorganism (e.g., a chromosome of the microorganism). In other examples of any of the microorganisms described herein, one or more (e.g., two or three) of the heterologous sequence encoding a 7-methylxanothosine synthase, the heterologous sequence encoding a theobromine synthase, and the heterologous sequence encoding a caffeine synthase is not present in the genome of the microorganism (e.g., present on a plasmid or an artificial chromosome, e.g., a yeast artificial chromosome or a bacterial artificial chromosome).

In some examples, the microorganism is a prokaryote. In some examples, the microorganism (e.g., genetically-modified or recombinant microorganism) provided herein can be a bacterial strain (e.g., a strain of any of the genera described herein).

Few exemplary prokaryotic and eukaryotic species are described below. However, it will be appreciated that other species may be suitable. For example, suitable species may be in a genus selected from the group consisting of *Acetobacter, Achromobacter, Acidiphilium, Acinetobacter, Alcaligenes, Bacillus, Bifidobacterium, Brevibacillus, Clostridium, Corynebacterium, Escherichia, Enterococcus, Envina, Klebsiella, Kluyveromyces, Lactobacillus, Leuconostoc, Methanogenium, Micrococcus, Propionibacterium, Pseudomonas, Pyrococcus, Streptococcus, Streptomyces, Trichoderma, Xanthomonas,* and *Zymomonas.* In some embodiments, a microorganism can be of a species selected from the cyanobacteria consisting, but limited to, of *Synechocystis, Synechococcus, Anabaena, Cyanothece, Thermosynechococcus, Rhodopseudomonas.* In some embodiments, suitable species may be in a genus selected from the group consisting of but limited to, *Methylosinus, Methylocystis, Methylocella, Methylocapsa, Methylomonas, Methylobacter, Methylococcus, Methylomicrobium, Methylobacterium extorquens, Methylocaldum, Methylosarcina,* and *Methylothermus.* In some embodiments, the microorganism is selected from the group of *E. coli, Corynebacterium* ammoniagenes, Corynebacterium glutamicum, Synechocystis 6803, Rhodopseudomonas palustris, Bacillus subtilis, and Methylomicrobium buryatense.

In some examples, the microorganism is a eukaryote. In some examples, the microorganism (e.g., genetically-modified or recombinant microorganism) provided herein can be a yeast species. In some embodiments, a microorganism of a genus selected from the group consisting of Ashbya, Aspergillus, Candida, Hansenula, Kanwinskia, Pichia, Saccharomyces, Torulopsis, and Rhodotorula. In some examples, the microorganism can be strain of a Pichia species, e.g., Pichia pastoris, Pichia stipitis, Pichia ohmeri, Pichia caribaea, Pichia kudriavzevii, Pichia guilliermondii, Pichia ciferri, Pichia kluyveri, and Pichia pinus. In some examples, the microorganism is a strain of a Saccharomyces species, e.g., Saccharomyces cerevisiae.

In some embodiments, a microorganism can be a photosynthetic microorganism. For example, the organism can be of a genus selected from the group of Chlamydomonas, Dunaliella, Chlorella, Botryococcus, Nannochloropsis, Physcomitrella, and Ceratodon.

In some examples, the microorganism is capable of secreting or releasing the one or more purine alkaloid into the culture medium, when the microorganism is cultured under conditions sufficient to produce the one or more purine alkaloid. In some examples, the microorganism is capable of producing the one or more purine alkaloid in the cytosol, when the microorganism is cultured under conditions sufficient to produce the one or more purine alkaloid.

In some embodiments, the microorganism (e.g., any of the microorganisms described herein) can further include one or more (e.g., two, three, four, five, six, seven, eight, nine, ten, eleven, twelve, thirteen, fourteen, fifteen, sixteen, seventeen, eighteen, nineteen, twenty, twenty one, twenty two, or twenty three) heterologous nucleic acid selected or an endogenous nucleic acid that has been modified to overcome regulation of gene expression or feedback inhibition from the group of: (i) a sequence encoding a S-adenosyl-methionine synthetase; (ii) a sequence encoding a S-adenosyl-L-homocysteine hydrolase; (iii) a sequence encoding a methionine synthase; (iv) a sequence encoding an adenosine deaminase; (v) a sequence encoding an adenine phosphoribosyltransferase; (vi) a sequence encoding a methylene-tetrahydrofolate (THF) reductase; (vii) a sequence encoding a glycine decarboxylase; (viii) a sequence encoding a serine hydroxymethyltransferase; (ix) a sequence encoding a formate-tetrahydrofolate ligase; (x) a sequence encoding a dihydrofolate reductase; (xi) a sequence encoding a GTP cyclohydrolase; (xii) a sequence encoding a aminodeoxychorismate synthase; (xiii) a sequence encoding a dihydrofolate synthase; (xiv) a sequence encoding a transporter of one or both of methionine and 2-hydroxy-4-methylthio-butanoic acid; (xv) a sequence encoding a guanosine deaminase; (xvi) a sequence encoding a xanthine, adenine, or guanine phosphoribosyl transferase; (xvii) a sequence encoding a GTP cyclohydrolase; (xviii) a sequence encoding an aminodeoxychorismate synthase; (xix) a sequence encoding a dihydrofolate synthase; (xx) a sequence encoding 5' nucleotidase ushA, (xxi) a sequence encoding 5-phospho-α-D-ribosyl-1-pyrophosphate synthetase; (xxii) a sequence encoding a 5-phospho-α-D-ribosyl-1-pyrophosphate amidotransferase; and (xxiii) a sequence encoding an inosine 5-monophosphate dehydrogenase. Non-limiting examples of the sequences of a S-adenosyl-methionine synthetase, a S-adenosyl-L-homocysteine hydrolase, a methionine synthase, an adenosine deaminase, an adenine phosphoribosyltransferase, a methylene-tetrahydrofolate (THF) reductase, a glycine decarboxylase, a serine hydroxymethyltransferase, a formate-tetrahydrofolate ligase, a dihydrofolate reductase, a GTP cyclohydrolase, a aminodeoxychorismate synthase, a dihydrofolate synthase, a transporter of one or both of methionine and 2-hydroxy-4-methylthio-butanoic acid, a guanosine deaminase, a xanthine, adenine, or guanine phosphoribosyl transferase, a GTP cyclohydrolase, an aminodeoxychorismate synthase, a dihydrofolate synthase, and a 5' nucleotidase ushA, a 5-phospho-α-D-ribosyl-1-pyrophosphate synthetase, a 5-phospho-α-D-ribosyl-1-pyrophosphate amidotransferase, and an inosine 5-monophosphate dehydrogenase are listed in Table 1. Any of the microorganisms described herein can also include heterologous nucleic acid encoding one or more additional enzymes. Non-limiting examples of a sequence encoding a S-adenosyl-methionine synthetase, a sequence encoding a S-adenosyl-L-homocysteine hydrolase, a sequence encoding a methionine synthase, a sequence encoding an adenosine deaminase, a sequence encoding an adenine phosphoribosyltransferase, a sequence encoding a methylene-tetrahydrofolate (THF) reductase, a sequence encoding a glycine decarboxylase, a sequence encoding a serine hydroxymethyltransferase, a sequence encoding a formate-tetrahydrofolate ligase, a sequence encoding a dihydrofolate reductase, a sequence encoding a GTP cyclohydrolase, a sequence encoding a aminodeoxychorismate synthase, a sequence encoding a dihydrofolate synthase, a sequence encoding a transporter of one or both of methionine and 2-hydroxy-4-methylthio-butanoic acid, a sequence encoding a guanosine deaminase, a sequence encoding a xanthine, adenine, or guanine phosphoribosyl transferase, a sequence encoding a GTP cyclohydrolase, a sequence encoding an aminodeoxychorismate synthase, a sequence encoding a dihydrofolate synthase; a sequence encoding a 5' nucleotidase ushA, a sequence encoding a 5-phospho-α-D-ribosyl-1-pyrophosphate synthetase, a sequence encoding a 5-phospho-α-D-ribosyl-1-pyrophosphate amidotransferase, and a sequence encoding an inosine 5-monophosphate dehydrogenase are listed in Table 1.

TABLE 1

| Exemplary Protein and Amino Acid Sequences | | |
|---|---|---|
| | Protein Sequence | cDNA Sequence |
| 7-methylxanthosine synthase | Q9AVK0, BAC43755, A4GE69 | AB048793, AB034699, DQ422954 |
| Theobromine synthase | BAG84617, BAG84616, BAG84614, BAB39214, | AB362886, AB362885, AB362883, AB048792 |
| Caffeine synthase | ABP98983, BAE79730, BAB39213, Q9AVL9, BAC43760, BAB12278, BAC43760, BAC43761, BAC75663 | EF526217, AB096699, AB039725, AB039725, AB086414, AB031280, AB086414, AB086415, AB084125 |

TABLE 1-continued

Exemplary Protein and Amino Acid Sequences

| | Protein Sequence | cDNA Sequence |
|---|---|---|
| S-adenosyl-methionine synthetase | ACT44589 (SEQ ID NO: 9), NP_600817 (SEQ ID NO: 10), XP002493112 (SEQ ID NO: 11), EDN60821 (SEQ ID NO: 12), EDN59404 (SEQ ID NO: 13) | GI:253978919, GI:19552815, GI:254572005 |
| S-adenosyl-L-homocysteine hydrolase - EC 3.3.1.1 | NP_599981, XP_002493126, EDN63012 | GI:19551979, GI:254572033, GI:151944753 |
| Methionine synthase - B12 dependent - EC 2.1.1.13 | ACT45501, NP_600367, XP002491046, EDN63067 | GI:58036263, GI:254567872 |
| Adenosine deaminase - EC 3.5.4.4 | ACT43450, EDN62674 | GI:145200, GI:186478035 |
| Adenine phosphoribosyltransferase - EC 2.4.2.7 | ACT42319, NP_600867, XP002493386, EDN64370 | GI:58036263, GI:254572553 |
| Methylene tetrahydrofolate (THF) reductase - EC 1.5.1.20 | ACT45620, NP601375, XP_002492018, XP_002492060, EDN61995 | GI:58036263, GI:254570207, GI:254569900 |
| Glycine decarboxylase - EC 1.4.4.2 | ACT44552, XP002490865, EDN64124 | GI:254567652 |
| Serine hydroxymethyltransferase - EC 2.1.2.1 | ACT44263, NP_600221, XP_002493843 XP_002494026, EDN64872, EDN59605 | GI:58036263, GI:254574547, GI:254573834 |
| Formate tetrahydrofolate ligase - EC 6.3.4.3 | XP_002490773, EDN64699, EDN61791 | GI:254567325 |
| Dihydrofolate reductase - EC 1.5.1.3 | ACT41953, NP_600072, XP_002490391, EDN63566 | GI:19552070, GI:254566561 |
| GTP cyclohydrolase I - EC 3.5.4.16 | ACT43905, NP_601891, XP_002489701, EDN61851 | GI:19553889, GI:254565181 |
| Aminodeoxychorismate synthase - EC2.6.1.85 | ACT43636, NP_600222, EDN62839 | GI:19552220 |
| Dihydrofolate synthase - EC 6.3.2.12 | ACT44062, WP_011265933, XP_002490123, XP_002493601, EDN64500, EDN63570, EDN60037 | GI:254566025, GI:254572984 |
| Methionine transporter | CDQ52432, EFF03198, ADX03612, CEM59709, ALH01924, AGG62683, ADF41782 | GeneID: 944893 , GeneID: 944896 GeneID: 944893 |
| Guanosine deaminase - EC 3.5.4.15 | AED93769, AED93768, EOY11141, | NM_122688.3, NM_001036882.1, XM_007030576.1 |
| Xanthine phosphoribosyltransferase - EC 2.4.2.22 | ACT42132 | ECD_00233 |
| Hypoxanthine phosphoribosyltransferase - EC 2.4.2.8 | ACT42025, NP_601893 | GI:19553891 |
| Adenine phosphoribosyl transferase | BAE76248, NP_415002, NP_600867, AAA96611, AAA62848 | L14434, U16781, |
| Guanine phosphoribosyl transferase | AAA23933, CAA48876, AAB62272, CDO44919, | Y7U_RS01215 |
| GTP cyclohydrolase | KEO49912, KJJ47964, KEI24248 | Y7U_RS06695 |
| Aminodeoxychorismate synthase | ACO58592, KJJ47659, WP_032676916, EDN62839, AAA34840 | Y7U_RS09495 |
| Dihydrofolate synthase | NP_013831, XP_572569, KLA28053, AIG69645 | EDL933_3481 |
| 5' nucleotidase - EC 3.1.3.5 | ACT42330, ACT44413, ACT46029, NP_599274, NP_599580 | GI:19551578 |
| 5-phospho-alpha-D-ribosyl-1-pyrophosphate synthetase - ribose-phosphate pyrophosphokinase - EC 2.7.6.1 | ACT43074, NP_600170, XP_002489640 XP_002490094, XP_002492028, XP_002492271, EDN64551, EDN63814, EDN63075, EDN62482, EDN60100 | GI:19552168, GI:254565059, GI:254565967, GI:254570323 |

TABLE 1-continued

Exemplary Protein and Amino Acid Sequences

| | Protein Sequence | cDNA Sequence |
|---|---|---|
| 5-phospho-alpha-D-ribosyl-1-pyrophosphate aminotransferase - amidophosphoribosyl-transferase - EC 2.4.2.14 | ACT44059, NP_694638, NP_601782, XP_002490088, EDN64240 | GI:23308802, GI:19553780, GI:254565955 |
| Inosine 5-monophosphate dehydrogenase - EC 1.1.1.205 | NP_599839, NP_599840, NP_601875, EDN64340, EDN62491, EDN62488 EDN59330 | GI:19551837, GI:19551838 |
| Inosine-guanosine kinase - EC 2.7.1.73 | AP_001126, EGJ94018, EIC53410, GAB79513 | GI:89107346, GI:332763780, GI:381312613, GI:403196732 |
| Xanthine dehydrogenase - EC 1.17.1.4 | AP_003426, WP_014147920 | GI:89109646 |
| Purine nucleoside phosphorylase - EC 2.4.2.1 | AP_004872 | GI:89111092 |
| Purine represser | APC51920 | |

In some examples, the S-adenosyl-methionine synthetase is a feed-back resistant enzyme. In some embodiments, the methionine synthase is a cobalamin-independent enzyme. In some examples, the methionine synthase is a cobalamin-independent enzyme. In some embodiments, the methionine synthase is a cobalamin-dependent enzyme.

In some examples, the methylene-THF reductase is a feedback-resistant enzyme. In some embodiments, the dihydrofolate reductase is a feedback-resistant enzyme. In some examples, the 5-phospho-α-D-ribosyl-1-pyrophosphate synthetase is a feedback resistant enzyme (Zakataeva et al., *Appl. Microbiol. Biotechnol.* 93:2023-2033, 2012). In some examples, the 5-phospho-α-D-ribosyl-1-pyrophosphate amidotransferase is a feedback-resistant enzyme (Zhou G et al., *J. Biol. Chem.* 1994, 269:6784-6789, 1994).

In some examples of any of the microorganisms described herein, one or more (e.g., two, three, four, five, six, seven, eight, nine, ten, eleven, twelve, thirteen, fourteen, fifteen, sixteen, seventeen, eighteen, nineteen, twenty, twenty-one, twenty-two, or twenty-three) of the heterologous sequence or modified endogenous sequences encoding a S-adenosyl-methionine synthetase, the heterologous sequence encoding a S-adenosyl-L-homocysteine hydrolase, the heterologous sequence encoding a methionine synthase, the heterologous sequence encoding an adenosine deaminase, the heterologous sequence encoding an adenine phosphoribosyltransferase, the heterologous sequence encoding a xanthine, adenine, or guanine phosphoribosyl transferase, the heterologous sequence encoding a 5' nucleotidase, the heterologous sequence encoding a methylene-tetrahydrofolate (THF) reductase, the heterologous sequence encoding a glycine decarboxylase, the heterologous sequence encoding a serine hydroxymethyltransferase, the heterologous sequence encoding a formate-tetrahydrofolate ligase, the heterologous sequence encoding a dihydrofolate reductase, the heterologous sequence encoding a GTP cyclohydrolase, the heterologous sequence encoding a aminodeoxychorismate synthase, the heterologous sequence encoding a dihydrofolate synthase, the heterologous sequence encoding a transporter of one or both of methionine and 2-hydroxy-4-methylthio-butanoic acid, the heterologous sequence encoding a guanosine deaminase, the heterologous sequence encoding a GTP cyclohydrolase, the heterologous sequence encoding an aminodeoxychorismate synthase, the heterologous sequence encoding a dihydrofolate synthase, the heterologous sequence encoding 5-phospho-α-D-ribosyl-1-pyrophosphate synthetase, the heterologous sequence encoding a 5-phospho-α-D-ribosyl-1-pyrophosphate amidotransferase, and the heterologous sequence encoding an inosine 5-monophosphate dehydrogenase can be integrated into the genome of the microorganism (e.g., a chromosome of the microorganism). In other examples of any of the microorganisms described herein, one or more (e.g., two, three, four, five, six, seven, eight, nine, ten, eleven, twelve, thirteen, fourteen, fifteen, sixteen, seventeen, eighteen, nineteen, twenty, twenty-one, twenty-two, or twenty-three) of the heterologous sequence encoding a S-adenosyl-methionine synthetase, the heterologous sequence encoding a S-adenosyl-L-homocysteine hydrolase, the heterologous sequence encoding a methionine synthase, the heterologous sequence encoding an adenosine deaminase, the heterologous sequence encoding an adenine phosphoribosyltransferase, the heterologous sequence encoding a xanthine, adenine, or guanine phosphoribosyl transferase, the heterologous sequence encoding a 5' nucleotidase, the heterologous sequence encoding a xanthine, adenine, or guanine phosphoribosyl transferase, the heterologous sequence encoding a methylene-tetrahydrofolate (THF) reductase, the heterologous sequence encoding a glycine decarboxylase, the heterologous sequence encoding a serine hydroxymethyltransferase, the heterologous sequence encoding a formate-tetrahydrofolate ligase, the heterologous sequence encoding a dihydrofolate reductase, the heterologous sequence encoding a GTP cyclohydrolase, the heterologous sequence encoding a aminodeoxychorismate synthase, the heterologous sequence encoding a dihydrofolate synthase, the heterologous sequence encoding a transporter of one or both of methionine and 2-hydroxy-4-methylthio-butanoic acid, the heterologous sequence encoding a guanosine deaminase, the heterologous sequence encoding a GTP cyclohydrolase, the heterologous sequence encoding an aminodeoxychorismate synthase, the heterologous sequence encoding a dihydrofolate synthase, the heterologous sequence encoding 5' nucleotidase ushA, the heterologous sequence encoding 5-phospho-α-D-ribosyl-1-pyrophosphate synthetase, the heterologous sequence encoding a 5-phospho-α-D-ribosyl-1-pyrophosphate amidotransferase, and the heterologous sequence encoding an inosine 5-monophosphate dehydrogenase is not present in the genome of the microorganism (e.g., present on a plasmid or an artificial chromosome, e.g., a yeast artificial chromosome or a bacterial artificial chromosome).

In some examples, the microorganism is capable of producing methyl-THF when the microorganism is cultured (i) in a culture medium including a substrate that is toxic if unmethylated, and (ii) under conditions sufficient to produce methyl-THF. Non-limiting examples of substrates that are toxic if unmethylated include arsenic, selenium, antimony, and phenol. In some embodiments, the concentration of a substrate that is toxic in the culture medium is about 0.05 mM to about 100 mM, about 90 mM, about 80 mM, about 70 mM, about 60 mM, about 50 mM, about 40 mM, about 30 mM, about 25 mM, about 20 mM, about 15 mM, about 10 mM, about 5 mM, about 2.5 mM, about 1 mM, about 0.5 mM, or about 0.1 mM; about 0.1 mM to about 100 mM, about 90 mM, about 80 mM, about 70 mM, about 60 mM, about 50 mM, about 40 mM, about 30 mM, about 25 mM, about 20 mM, about 15 mM, about 10 mM, about 5 mM, about 2.5 mM, about 1 mM, or about 0.5 mM; about 0.5 mM to about 100 mM, about 90 mM, about 80 mM, about 70 mM, about 60 mM, about 50 mM, about 40 mM, about 30 mM, about 25 mM, about 20 mM, about 15 mM, about 10 mM, about 5 mM, about 2.5 mM, or about 1 mM; about 1 mM to about 100 mM, about 90 mM, about 80 mM, about 70 mM, about 60 mM, about 50 mM, about 40 mM, about 30 mM, about 25 mM, about 20 mM, about 15 mM, about 10 mM, about 5 mM, or about 2.5 mM; about 2.5 mM to about 100 mM, about 90 mM, about 80 mM, about 70 mM, about 60 mM, about 50 mM, about 40 mM, about 30 mM, about 25 mM, about 20 mM, about 15 mM, about 10 mM, or about 5 mM; about 5 mM to about 100 mM, about 90 mM, about 80 mM, about 70 mM, about 60 mM, about 50 mM, about 40 mM, about 30 mM, about 25 mM, about 20 mM, about 15 mM, or about 10 mM; about 10 mM to about 100 mM, about 90 mM, about 80 mM, about 70 mM, about 60 mM, about 50 mM, about 40 mM, about 30 mM, about 25 mM, about 20 mM, or about 15 mM; about 15 mM to about 100 mM, about 90 mM, about 80 mM, about 70 mM, about 60 mM, about 50 mM, about 40 mM, about 30 mM, about 25 mM, or about 20 mM; about 20 mM to about 100 mM, about 90 mM, about 80 mM, about 70 mM, about 60 mM, about 50 mM, about 40 mM, about 30 mM, or about 25 mM; about 25 mM to about 100 mM, about 90 mM, about 80 mM, about 70 mM, about 60 mM, about 50 mM, about 40 mM, or about 30 mM; about 30 mM to about 100 mM, about 90 mM, about 80 mM, about 70 mM, about 60 mM, about 50 mM, or about 40 mM; about 40 mM to about 100 mM, about 90 mM, about 80 mM, about 70 mM, about 60 mM, or about 50 mM; about 50 mM to about 100 mM, about 90 mM, about 80 mM, about 70 mM, or about 60 mM; about 60 mM to about 100 mM, about 90 mM, about 80 mM, or about 70 mM; about 70 mM to about 100 mM, about 90 mM, or about 80 mM; about 80 mM to about 90 mM or about 100 mM; or about 90 mM to about 100 mM.

In some examples, the microorganism is capable of producing methylene-THF when cultured (i) in a culture medium including glycine and folic acid, and (ii) under conditions sufficient to produce methylene-THF. In some embodiments, the concentration of glycine in the culture medium can be about 0.01 mM to about 100 mM, about 90 mM, about 80 mM, about 70 mM, about 60 mM, about 50 mM, about 40 mM, about 30 mM, about 25 mM, about 20 mM, about 15 mM, about 10 mM, about 5 mM, about 2.5 mM, about 1 mM, about 0.5 mM, about 0.1 mM, or about 0.05 mM; about 0.05 mM to about 100 mM, about 90 mM, about 80 mM, about 70 mM, about 60 mM, about 50 mM, about 40 mM, about 30 mM, about 25 mM, about 20 mM, about 15 mM, about 10 mM, about 5 mM, about 2.5 mM, about 1 mM, about 0.5 mM, or about 0.1 mM; about 0.1 mM to about 100 mM, about 90 mM, about 80 mM, about 70 mM, about 60 mM, about 50 mM, about 40 mM, about 30 mM, about 25 mM, about 20 mM, about 15 mM, about 10 mM, about 5 mM, about 2.5 mM, about 1 mM, or about 0.5 mM; about 0.5 mM to about 100 mM, about 90 mM, about 80 mM, about 70 mM, about 60 mM, about 50 mM, about 40 mM, about 30 mM, about 25 mM, about 20 mM, about 15 mM, about 10 mM, about 5 mM, about 2.5 mM, or about 1 mM; about 1 mM to about 100 mM, about 90 mM, about 80 mM, about 70 mM, about 60 mM, about 50 mM, about 40 mM, about 30 mM, about 25 mM, about 20 mM, about 15 mM, about 10 mM, about 5 mM, or about 2.5 mM; about 2.5 mM to about 100 mM, about 90 mM, about 80 mM, about 70 mM, about 60 mM, about 50 mM, about 40 mM, about 30 mM, about 25 mM, about 20 mM, about 15 mM, about 10 mM, or about 5 mM; about 5 mM to about 100 mM, about 90 mM, about 80 mM, about 70 mM, about 60 mM, about 50 mM, about 40 mM, about 30 mM, about 25 mM, about 20 mM, about 15 mM, or about 10 mM; about 10 mM to about 100 mM, about 90 mM, about 80 mM, about 70 mM, about 60 mM, about 50 mM, about 40 mM, about 30 mM, about 25 mM, about 20 mM, or about 15 mM; about 15 mM to about 100 mM, about 90 mM, about 80 mM, about 70 mM, about 60 mM, about 50 mM, about 40 mM, about 30 mM, about 25 mM, or about 20 mM; about 20 mM to about 100 mM, about 90 mM, about 80 mM, about 70 mM, about 60 mM, about 50 mM, about 40 mM, about 30 mM, or about 25 mM; about 25 mM to about 100 mM, about 90 mM, about 80 mM, about 70 mM, about 60 mM, about 50 mM, about 40 mM, or about 30 mM; about 30 mM to about 100 mM, about 90 mM, about 80 mM, about 70 mM, about 60 mM, about 50 mM, or about 40 mM; about 40 mM to about 100 mM, about 90 mM, about 80 mM, about 70 mM, about 60 mM, or about 50 mM; about 50 mM to about 100 mM, about 90 mM, about 80 mM, about 70 mM, or about 60 mM; about 60 mM to about 100 mM, about 90 mM, about 80 mM, or about 70 mM; about 70 mM to about 100 mM, about 90 mM, or about 80 mM; about 80 mM to about 100 mM, or about 90 mM; or about 90 mM to about 100 mM. In some embodiments, the concentration of folic acid in the culture medium can be about 0.01 mM to about 100 mM, about 90 mM, about 80 mM, about 70 mM, about 60 mM, about 50 mM, about 40 mM, about 30 mM, about 25 mM, about 20 mM, about 15 mM, about 10 mM, about 5 mM, about 2.5 mM, about 1 mM, about 0.5 mM, about 0.1 mM, or about 0.05 mM; about 0.05 mM to about 100 mM, about 90 mM, about 80 mM, about 70 mM, about 60 mM, about 50 mM, about 40 mM, about 30 mM, about 25 mM, about 20 mM, about 15 mM, about 10 mM, about 5 mM, about 2.5 mM, about 1 mM, about 0.5 mM, or about 0.1 mM; about 0.1 mM to about 100 mM, about 90 mM, about 80 mM, about 70 mM, about 60 mM, about 50 mM, about 40 mM, about 30 mM, about 25 mM, about 20 mM, about 15 mM, about 10 mM, about 5 mM, about 2.5 mM, about 1 mM, or about 0.5 mM; about 0.5 mM to about 100 mM, about 90 mM, about 80 mM, about 70 mM, about 60 mM, about 50 mM, about 40 mM, about 30 mM, about 25 mM, about 20 mM, about 15 mM, about 10 mM, about 5 mM, about 2.5 mM, or about 1 mM; about 1 mM to about 100 mM, about 90 mM, about 80 mM, about 70 mM, about 60 mM, about 50 mM, about 40 mM, about 30 mM, about 25 mM, about 20 mM, about 15 mM, about 10 mM, about 5 mM, or about 2.5 mM; about 2.5 mM to about 100 mM, about 90 mM, about 80 mM, about 70 mM, about 60 mM, about 50 mM, about 40 mM, about 30 mM, about 25 mM, about 20 mM, about 15 mM, about 10 mM, or about 5 mM; about 5 mM to about 100 mM, about 90 mM, about 80 mM, about 70 mM, about 60 mM, about 50 mM, about 40 mM, about 30 mM, about 25 mM, about 20 mM, about 15 mM, or about 10 mM; about 10 mM to about 100 mM, about 90 mM, about 80 mM, about 70 mM, about 60 mM, about 50 mM, about 40 mM, about 30 mM, about 25 mM, about 20 mM, or about 15 mM; about 15 mM to about 100 mM, about 90 mM, about 80 mM, about 70 mM, about 60 mM, about 50 mM, about 40 mM, about 30 mM, about 25 mM, or about 20 mM; about 20 mM to about 100 mM, about 90 mM, about 80 mM, about 70 mM, about 60 mM, about 50 mM, about 40 mM, about 30 mM, or about 25 mM; about 25 mM to about 100 mM, about 90 mM, about 80 mM, about 70 mM, about 60 mM, about 50 mM, about 40 mM, or about 30 mM; about 30 mM to about 100 mM, about 90 mM, about 80 mM, about 70 mM, about 60 mM, about 50 mM, or about 40 mM; about 40 mM to about 100 mM, about 90 mM, about 80 mM, about 70 mM, about 60 mM, or about 50 mM; about 50 mM to about 100 mM, about 90 mM, about 80 mM, about 70 mM, or about 60 mM; about 60 mM to about 100 mM, about 90 mM, about 80 mM, or about 70 mM; about 70 mM to about 100 mM, about 90 mM, or about 80 mM; about 80 mM to about 100 mM, or about 90 mM; or about 90 mM to about 100 mM.

In some examples, the microorganism is capable of producing one-carbon THF intermediates (e.g., formyl-THF, methylene-THF, methenyl-THF, and methyl-THF) when cultured (i) in a culture medium including methanol, and (ii) under conditions sufficient to produce one-carbon THF intermediates. In some examples, the culture medium includes a concentration of methanol sufficient to produce one-carbon donor for production of one or more purine alkaloids. In some examples, the culture medium includes a concentration of methanol of about 0.001% (v/v) to about 5.0% (v/v), about 4.5% (v/v), about 4.0% (v/v), about 3.5% (v/v), about 3.0% (v/v), about 2.5% (v/v), about 2.0% (v/v), about 1.5% (v/v), about 1.0% (v/v), about 0.8% (v/v), about 0.6% (v/v), about 0.4% (v/v), about 0.2% (v/v), about 0.1% (v/v), about 0.05% (v/v), about 0.01% (v/v), or about 0.005% (v/v); about 0.005% (v/v) to about 5.0% (v/v), about 4.5% (v/v), about 4.0% (v/v), about 3.5% (v/v), about 3.0% (v/v), about 2.5% (v/v), about 2.0% (v/v), about 1.5% (v/v), about 1.0% (v/v), about 0.8% (v/v), about 0.6% (v/v), about 0.4% (v/v), about 0.2% (v/v), about 0.1% (v/v), about 0.05% (v/v), or about 0.01% (v/v); about 0.01% (v/v) to about 5.0% (v/v), about 4.5% (v/v), about 4.0% (v/v), about 3.5% (v/v), about 3.0% (v/v), about 2.5% (v/v), about 2.0% (v/v), about 1.5% (v/v), about 1.0% (v/v), about 0.8% (v/v), about 0.6% (v/v), about 0.4% (v/v), about 0.2% (v/v), about 0.1% (v/v), or about 0.05% (v/v); about 0.05% (v/v) to about 5.0% (v/v), about 4.5% (v/v), about 4.0% (v/v), about 3.5% (v/v), about 3.0% (v/v), about 2.5% (v/v), about 2.0% (v/v), about 1.5% (v/v), about 1.0% (v/v), about 0.8% (v/v), about 0.6% (v/v), about 0.4% (v/v), about 0.2% (v/v), or about 0.1% (v/v); about 0.1% (v/v) to about 5.0% (v/v), about 4.5% (v/v), about 4.0% (v/v), about 3.5% (v/v), about 3.0% (v/v), about 2.5% (v/v), about 2.0% (v/v), about 1.5% (v/v), about 1.0% (v/v), about 0.8% (v/v), about 0.6% (v/v), about 0.4% (v/v), or about 0.2% (v/v); about 0.2% (v/v) to about 5.0% (v/v), about 4.5% (v/v), about 4.0% (v/v), about 3.5% (v/v), about 3.0% (v/v), about 2.5% (v/v), about 2.0% (v/v), about 1.5% (v/v), about 1.0% (v/v), about 0.8% (v/v), about 0.6% (v/v), or about 0.4% (v/v); about 0.4% (v/v) to about 5.0% (v/v), about 4.5% (v/v), about 4.0% (v/v), about 3.5% (v/v), about 3.0% (v/v), about 2.5% (v/v), about 2.0% (v/v), about 1.5% (v/v), about 1.0% (v/v), about 0.8% (v/v), or about 0.6% (v/v); about 0.6% (v/v) to about 5.0% (v/v), about 4.5% (v/v), about 4.0% (v/v), about 3.5% (v/v), about 3.0% (v/v), about 2.5% (v/v), about 2.0% (v/v), about 1.5% (v/v), about 1.0% (v/v), or about 0.8% (v/v); about 0.8% (v/v) to about 5.0% (v/v), about 4.5% (v/v), about 4.0% (v/v), about 3.5% (v/v), about 3.0% (v/v), about 2.5% (v/v), about 2.0% (v/v), about 1.5% (v/v), or about 1.0% (v/v); about 1.0% (v/v) to about 5.0% (v/v), about 4.5% (v/v), about 4.0% (v/v), about 3.5% (v/v), about 3.0% (v/v), about 2.5% (v/v), about 2.0% (v/v), or about 1.5% (v/v); about 1.5% (v/v) to about 5.0% (v/v), about 4.5% (v/v), about 4.0% (v/v), about 3.5% (v/v), about 3.0% (v/v), about 2.5% (v/v), about 2.0% (v/v), about 1.5% (v/v), or about 1.0% (v/v); about 1.0% (v/v) to about 5.0% (v/v), about 4.5% (v/v), about 4.0% (v/v), about 3.5% (v/v), about 3.0% (v/v), about 2.5% (v/v), or about 2.0% (v/v); about 2.0% (v/v) to about 5.0% (v/v), about 4.5% (v/v), about 4.0% (v/v), about 3.5% (v/v), about 3.0% (v/v), or about 2.5% (v/v); about 2.5% (v/v) to about 5.0% (v/v), about 4.5% (v/v), about 4.0% (v/v), about 3.5% (v/v), or about 3.0% (v/v); about 3.0% (v/v) to about 5.0% (v/v), about 4.5% (v/v), about 4.0% (v/v), or about 3.5% (v/v); about 3.5% (v/v) to about 5.0% (v/v), about 4.5% (v/v), or about 4.0% (v/v); about 4.0% (v/v) to about 5.0% (v/v), or about 4.5% (v/v); about 4.5% (v/v) to about 5.0% (v/v).

In some examples, the microorganism is capable of overproducing folate when cultured in a culture medium including one or more (e.g., two, three, four, or five) of: methotrexate, trimethoprim, pemetrexed, proguanil, and primethamine. The amount of one or more of methotrexate, trimethoprim, pemetrexed, proguanil, and primethamine can be determined by those skilled in the art, e.g., the amount can be determined by determining the lethal dose of one or more of methotrexate, trimethoprim, pemetrexed, proguanil, and primethamine for the microorganism. In some examples, the concentration of each of the one or more of methotrexate, trimethoprim, pemetrexed, proguanil, and primethamine in the culture medium is about 0.001 mM to about 50 mM, about 45 mM, about 40 mM, about 35 mM, about 30 mM, about 25 mM, about 20 mM, about 15 mM, about 10 mM, about 8 mM, about 6 mM, about 4 mM, about 2 mM, about 1 mM, about 0.5 mM, about 0.1 mM, about 0.05 mM, about 0.01 mM, or about 0.005 mM; about 0.005 mM to about 50 mM, about 45 mM, about 40 mM, about 35 mM, about 30 mM, about 25 mM, about 20 mM, about 15 mM, about 10 mM, about 8 mM, about 6 mM, about 4 mM, about 2 mM, about 1 mM, about 0.5 mM, about 0.1 mM, about 0.05 mM, or about 0.01 mM; about 0.01 mM to about 50 mM, about 45 mM, about 40 mM, about 35 mM, about 30 mM, about 25 mM, about 20 mM, about 15 mM, about 10 mM, about 8 mM, about 6 mM, about 4 mM, about 2 mM, about 1 mM, about 0.5 mM, about 0.1 mM, or about 0.05 mM; about 0.05 mM to about 50 mM, about 45 mM, about 40 mM, about 35 mM, about 30 mM, about 25 mM, about 20 mM, about 15 mM, about 10 mM, about 8 mM, about 6 mM, about 4 mM, about 2 mM, about 1 mM, about 0.5 mM, or about 0.1 mM; about 0.1 mM to about 50 mM, about 45 mM, about 40 mM, about 35 mM, about 30 mM, about 25 mM, about 20 mM, about 15 mM, about 10 mM, about 8 mM, about 6 mM, about 4 mM, about 2 mM, about 1 mM, or about 0.5 mM; about 0.5 mM to about 50 mM, about 45 mM, about 40 mM, about 35 mM, about 30 mM, about 25 mM, about 20 mM, about 15 mM, about 10 mM, about 8 mM, about 6 mM, about 4 mM, about 2 mM, or about 1 mM; about 1 mM to about 50 mM, about 45 mM, about 40 mM, about 35 mM, about 30 mM, about 25 mM, about 20 mM, about 15 mM, about 10 mM, about 8 mM, about 6 mM, about 4 mM, or about 2 mM; about 2 mM to about 50 mM, about 45 mM, about 40 mM, about 35 mM, about 30 mM, about 25 mM, about 20 mM, about 15 mM, about 10 mM, about 8 mM, about 6 mM, or about 4 mM; about 4 mM to about 50 mM, about 45 mM, about 40 mM, about 35 mM, about 30 mM, about 25 mM, about 20 mM, about 15 mM, about 10 mM, about 8 mM, or about 6 mM; about 6 mM to about 50 mM, about 45 mM, about 40 mM, about 35 mM, about 30 mM, about 25 mM, about 20 mM, about 15 mM, about 10 mM, or about 8 mM; about 8 mM to about 50 mM, about 45 mM, about 40 mM, about 35 mM, about 30 mM, about 25 mM, about 20 mM, about 15 mM, or about 10 mM; about 10 mM to about 50 mM, about 45 mM, about 40 mM, about 35 mM, about 30 mM, about 25 mM, about 20 mM, or about 15 mM; about 15 mM to about 50 mM, about 45 mM, about 40 mM, about 35 mM, about 30 mM, about 25 mM, or about 20 mM; about 20 mM to about 50 mM, about 45 mM, about 40 mM, about 35 mM, about 30 mM, or about 25 mM; about 25 mM to about 50 mM, about 45 mM, about 40 mM, about 35 mM, or about 30 mM; about 30 mM to about 50 mM, about 45 mM, about 40 mM, or about 35 mM; about 35 mM to about 50 mM, about 45 mM, or about 40 mM; about 40 mM to about 50 mM, or about 45 mM; or about 45 mM to about 50 mM.

In some examples, the microorganism includes one or more of a sequence encoding a modified GMP synthetase, a sequence encoding a modified adenylosuccinate synthetase, a sequence encoding a modified guanosine kinase, a sequence encoding a modified purine repressor, a sequence encoding a modified purine nucleoside phosphorylase, a sequence encoding a modified xanthine dehydrogenase, and a sequences encoding a modified glucose-6-phosphate isomerase. In some examples, one or more of the modified GMP synthetase, the modified adenylosuccinate synthetase, the modified guanosine kinase, the modified purine repressor, the modified purine nucleoside phosphorylase, the modified xanthine dehydrogenase, and the modified glucose-6-phosphate isomerase have decreased activity as compared to the corresponding wildtype enzyme. For example, one or more of the modified GMP synthetase, the modified adenylosuccinate synthetase, the modified guanosine kinase, the modified purine repressor, the modified purine nucleoside phosphorylase, the modified xanthine dehydrogenase, and the modified glucose-6-phosphate isomerase can have at least a 5%, a 10%, a 15%, a 20%, a 25%, a 30%, a 35%, a 40%, a 45%, a 50%, a 55%, a 60%, a 65%, a 70%, a 75%, a 80%, a 85%, a 90%, or a 95% decrease in activity as compared to the corresponding wildtype enzyme. In some examples, the microorganism does not include one or more of: a sequence encoding an active GMP synthetase, a sequence encoding an active adenylosuccinate synthetase, a sequence encoding an active guanosine kinase, a sequence encoding an active purine repressor, a sequence encoding a purine nucleoside phosphorylase, a sequence encoding a xanthine dehydrogenase, and a sequence encoding a glucose-6-phosphate isomerase.

In some examples, the microorganism has an increased rate of conversion of 5-phospho-α-D-ribosyl-1-pyrophosphate to xanthosine 5-monophosphate, through an intermediate of inosine 5-monophosphate, as compared to the rate of the conversion in a wildtype cell. For example, the microorganism can have at least a 5%, a 10%, a 15%, a 20%, a 25%, a 30%, a 35%, a 40%, a 45%, a 50%, a 55%, a 60%, a 65%, a 70%, a 75%, a 80%, a 85%, a 90%, or a 95% increase in the rate of conversion of 5-phospho-α-D-ribosyl-1-pyrophosphate to xanthosine 5-monophosphate, through an intermediate of inosine 5-monophosphate, as compared to the rate of the conversion in a wildtype cell.

In some embodiments, wherein two or more of the 7-methylxanthosine synthase, the theobromine synthase, and the caffeine synthase are co-located in the microorganism. For example, any of the heterologous nucleic acids described herein can include a sequence encoding a fusion protein including a (i) protein scaffold domain or a protein ligand that interacts with a protein scaffold domain, and (ii) a 7-methylxanthosine synthase, a theobromine synthase, a caffeine synthase, a S-adenosyl-methionine synthetase, a S-adenosyl-L-homocysteine hydrolase, a methionine synthase, an adenosine deaminase, an adenine phosphoribosyltransferase, a methylene-tetrahydrofolate (THF) reductase, a glycine decarboxylase, a serine hydroxymethyltransferase, a formate-tetrahydrofolate ligase, a dihydrofolate reductase, a GTP cyclohydrolase, a aminodeoxychorismate synthase, a dihydrofolate synthase, a transporter of one or both of methionine and 2-hydroxy-4-methylthio-butanoic acid, a guanosine deaminase, a xanthine, adenine, or guanine phosphoribosyl transferase, a GTP cyclohydrolase, an aminodeoxychorismate synthase, a dihydrofolate synthase, and a 5' nucleotidase ushA, a 5-phospho-α-D-ribosyl-1-pyrophosphate synthetase, a 5-phospho-α-D-ribosyl-1-pyrophosphate amidotransferase, or an inosine 5-monophosphate dehydrogenase. A protein scaffold domain is a protein domain that selectively binds to protein ligand that interacts with a protein scaffold domain. A protein scaffold domain and/or a protein ligand that interacts with a protein scaffold domain can have a total of 5 amino acids to about 500 amino acids, about 450 amino acids, about 400 amino acids, about 350 amino acids, about 300 amino acids, about 250 amino acids, about 200 amino acids, about 150 amino acids, about 100 amino acids, about 80 amino acids, about 60 amino acids, about 40 amino acids, about 20 amino acids, or about 10 amino acids; about 10 amino acids to about 500 amino acids, about 450 amino acids, about 400 amino acids, about 350 amino acids, about 300 amino acids, about 250 amino acids, about 200 amino acids, about 150 amino acids, about 100 amino acids, about 80 amino acids, about 60 amino acids, about 40 amino acids, or about 20 amino acids; about 20 amino acids to about 500 amino acids, about 450 amino acids, about 400 amino acids, about 350 amino acids, about 300 amino acids, about 250 amino acids, about 200 amino acids, about 150 amino acids, about 100 amino acids, about 80 amino acids, about 60 amino acids, or about 40 amino acids; about 40 amino acids to about 500 amino acids, about 450 amino acids, about 400 amino acids, about 350 amino acids, about 300 amino acids, about 250 amino acids, about 200 amino acids, about 150 amino acids, about 100 amino acids, about 80 amino acids, or about 60 amino acids; about 60 amino acids to about 500 amino acids, about 450 amino acids, about 400 amino acids, about 350 amino acids, about 300 amino acids, about 250 amino acids, about 200 amino acids, about 150 amino acids, about 100 amino acids, or about 80 amino acids; about 80 amino acids to about 500 amino acids, about 450 amino acids, about 400 amino acids, about 350 amino acids, about 300 amino acids, about 250 amino acids, about 200 amino acids, about 150 amino acids, or about 100 amino acids; about 100 amino acids to about 500 amino acids, about 450 amino acids, about 400 amino acids, about 350 amino acids, about 300 amino acids, about 250 amino acids, about 200 amino acids, or about 150 amino acids; about 150 amino acids to about 500 amino acids, about 450 amino acids, about 400 amino acids, about 350 amino acids, about 300 amino acids, about 250 amino acids, or about 200 amino acids; about 200 amino acids to about 500 amino acids, about 450 amino acids, about 400 amino acids, about 350 amino acids, about 300 amino acids, or about 250 amino acids; about 250 amino acids to about 500 amino acids, about 450 amino acids, about 400 amino acids, about 350 amino acids, to about 300 amino acids; about 300 amino acids to about 500 amino acids, about 450 amino acids, about 400 amino acids, or about 350 amino acids; about 350 amino acids to about 500 amino acids, about 450 amino acids, or about 400 amino acids; about 400 amino acids to about 500 amino acids or about 450 amino acids; or about 450 amino acids to about 500 amino acids. Non-limiting examples of pairs of a synthetic protein scaffold domains include GBD, PDZ, and SH3 and their corresponding protein ligands (Dueber et al., Nat Biotechnol. 27(8): 753-759, 2009). The protein scaffold domain and the protein ligand can be positioned at the N-terminus or at the C-terminus of the fusion protein.

One or more (e.g., two or three) of the heterologous sequence encoding a 7-methylxanothosine synthase, the heterologous sequence encoding a theobromine synthase, and the heterologous sequence encoding caffeine synthase can be operably linked to a promoter (e.g., a yeast promoter or a bacterial promoter) (e.g., a constitutive or an inducible promoter) in order to promote transcription of the one or more heterologous sequence in the microorganism. In addition, one or more of the heterologous sequence encoding a S-adenosyl-methionine synthetase, the heterologous sequence encoding a S-adenosyl-L-homocysteine hydrolase, the heterologous sequence encoding a methionine synthase, the heterologous sequence encoding an adenosine deaminase, the heterologous sequence encoding an adenine phosphoribosyltransferase, the heterologous sequence encoding a methylene-tetrahydrofolate (THF) reductase, the heterologous sequence encoding a glycine decarboxylase, the heterologous sequence encoding a serine hydroxymethyltransferase, the heterologous sequence encoding a formate-tetrahydrofolate ligase, the heterologous sequence encoding a dihydrofolate reductase, the heterologous sequence encoding a GTP cyclohydrolase, the heterologous sequence encoding a aminodeoxychorismate synthase, the heterologous sequence encoding a dihydrofolate synthase, the heterologous sequence encoding a transporter of one or both of methionine and 2-hydroxy-4-methylthio-butanoic acid, the heterologous sequence encoding a guanosine deaminase, the heterologous sequence encoding a xanthine, adenine, or guanine phosphoribosyl transferase, the heterologous sequence encoding a GTP cyclohydrolase, the heterologous sequence encoding an aminodeoxychorismate synthase, the heterologous sequence encoding a dihydrofolate synthase, the heterologous sequence encoding a 5' nucleotidase, the heterologous sequence encoding 5-phospho-α-D-ribosyl-1-pyrophosphate synthetase, the heterologous sequence encoding a 5-phospho-α-D-ribosyl-1-pyrophosphate amidotransferase, and the heterologous sequence encoding an inosine 5-monophosphate dehydrogenase can be operably linked to a promoter (e.g., a yeast promoter or a bacterial promoter) (e.g., a constitutive or an inducible promoter) in order to promote transcription of the one or more heterologous sequence in the microorganism.

In some examples of any of the microorganisms described herein, the microorganism further includes a nucleic acid that encodes a selectable marker (e.g., an antibiotic resistance gene). In some examples of any of the microorganisms described herein, the sequence encoding any of the proteins described herein can be codon-optimized to accomplish efficient expression of the protein in the foreign host.

In some examples of any of the microorganisms described herein, the microorganism has one of both of an increased level of S-adenosyl methionine and an increased rate of recycling of S-adenosyl homocysteine, as compared to a corresponding wildtype microorganism (e.g., the same microorganism not including any of the genetic modifications described herein). For example, any of the microorganisms described herein can have a level of S-adenosyl methionine that is at least 10%, at least 20%, at least 30%, at least 40%, at least 50%, at least 60%, at least 70%, at least 80%, at least 90%, at least 100%, at least 110%, at least 120%, at least 130%, at least 140%, at least 150%, at least 160%, at least 170%, at least 180%, at least 190%, at least 200%, at least 210%, at least 220%, at least 230%, at least 240%, at least 250%, at least 260%, at least 270%, at least 280%, at least 290%, at least 300%, at least 310%, at least 320%, at least 330%, at least 340%, at least 350%, at least 360%, at least 370%, at least 380%, at least 390%, or at least 400% increased as compared to the level of S-adenosyl methionine in a corresponding wildtype microorganism. For example, any of the microorganisms described herein can have a level of S-adenosyl methionine that is about 10% to about 400%, about 390%, about 380%, about 370%, about 360%, about 350%, about 340%, about 330%, about 320%, about 310%, about 300%, about 290%, about 280%, about 270%, about 260%, about 250%, about 240%, about 230%, about 220%, about 210%, about 200%, about 190%, about 180%, about 170%, about 160%, about 150%, about 140%, about 130%, about 120%, about 110%, about 100%, about 90%, about 80%, about 70%, about 60%, about 50%, about 40%, or about 30%; about 20% to about 400%, about 390%, about 380%, about 370%, about 360%, about 350%, about 340%, about 330%, about 320%, about 310%, about 300%, about 290%, about 280%, about 270%, about 260%, about 250%, about 240%, about 230%, about 220%, about 210%, about 200%, about 190%, about 180%, about 170%, about 160%, about 150%, about 140%, about 130%, about 120%, about 110%, about 100%, about 90%, about 80%, about 70%, about 60%, about 50%, or about 40%; about 30% to about 400%, about 390%, about 380%, about 370%, about 360%, about 350%, about 340%, about 330%, about 320%, about 310%, about 300%, about 290%, about 280%, about 270%, about 260%, about 250%, about 240%, about 230%, about 220%, about 210%, about 200%, about 190%, about 180%, about 170%, about 160%, about 150%, about 140%, about 130%, about 120%, about 110%, about 100%, about 90%, about 80%, about 70%, about 60%, or about 50%; about 40% to about 400%, about 390%, about 380%, about 370%, about 360%, about 350%, about 340%, about 330%, about 320%, about 310%, about 300%, about 290%, about 280%, about 270%, about 260%, about 250%, about 240%, about 230%, about 220%, about 210%, about 200%, about 190%, about 180%, about 170%, about 160%, about 150%, about 140%, about 130%, about 120%, about 110%, about 100%, about 90%, about 80%, about 70%, or about 60%; about 50% to about 400%, about 390%, about 380%, about 370%, about 360%, about 350%, about 340%, about 330%, about 320%, about 310%, about 300%, about 290%, about 280%, about 270%, about 260%, about 250%, about 240%, about 230%, about 220%, about 210%, about 200%, about 190%, about 180%, about 170%, about 160%, about 150%, about 140%, about 130%, about 120%, about 110%, about 100%, about 90%, about 80%, or about 70%; about 60% to about 400%, about 390%, about 380%, about 370%, about 360%, about 350%, about 340%, about 330%, about 320%, about 310%, about 300%, about 290%, about 280%, about 270%, about 260%, about 250%, about 240%, about 230%, about 220%, about 210%, about 200%, about 190%, about 180%, about 170%, about 160%, about 150%, about 140%, about 130%, about 120%, about 110%, about 100%, about 90%, or about 80%; about 70% to about 400%, about 390%, about 380%, about 370%, about 360%, about 350%, about 340%, about 330%, about 320%, about 310%, about 300%, about 290%, about 280%, about 270%, about 260%, about 250%, about 240%, about 230%, about 220%, about 210%, about 200%, about 190%, about 180%, about 170%, about 160%, about 150%, about 140%, about 130%, about 120%, about 110%, about 100%, or about 90%; about 80% to about 400%, about 390%, about 380%, about 370%, about 360%, about 350%, about 340%, about 330%, about 320%, about 310%, about 300%, about 290%, about 280%, about 270%, about 260%, about 250%, about 240%, about 230%, about 220%, about 210%, about 200%, about 190%, about 180%, about 170%, about 160%, about 150%, about 140%, about 130%, about 120%, about 110%, or about 100%; about 90% to about 400%, about 390%, about 380%, about 370%, about 360%, about 350%, about 340%, about 330%, about 320%, about 310%, about 300%, about 290%, about 280%, about 270%, about 260%, about 250%, about 240%, about 230%, about 220%, about 210%, about 200%, about 190%, about 180%, about 170%, about 160%, about 150%, about 140%, about 130%, about 120%, or about 110%; about 100% to about 400%, about 390%, about 380%, about 370%, about 360%, about 350%, about 340%, about 330%, about 320%, about 310%, about 300%, about 290%, about 280%, about 270%, about 260%, about 250%, about 240%, about 230%, about 220%, about 210%, about 200%, about 190%, about 180%, about 170%, about 160%, about 150%, about 140%, about 130%, or about 120%; about 110% to about 400%, about 390%, about 380%, about 370%, about 360%, about 350%, about 340%, about 330%, about 320%, about 310%, about 300%, about 290%, about 280%, about 270%, about 260%, about 250%, about 240%, about 230%, about 220%, about 210%, about 200%, about 190%, about 180%, about 170%, about 160%, about 150%, about 140%, or about 130%; about 120% to about 400%, about 390%, about 380%, about 370%, about 360%, about 350%, about 340%, about 330%, about 320%, about 310%, about 300%, about 290%, about 280%, about 270%, about 260%, about 250%, about 240%, about 230%, about 220%, about 210%, about 200%, about 190%, about 180%, about 170%, about 160%, about 150%, or about 140%; about 130% to about 400%, about 390%, about 380%, about 370%, about 360%, about 350%, about 340%, about 330%, about 320%, about 310%, about 300%, about 290%, about 280%, about 270%, about 260%, about 250%, about 240%, about 230%, about 220%, about 210%, about 200%, about 190%, about 180%, about 170%, about 160%, or about 150%; about 140% to about 400%, about 390%, about 380%, about 370%, about 360%, about 350%, about 340%, about 330%, about 320%, about 310%, about 300%, about 290%, about 280%, about 270%, about 260%, about 250%, about 240%, about 230%, about 220%, about 210%, about 200%, about 190%, about 180%, about 170%, or about 160%; about 150% to about 400%, about 390%, about 380%, about 370%, about 360%, about 350%, about 340%, about 330%, about 320%, about 310%, about 300%, about 290%, about 280%, about 270%, about 260%, about 250%, about 240%, about 230%, about 220%, about 210%, about 200%, about 190%, about 180%, or about 170%; about 160% to about 400%, about 390%, about 380%, about 370%, about 360%, about 350%, about 340%, about 330%, about 320%, about 310%, about 300%, about 290%, about 280%, about 270%, about 260%, about 250%, about 240%, about 230%, about 220%, about 210%, about 200%, about 190%, or about 180%; about 170% to about 400%, about 390%, about 380%, about 370%, about 360%, about 350%, about 340%, about 330%, about 320%, about 310%, about 300%, about 290%, about 280%, about 270%, about 260%, about 250%, about 240%, about 230%, about 220%, about 210%, about 200%, or about 190%; about 190% to about 400%, about 390%, about 380%, about 370%, about 360%, about 350%, about 340%, about 330%, about 320%, about 310%, about 300%, about 290%, about 280%, about 270%, about 260%, about 250%, about 240%, about 230%, about 220%, or about 210%; about 200% to about 400%, about 390%, about 380%, about 370%, about 360%, about 350%, about 340%, about 330%, about 320%, about 310%, about 300%, about 290%, about 280%, about 270%, about 260%, about 250%, about 240%, about 230%, or about 220%; about 210% to about 400%, about 390%, about 380%, about 370%, about 360%, about 350%, about 340%, about 330%, about 320%, about 310%, about 300%, about 290%, about 280%, about 270%, about 260%, about 250%, about 240%, or about 230%; about 220% to about 400%, about 390%, about 380%, about 370%, about 360%, about 350%, about 340%, about 330%, about 320%, about 310%, about 300%, about 290%, about 280%, about 270%, about 260%, about 250%, or about 240%; about 230% to about 400%, about 390%, about 380%, about 370%, about 360%, about 350%, about 340%, about 330%, about 320%, about 310%, about 300%, about 290%, about 280%, about 270%, about 260%, or about 250%; about 240% to about 400%, about 390%, about 380%, about 370%, about 360%, about 350%, about 340%, about 330%, about 320%, about 310%, about 300%, about 290%, about 280%, about 270%, or about 260%; about 250% to about 400%, about 390%, about 380%, about 370%, about 360%, about 350%, about 340%, about 330%, about 320%, about 310%, about 300%, about 290%, about 280%, or about 270%; about 260% to about 400%, about 390%, about 380%, about 370%, about 360%, about 350%, about 340%, about 330%, about 320%, about 310%, about 300%, about 290%, or about 280%; about 270% to about 400%, about 390%, about 380%, about 370%, about 360%, about 350%, about 340%, about 330%, about 320%, about 310%, about 300%, or about 290%; about 280% to about 400%, about 390%, about 380%, about 370%, about 360%, about 350%, about 340%, about 330%, about 320%, about 310%, or about 300%; about 290% to about 400%, about 390%, about 380%, about 370%, about 360%, about 350%, about 340%, about 330%, about 320%, or about 310%; about 300% to about 400%, about 390%, about 380%, about 370%, about 360%, about 350%, about 340%, about 330%, or about 320%; about 310% to about 400%, about 390%, about 380%, about 370%, about 360%, about 350%, about 340%, or about 330%; about 320% to about 400%, about 390%, about 380%, about 370%, about 360%, about 350%, or about 340%; about 330% to about 400%, about 390%, about 380%, about 370%, about 360%, or about 350%; about 340% to about 400%, about 390%, about 380%, about 370%, or about 360%; about 350% to about 400%, about 390%, about 380%, or about 370%; about 360% to about 400%, about 390%, or about 380%; about 370% to about 400% or about 390%; or about 380% to about 400%, increased as compared to the level of S-adenosyl methionine in a corresponding wildtype microorganism.

In some examples, any of the microorganisms described herein can have a rate of recycling of S-adenosyl homocysteine that is at least 10%, at least 20%, at least 30%, at least 40%, at least 50%, at least 60%, at least 70%, at least 80%, at least 90%, at least 100%, at least 110%, at least 120%, at least 130%, at least 140%, at least 150%, at least 160%, at least 170%, at least 180%, at least 190%, at least 200%, at least 210%, at least 220%, at least 230%, at least 240%, at least 250%, at least 260%, at least 270%, at least 280%, at least 290%, at least 300%, at least 310%, at least 320%, at least 330%, at least 340%, at least 350%, at least 360%, at least 370%, at least 380%, at least 390%, or at least 400% increased as compared to the rate of recycling of S-adenosyl homocysteine in a corresponding wildtype microorganism (e.g., the same microorganism not including any of the genetic modifications described herein). For example, any of the microorganisms described herein can have a rate of recycling of S-adenosyl homocysteine that is about 10% to about 400%, about 390%, about 380%, about 370%, about 360%, about 350%, about 340%, about 330%, about 320%, about 310%, about 300%, about 290%, about 280%, about 270%, about 260%, about 250%, about 240%, about 230%, about 220%, about 210%, about 200%, about 190%, about 180%, about 170%, about 160%, about 150%, about 140%, about 130%, about 120%, about 110%, about 100%, about 90%, about 80%, about 70%, about 60%, about 50%, about 40%, or about 30%; about 20% to about 400%, about 390%, about 380%, about 370%, about 360%, about 350%, about 340%, about 330%, about 320%, about 310%, about 300%, about 290%, about 280%, about 270%, about 260%, about 250%, about 240%, about 230%, about 220%, about 210%, about 200%, about 190%, about 180%, about 170%, about 160%, about 150%, about 140%, about 130%, about 120%, about 110%, about 100%, about 90%, about 80%, about 70%, about 60%, about 50%, or about 40%; about 30% to about 400%, about 390%, about 380%, about 370%, about 360%, about 350%, about 340%, about 330%, about 320%, about 310%, about 300%, about 290%, about 280%, about 270%, about 260%, about 250%, about 240%, about 230%, about 220%, about 210%, about 200%, about 190%, about 180%, about 170%, about 160%, about 150%, about 140%, about 130%, about 120%, about 110%, about 100%, about 90%, about 80%, about 70%, about 60%, or about 50%; about 40% to about 400%, about 390%, about 380%, about 370%, about 360%, about 350%, about 340%, about 330%, about 320%, about 310%, about 300%, about 290%, about 280%, about 270%, about 260%, about 250%, about 240%, about 230%, about 220%, about 210%, about 200%, about 190%, about 180%, about 170%, about 160%, about 150%, about 140%, about 130%, about 120%, about 110%, about 100%, about 90%, about 80%, about 70%, or about 60%; about 50% to about 400%, about 390%, about 380%, about 370%, about 360%, about 350%, about 340%, about 330%, about 320%, about 310%, about 300%, about 290%, about 280%, about 270%, about 260%, about 250%, about 240%, about 230%, about 220%, about 210%, about 200%, about 190%, about 180%, about 170%, about 160%, about 150%, about 140%, about 130%, about 120%, about 110%, about 100%, about 90%, about 80%, or about 70%; about 60% to about 400%, about 390%, about 380%, about 370%, about 360%, about 350%, about 340%, about 330%, about 320%, about 310%, about 300%, about 290%, about 280%, about 270%, about 260%, about 250%, about 240%, about 230%, about 220%, about 210%, about 200%, about 190%, about 180%, about 170%, about 160%, about 150%, about 140%, about 130%, about 120%, about 110%, about 100%, about 90%, or about 80%; about 70% to about 400%, about 390%, about 380%, about 370%, about 360%, about 350%, about 340%, about 330%, about 320%, about 310%, about 300%, about 290%, about 280%, about 270%, about 260%, about 250%, about 240%, about 230%, about 220%, about 210%, about 200%, about 190%, about 180%, about 170%, about 160%, about 150%, about 140%, about 130%, about 120%, about 110%, or about 100%, or about 90%; about 80% to about 400%, about 390%, about 380%, about 370%, about 360%, about 350%, about 340%, about 330%, about 320%, about 310%, about 300%, about 290%, about 280%, about 270%, about 260%, about 250%, about 240%, about 230%, about 220%, about 210%, about 200%, about 190%, about 180%, about 170%, about 160%, about 150%, about 140%, about 130%, about 120%, about 110%, or about 100%; about 90% to about 400%, about 390%, about 380%, about 370%, about 360%, about 350%, about 340%, about 330%, about 320%, about 310%, about 300%, about 290%, about 280%, about 270%, about 260%, about 250%, about 240%, about 230%, about 220%, about 210%, about 200%, about 190%, about 180%, about 170%, about 160%, about 150%, about 140%, about 130%, about 120%, or about 110%; about 100% to about 400%, about 390%, about 380%, about 370%, about 360%, about 350%, about 340%, about 330%, about 320%, about 310%, about 300%, about 290%, about 280%, about 270%, about 260%, about 250%, about 240%, about 230%, about 220%, about 210%, about 200%, about 190%, about 180%, about 170%, about 160%, about 150%, about 140%, about 130%, or about 120%; about 110% to about 400%, about 390%, about 380%, about 370%, about 360%, about 350%, about 340%, about 330%, about 320%, about 310%, about 300%, about 290%, about 280%, about 270%, about 260%, about 250%, about 240%, about 230%, about 220%, about 210%, about 200%, about 190%, about 180%, about 170%, about 160%, about 150%, about 140%, or about 130%; about 120% to about 400%, about 390%, about 380%, about 370%, about 360%, about 350%, about 340%, about 330%, about 320%, about 310%, about 300%, about 290%, about 280%, about 270%, about 260%, about 250%, about 240%, about 230%, about 220%, about 210%, about 200%, about 190%, about 180%, about 170%, about 160%, about 150%, or about 140%; about 130% to about 400%, about 390%, about 380%, about 370%, about 360%, about 350%, about 340%, about 330%, about 320%, about 310%, about 300%, about 290%, about 280%, about 270%, about 260%, about 250%, about 240%, about 230%, about 220%, about 210%, about 200%, about 190%, about 180%, about 170%, about 160%, or about 150%; about 140% to about 400%, about 390%, about 380%, about 370%, about 360%, about 350%, about 340%, about 330%, about 320%, about 310%, about 300%, about 290%, about 280%, about 270%, about 260%, about 250%, about 240%, about 230%, about 220%, about 210%, about 200%, about 190%, about 180%, about 170%, or about 160%; about 150% to about 400%, about 390%, about 380%, about 370%, about 360%, about 350%, about 340%, about 330%, about 320%, about 310%, about 300%, about 290%, about 280%, about 270%, about 260%, about 250%, about 240%, about 230%, about 220%, about 210%, about 200%, about 190%, about 180%, or about 170%; about 160% to about 400%, about 390%, about 380%, about 370%, about 360%, about 350%, about 340%, about 330%, about 320%, about 310%, about 300%, about 290%, about 280%, about 270%, about 260%, about 250%, about 240%, about 230%, about 220%, about 210%, about 200%, about 190%, or about 180%; about 170% to about 400%, about 390%, about 380%, about 370%, about 360%, about 350%, about 340%, about 330%, about 320%, about 310%, about 300%, about 290%, about 280%, about 270%, about 260%, about 250%, about 240%, about 230%, about 220%, about 210%, about 200%, or about 190%; about 190% to about 400%, about 390%, about 380%, about 370%, about 360%, about 350%, about 340%, about 330%, about 320%, about 310%, about 300%, about 290%, about 280%, about 270%, about 260%, about 250%, about 240%, about 230%, about 220%, or about 210%; about 200% to about 400%, about 390%, about 380%, about 370%, about 360%, about 350%, about 340%, about 330%, about 320%, about 310%, about 300%, about 290%, about 280%, about 270%, about 260%, about 250%, about 240%, about 230%, or about 220%; about 210% to about 400%, about 390%, about 380%, about 370%, about 360%, about 350%, about 340%, about 330%, about 320%, about 310%, about 300%, about 290%, about 280%, about 270%, about 260%, about 250%, about 240%, or about 230%; about 220% to about 400%, about 390%, about 380%, about 370%, about 360%, about 350%, about 340%, about 330%, about 320%, about 310%, about 300%, about 290%, about 280%, about 270%, about 260%, about 250%, or about 240%; about 230% to about 400%, about 390%, about 380%, about 370%, about 360%, about 350%, about 340%, about 330%, about 320%, about 310%, about 300%, about 290%, about 280%, about 270%, about 260%, or about 250%; about 240% to about 400%, about 390%, about 380%, about 370%, about 360%, about 350%, about 340%, about 330%, about 320%, about 310%, about 300%, about 290%, about 280%, about 270%, or about 260%; about 250% to about 400%, about 390%, about 380%, about 370%, about 360%, about 350%, about 340%, about 330%, about 320%, about 310%, about 300%, about 290%, about 280%, or about 270%; about 260% to about 400%, about 390%, about 380%, about 370%, about 360%, about 350%, about 340%, about 330%, about 320%, about 310%, about 300%, about 290%, or about 280%; about 270% to about 400%, about 390%, about 380%, about 370%, about 360%, about 350%, about 340%, about 330%, about 320%, about 310%, about 300%, or about 290%; about 280% to about 400%, about 390%, about 380%, about 370%, about 360%, about 350%, about 340%, about 330%, about 320%, about 310%, or about 300%; about 290% to about 400%, about 390%, about 380%, about 370%, about 360%, about 350%, about 340%, about 330%, about 320%, or about 310%; about 300% to about 400%, about 390%, about 380%, about 370%, about 360%, about 350%, about 340%, about 330%, or about 320%; about 310% to about 400%, about 390%, about 380%, about 370%, about 360%, about 350%, about 340%, or about 330%; about 320% to about 400%, about 390%, about 380%, about 370%, about 360%, about 350%, or about 340%; about 330% to about 400%, about 390%, about 380%, about 370%, about 360%, or about 350%; about 340% to about 400%, about 390%, about 380%, about 370%, or about 360%; about 350% to about 400%, about 390%, about 380%, or about 370%; about 360% to about 400%, about 390%, or about 380%; about 370% to about 400% or about 390%; or about 380% to about 400%, increased as compared to the rate of recycling of S-adenosyl homocysteine in a corresponding wild-type microorganism.

Methods of Generating a Recombinant Bacterium or Recombinant Yeast Cell Capable of Synthesizing Purine Alkaloids Also provided herein are methods of generating a recombinant microorganism (e.g., any of the recombinant microorganisms described herein). These methods include introducing one or more (e.g., two, or three) heterologous nucleic acid selected from the group of a sequence encoding a 7-methylxanthosine synthase, a sequence encoding a theobromine synthase, and a sequence encoding a caffeine synthase into a microbacterium. In some examples, the methods further include introducing one or more (e.g., two, three, four, five, six, seven, eight, nine, ten, eleven, twelve, thirteen, fourteen, fifteen, sixteen, seventeen, eighteen, nineteen, twenty, twenty-one, twenty-two, or twenty-three) heterologous nucleic acid selected from the group of a sequence encoding a S-adenosyl-methionine synthetase; a sequence encoding a S-adenosyl-L-homocysteine hydrolase; a sequence encoding a methionine synthase; a sequence encoding an adenosine deaminase; a sequence encoding an adenine phosphoribosyltransferase; a sequence encoding a methylene-tetrahydrofolate (THF) reductase; a sequence encoding a glycine decarboxylase; a sequence encoding a serine hydroxymethyltransferase; a sequence encoding a formate-tetrahydrofolate ligase; a sequence encoding a dihydrofolate reductase; a sequence encoding a GTP cyclohydrolase; a sequence encoding a aminodeoxychorismate synthase; a sequence encoding a dihydrofolate synthase; a sequence encoding a transporter of one or both of methionine and 2-hydroxy-4-methylthio-butanoic acid; a sequence encoding a guanosine deaminase; a sequence encoding a xanthine, adenine, or guanine phosphoribosyl transferase; a sequence encoding a GTP cyclohydrolase; a sequence encoding an aminodeoxychorismate synthase; a sequence encoding a dihydrofolate synthase; and a sequence encoding 5' nucleotidase, a sequence encoding 5-phospho-α-D-ribosyl-1-pyrophosphate synthetase; a sequence encoding a 5-phospho-α-D-ribosyl-1-pyrophosphate amidotransferase; and a sequence encoding an inosine 5-monophosphate dehydrogenase. Any of the heterologous nucleic acids described herein can further include a promoter (e.g., a constitutive promoter or an inducible promoter), e.g., wherein the promoter is operably linked to the sequence encoding a protein (e.g., any of the proteins described herein) in order to allow for transcription of the sequence encoding the protein in a microorganism. In some examples, any of the heterologous nucleic acids described herein can include a sequence encoding a selectable marker (e.g., an antibiotic resistance gene). The heterologous nucleic acid can be introduced into a microorganism as a plasmid or an artificial chromosome (e.g., a bacterial artificial chromosome or a yeast artificial chromosome).

Methods for introducing a nucleic acid (e.g., any of the heterologous nucleic acids described herein) using, e.g., electroporation, cationic polymer transfection, sonoporation, impalefection, hydrodynamic delivery, magnetofection, conjugation, calcium phosphate precipitation, polyethylene glycol (PEG) transformation, natural transformation, heat shock, lipofection (e.g., liposome transfection), microinjection, and virus-mediated nucleic acid transfer. Additional methods for introducing nucleic acid into a microorganism are known in the art.

Some embodiments of any of the methods described herein can further include mutagenizing a microorganism in order to result in endogenous nucleic acid encoding at least one modified endogenous enzyme (e.g., one or more (e.g., two, three, four, five, or six) of a modified guanosine kinase, a modified purine repressor, a modified purine nucleoside phosphorylase, a modified guanosine deaminase, a modified glucose-6-phosphate isomerase, a modified GMP synthetase, and a modified adenylosuccinate synthetase). For example, a modified guanosine kinase, a modified purine repressor, a modified purine nucleoside phosphorylase, a modified guanosine deaminase, a modified glucose-6-phosphate isomerase, a modified GMP synthetase, and/or a modified adenylosuccinate synthetase can have decreased activity as compared to the wildtype guanosine kinase, wildtype purine repressor, wildtype purine nucleoside phosphorylase, wildtype guanosine deaminase, wildtype GMP synthetase, and/or adenylosuccinate synthetase, respectively. For example, the mutagenizing can be performed using chemical mutagenesis or targeted mutagenesis (e.g., using biotechnology techniques). A modified enzyme can include one or more point mutation(s) (e.g., one or more amino acid deletion(s), one or more amino acid substitution(s), and/or one or more amino acid insertion(s)) that results in inactivation of the enzyme. An inactivated enzyme can have a truncation (e.g., an N- and/or C-terminal truncation) that leads to inactivation of the enzyme. An inactivated enzyme can also have a deletion of one or more amino acids from an internal sequence within the enzyme. An inactivated enzyme can also be caused by a deletion of a nucleic acid encoding the enzyme (e.g., a complete deletion of the endogenous nucleic acid encoding the enzyme). In some examples, a microorganism as described herein can include one or more (e.g., two, three, four, five, or six) of a deletion in a nucleic acid encoding a guanosine kinase, a deletion in a nucleic acid encoding a purine repressor, a deletion in a nucleic acid encoding a purine nucleoside phosphorylase, a deletion in a nucleic acid encoding a xanthine dehydrogenase, a deletion in a nucleic acid encoding a glucose-6-phosphate isomerase, a deletion in a nucleic acid encoding a GMP synthetase, and a deletion in a nucleic acid encoding an adenylosuccinate synthetase Methods of inducing random mutagenesis in microorganisms are known in the art. For example, random mutagenesis can be induced using a chemical mutagen, ionizing radiation, fast neutron bombardment, or combinations thereof. Representative chemical mutagens include, without limitation, nitrous acid, sodium azide, acridine orange, ethidium bromide, methyl methane sulfonate (MMS), and ethyl methane sulfonate (EMS), while representative ionizing radiation includes, without limitation, x-rays, gamma rays, fast neutron irradiation, and UV irradiation. The dosage of the mutagenic chemical or radiation is determined experimentally for each type of microorganism such that a mutation frequency is obtained that is below a threshold level characterized by lethality or reproductive sterility.

Methods of targeted mutagenesis are known in the art, and include, for example, TALEN technologies (see, for example, Li et al., *Nucleic Acids Res.* 39(14):6315-6325, 2011), zinc-finger technologies (see, for example, Wright et al., *Plant J.* 44:693-705, 2005), and CRISPR technologies (see, for example, Mali et al., *Nature Methods* 10:957-963, 2013). The particular enzyme(s) inactivated in the microorganism depends upon a number of factors including, for example, the particular microorganism that is used as well as the one or more purine alkaloid that is being produced.

Similarly, selection or selective pressure also is well known and routinely used in the art. To obtain the modified or recombinant microorganisms described herein, selection can be performed in some examples, by culturing the microorganisms in the presence of a substrate that is toxic if unmethylated (e.g., any of the exemplary substrates that are toxic if unmethylated that are described herein).

Alternatively or additionally, one or more heterologous nucleic acids can be expressed (e.g., overexpressed) to produce a desired enzyme (e.g., an excess of a desired enzyme). As used herein, heterologous nucleic acid refers to any nucleic acid that is not naturally present in the specific microorganism. For example, a heterologous nucleic acid can be a nucleic acid from a different genus or species. In other examples, a heterologous nucleic acid is a sequence encoding an enzyme that is endogenously present in the microorganism that is operably linked to a promoter that is not naturally operably linked to the sequence in the microorganism. In some examples, the heterologous sequence is a codon-optimized nucleic acid (that is not the same as an endogenous nucleic acid in the microorganism).

Nucleic acids are well known in the art, and can include DNA and/or RNA. A nucleic acid can be single-stranded or double-stranded, which usually depends upon its intended use. The nucleic acids provided herein typically encode proteins. While representative nucleic acids and proteins are provided herein, nucleic acids and proteins that differ from such sequences also are provided. Nucleic acids and proteins that differ in sequence from those provided herein can have at least 50% sequence identity (e.g., at least 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% sequence identity) to those sequences provided herein (e.g., in the form of a database accession number).

In calculating percent sequence identity, two sequences are aligned and the number of identical matches of nucleotides or amino acid residues between the two sequences is determined. The number of identical matches is divided by the length of the aligned region (i.e., the number of aligned nucleotides or amino acid residues) and multiplied by 100 to arrive at a percent sequence identity value. It will be appreciated that the length of the aligned region can be a portion of one or both sequences up to the full-length size of the shortest sequence. It also will be appreciated that a single sequence can align with more than one other sequence and hence, can have different percent sequence identity values over each aligned region.

The alignment of two or more sequences to determine percent sequence identity can be performed using the computer program ClustalW and default parameters, which allows alignments of nucleic acid or protein sequences to be carried out across their entire length (global alignment). Chenna et al., 2003, Nucleic Acids Res., 31(13):3497-3500, 2003. ClustalW calculates the best match between a query and one or more subject sequences, and aligns them so that identities, similarities and differences can be determined. Gaps of one or more residues can be inserted into a query sequence, a subject sequence, or both, to maximize sequence alignments. For fast pairwise alignment of nucleic acid sequences, the default parameters can be used (i.e., word size: 2; window size: 4; scoring method: percentage; number of top diagonals: 4; and gap penalty: 5); for an alignment of multiple nucleic acid sequences, the following parameters can be used: gap opening penalty: 10.0; gap extension penalty: 5.0; and weight transitions: yes. For fast pairwise alignment of protein sequences, the following parameters can be used: word size: 1; window size: 5; scoring method: percentage; number of top diagonals: 5; and gap penalty: 3. For multiple alignment of protein sequences, the following parameters can be used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; and residue-specific gap penalties: on. ClustalW can be run, for example, at the Baylor College of Medicine Search Launcher website or at the European Bioinformatics Institute website on the World Wide Web. As discussed herein, modifications can be introduced into a nucleic acid, thereby leading to changes in the amino acid sequence of the encoded protein. For example, modifications can be introduced into nucleic acid coding sequences using mutagenesis (e.g., site-directed mutagenesis, PCR-mediated mutagenesis, random mutagenesis, TALEN, and/or CRISPR) or by chemically synthesizing a nucleic acid molecule having such changes. Such nucleic acid changes can lead to conservative and/or non-conservative amino acid substitutions at one or more amino acid residues. A "conservative amino acid substitution" is one in which one amino acid residue is replaced with a different amino acid residue having a similar side chain (see, e.g., Dayhoff et al., Atlas of Protein Sequence and Structure, 5(Suppl. 3):345-352, 1978), which provides frequency tables for amino acid substitutions), and a non-conservative substitution is one in which an amino acid residue is replaced with an amino acid residue that does not have a similar side chain.

As used herein, an "isolated" nucleic acid is a nucleic acid that is free of sequences that naturally flank one or both ends of the nucleic acid in the genome of the organism from which the isolated nucleic acid molecule is derived (e.g., a cDNA or genomic DNA fragment produced by PCR or restriction endonuclease digestion). Such an isolated nucleic acid is generally introduced into a vector (e.g., a cloning vector, or an expression vector) for convenience of manipulation or to generate a recombinant molecule. In addition, an isolated nucleic acid molecule can include an engineered nucleic acid molecule such as a recombinant or a synthetic nucleic acid molecule.

As used herein, a "purified" protein is a protein that has been separated or purified from cellular components that naturally accompany it. Typically, the protein is considered "purified" when it is at least 70% (e.g., at least 75%, 80%, 85%, 90%, 95%, or 99%) by dry weight, free from the proteins and naturally occurring molecules with which it is naturally associated. Since a protein that is chemically synthesized is, by nature, separated from the components that naturally accompany it, a synthetic protein is "purified."

Nucleic acids can be isolated using techniques routine in the art. For example, nucleic acids can be isolated using any method including, without limitation, recombinant nucleic acid technology, and/or the polymerase chain reaction (PCR). General PCR techniques are described, for example in PCR Primer: A Laboratory Manual, Dieffenbach & Dveksler, Eds., Cold Spring Harbor Laboratory Press, 1995. Recombinant nucleic acid techniques include, for example, restriction enzyme digestion and ligation, which can be used to isolate a nucleic acid. Isolated nucleic acids also can be chemically synthesized, either as a single nucleic acid molecule or as a series of oligonucleotides.

Enzymes can be purified from natural sources (e.g., a biological sample) by known methods such as DEAE ion exchange, gel filtration, and hydroxyapatite chromatography. An enzyme also can be purified, for example, by expressing a nucleic acid in an expression vector. In addition, a purified enzyme can be obtained by chemical synthesis. The extent of purity of an enzyme can be measured using any appropriate method, e.g., column chromatography, polyacrylamide gel electrophoresis, or HPLC analysis.

A vector containing a nucleic acid (e.g., a nucleic acid that encodes an enzyme) also is provided. Vectors, including expression vectors, are commercially available or can be produced by recombinant DNA techniques routine in the art. A vector containing a nucleic acid can have expression elements operably linked to such a nucleic acid, and further can include sequences such as those encoding a selectable marker (e.g., an antibiotic resistance gene). A vector containing a nucleic acid can encode a chimeric or fusion protein (i.e., a protein operatively linked to a heterologous protein, which can be at either the N-terminus or C-terminus of the protein). Representative heterologous proteins are those that can be used in purification of the encoded protein (e.g., 6×His tag, glutathione S-transferase (GST)).

Expression elements include nucleic acid sequences that direct and regulate expression of nucleic acid coding sequences. One example of an expression element is a promoter sequence. Expression elements also can include introns, enhancer sequences, response elements, or inducible elements that modulate expression of a nucleic acid. Expression elements can be of bacterial, yeast, insect, mammalian, or viral origin, and vectors can contain a combination of elements from different origins. As used herein, operably linked means that a promoter or other expression element(s) are positioned in a vector relative to a nucleic acid in such a way as to direct or regulate expression of the nucleic acid (e.g., in-frame).

Vectors as described herein can be introduced into a host cell. As used herein, "host cell" refers to the particular cell (e.g., a microorganism) into which the nucleic acid is introduced and also includes the progeny of such a cell that carry the vector. A host cell can be any microorganism (e.g., a prokaryotic or eukaryotic cell). For example, nucleic acids can be expressed in bacterial cells, such as $E.\ coli$, or yeast cells (e.g., any of the exemplary organisms described herein). Other suitable host cells are known to those skilled in the art. Many methods for introducing nucleic acids into host cells, both in vivo and in vitro, are well known to those skilled in the art and include, without limitation, conjugation, electroporation, calcium phosphate precipitation, polyethylene glycol (PEG) transformation, heat shock, lipofection, microinjection, and virus-mediated nucleic acid transfer.

Nucleic acids can be detected using any number of amplification techniques (see, e.g., PCR Primer: A Laboratory Manual, 1995, Dieffenbach & Dveksler, Eds., Cold Spring Harbor Laboratory Press, Cold Spring Harbor, N.Y.; and U.S. Pat. Nos. 4,683,195; 4,683,202; 4,800,159; and 4,965,188) with an appropriate pair of oligonucleotides (e.g., primers). A number of modifications to the original PCR have been developed and can be used to detect a nucleic acid.

Nucleic acids also can be detected using hybridization. Hybridization between nucleic acids is discussed in detail in Sambrook et al. (Molecular Cloning: A Laboratory Manual, 2nd Ed., Cold Spring Harbor Laboratory Press, Cold Spring Harbor, N.Y.; Sections 7.37-7.57, 9.47-9.57, 11.7-11.8, and 11.45-11.57, 1989). Sambrook et al. discloses suitable Southern blot conditions for oligonucleotide probes less than about 100 nucleotides (Sections 11.45-11.46). The Tm between a sequence that is less than 100 nucleotides in length and a second sequence can be calculated using the formula provided in Section 11.46. Sambrook et al. additionally discloses Southern blot conditions for oligonucleotide probes greater than about 100 nucleotides (see Sections 9.47-9.54). The Tm between a sequence greater than 100 nucleotides in length and a second sequence can be calculated using the formula provided in Sections 9.50-9.51 of Sambrook et al.

The conditions under which membranes containing nucleic acids are prehybridized and hybridized, as well as the conditions under which membranes containing nucleic acids are washed to remove excess and non-specifically bound probe, can play a significant role in the stringency of the hybridization. Such hybridizations and washes can be performed, where appropriate, under moderate or high stringency conditions. For example, washing conditions can be made more stringent by decreasing the salt concentration in the wash solutions and/or by increasing the temperature at which the washes are performed. Simply by way of example, high stringency conditions typically include a wash of the membranes in 0.2×SSC at 65° C.

In addition, interpreting the amount of hybridization can be affected, for example, by the specific activity of the labeled oligonucleotide probe, by the number of probe-binding sites on the template nucleic acid to which the probe has hybridized, and by the amount of exposure of an autoradiograph or other detection medium. It will be readily appreciated by those of ordinary skill in the art that although any number of hybridization and washing conditions can be used to examine hybridization of a probe nucleic acid molecule to immobilized target nucleic acids, it is more important to examine hybridization of a probe to target nucleic acids under identical hybridization, washing, and exposure conditions. Preferably, the target nucleic acids are on the same membrane.

A nucleic acid molecule is deemed to hybridize to a nucleic acid but not to another nucleic acid if hybridization to a nucleic acid is at least 5-fold (e.g., at least 6-fold, 7-fold, 8-fold, 9-fold, 10-fold, 20-fold, 50-fold, or 100-fold) greater than hybridization to another nucleic acid. The amount of hybridization can be quantitated directly on a membrane or from an autoradiograph using, for example, a Phosphorlmager or a Densitometer (Molecular Dynamics, Sunnyvale, Calif.).

Proteins can be detected using antibodies. Techniques for detecting proteins using antibodies include enzyme linked immunosorbent assays (ELISAs), Western blots, immunoprecipitations and immunofluorescence. An antibody can be polyclonal or monoclonal. An antibody having specific binding affinity for a protein can be generated using methods well known in the art. The antibody can be attached to a solid support such as a microtiter plate using methods known in the art. In the presence of a protein, an antibody-protein complex is formed.

Detection (e.g., of an amplification product, a hybridization complex, or a protein) is usually accomplished using detectable labels. The term "label" is intended to encompass the use of direct labels as well as indirect labels. Detectable labels include enzymes, prosthetic groups, fluorescent materials, luminescent materials, bioluminescent materials, and radioactive materials.

These methods can further include testing whether the microorganism produces one or more purine alkaloid(s) in a culture medium, when the microorganism is cultured under conditions sufficient to produce the one or more purine alkaloid (e.g., using any of the methods described herein or known in the art).

Compositions and Kits

Also provided herein are compositions that include any of the microorganisms provided herein. In some examples, the composition may further include one or both of dimethylsulfoxide and glycerol. In some examples, the composition further comprises a culture medium (e.g., any of the culture media described herein). In some examples, the composition further includes one or more components for culturing any of the microorganisms provided herein, e.g., a carbon source (e.g., any of the carbon sources described herein), a nitrogen source (e.g., any of the nitrogen sources described herein), a one-carbon donor (e.g., any of the one carbon donors described herein), a nucleobase, a nucleoside, and/or a nucleotide (e.g., any of the nucleobases, nucleosides, and/or nucleotides described herein).

Also provided herein are compositions that include a lysate of any of the microorganisms described herein. Methods for generating a lysate of a microorganism are well known in the art. For example, a lysate can be prepared using methods that include, e.g., sonication, Dounce homogenization, mortar and pestle, freeze-thaw lysis, French press, and detergent and/or lysosome lysis. In some examples, the lysate is a cell free lysate that includes proteins produced by any of the organisms described herein.

Also provided are compositions that include (i) a lysate (e.g., a cell-free lysate) of any of the microorganisms described herein and (ii) a lysate (e.g., a cell-free lysate) of another microorganism (e.g., *Ashbya gossypi* or *Corynebacterium ammoniagenes*).

Also provided are kits that include a vial or container that includes any of the compositions provided herein. In some embodiments, the kit can further include instructions for performing any of the methods described herein. In some embodiments, the kit can further include instructions for culturing the microorganism (e.g., any of the exemplary culturing methods, conditions, and/or culture media described herein). In some embodiments, the kit can further include a container including a culture medium (e.g., any of the exemplary culture media described herein) (e.g., provided as a dry composition for reconstitution or provided as a solution) and/or a container including one or more components for culturing any of the microorganisms provided herein (e.g., provided as a dry composition for reconstitution or provided as a solution), e.g., a carbon source (e.g., any of the carbon sources described herein), a nitrogen source (e.g., any of the nitrogen sources described herein), a one-carbon donor (e.g., any of the one carbon donors described herein), a nucleobase, a nucleoside, and/or a nucleotide (e.g., any of the nucleobases, nucleosides, and/or nucleotides described herein).

Culture Media

Culture medium means a fluid that includes sufficient nutrients to allow a microorganism (e.g., any of the microorganisms described herein) to grow or proliferate in vitro. Non-limiting examples of culture media, in which any of the microorganisms provided herein can be cultured in (e.g., to produce one or more of any of the purine alkaloids described herein) can include, e.g., one or more (e.g., two, three, or four) of a carbon source (e.g., any of the exemplary carbon sources described herein), a nitrogen source (e.g., any of the exemplary nitrogen sources described herein), a one-carbon donor (e.g., any of the exemplary one-carbon donors described herein), and a nucleobase (e.g., any of the exemplary nucleobases described herein), a nucleoside (e.g., any of the exemplary nucleosides described herein), and/or a nucleotide (e.g., any of the exemplary nucleotides described herein). In some embodiments, the culture medium can include one or more carbon source selected from the group of: $CO_2$, acetate, glycerol, a sugar (e.g., glucose), a hydrocarbon (e.g., methane), formic acid, or an alcohol (e.g., methanol). Additional examples of carbon sources that can be included in culture media are known in the art.

In some examples, a culture medium can include one or more (e.g., two, three, or four) nitrogen source, e.g., one or more nitrogen source selected from the group of: nitrate, ammonium, and urea. Additional examples of nitrogen sources that can be included in culture media are known in the art.

In some examples, a culture medium can include one or more (e.g., two, three, or four) one-carbon donor, e.g., one or more one-carbon donor selected from the group of: S-adenosyl-methionine, methionine, and 2-hydroxyl-4-(methylthio)butanoate. Additional examples of one-carbon donors that can be included in culture media are known in the art.

In some examples, a culture medium can include one or more (e.g., two, three, or four) nucleobase, e.g., one or more nucleobase selected from the group of adenine, guanine, xanthine, hypoxanthine, cytosine, and thymine. Additional examples of nucleobases that can be included in culture media are known in the art.

In some examples, a culture medium can include one or more (e.g., two, three, or four) nucleoside, e.g., one or more nucleoside selected from the group of adenosine, deoxyadenosine, guanosine, deoxyguanosine, S-methyluridine, thymidine, uridine, deoxyuridine, cytidine, and deoxycytidine. In some examples, the culture medium can include one or more (e.g., two, three, or four) modified nucleoside (e.g., one or both of inosine and xanthosine). Additional examples of nucleosides (e.g., modified nucleosides) that can be included in culture media are known in the art.

In some examples, a culture medium can include one or more (e.g., two, three, or four) nucleotide, e.g., one or more nucleotide selected from the group of adenine triphosphate (ATP), guanosine 5'-triphosphate (GTP), inosine monophosphate (IMP), cytidine triphosphate (CTP), and uridine-5'-triphosphate (UTP). Additional examples of nucleotides that can be included in culture media are known in the art.

In some examples, a culture medium can include, e.g., (i) one or more (e.g., two, three, or four) carbon source (e.g., any of the exemplary carbon sources described herein or known in the art), and (ii) one or more (e.g., two, three, or four) nitrogen source (e.g., any of the exemplary nitrogen sources described herein or known in the art). In some examples, a culture medium can include, e.g., (i) one or more (e.g., two, three, or four) one-carbon donor (e.g., any of the exemplary one-carbon donors described herein or known in the art), and (ii) one or more (e.g., two, three, or four) of a nucleobase (e.g., any of the exemplary nucleobases described herein or known in the art), a nucleoside (e.g., any of the exemplary nucleosides or modified nucleosides described herein or known in the art), and/or a nucleotide (e.g., any of the exemplary nucleotides described herein or known in the art).

In some examples, a culture medium can further include one or more substrate that is toxic if unmethylated (e.g., arsenic, selenium, antimony, and phenol). Additional examples of substrates that are toxic if unmethylated, that can be included in culture media, are known in the art. In some examples, a culture medium can include glycine and folic acid.

In some examples, a culture medium can include one or more (e.g., two, three, or four) of methotrexate, trimethoprim, pemetrexed, proguanil, and primethamine.

Methods for making and sterilizing a culture medium are known in the art.

Culturing the Microorganisms

Culturing means the maintenance or proliferation of a microorganism under a controlled set of physical conditions. The methods of producing one or more purine alkaloid described herein include, in part, a step of culturing any of the microorganisms provided herein in a culture medium (e.g., any of the exemplary culture media describe herein or known in the art) under conditions sufficient to produce the one or more purine alkaloid.

In some examples, the culturing include the periodic or continuous addition of a culture medium to a starting culture including a plurality of the microorganisms in an initial volume of the culture medium (also called fed-batch culturing). In other examples, the culturing can include the periodic or continuous removal of a volume of culture medium (e.g., a volume of culture medium that is substantially free of microorganisms) and the periodic or continuous addition of a substantially equal volume of culture medium (also called perfusion culturing).

As is known in the art, the culturing of any of the microorganisms provided herein can be performed using a bioreactor (e.g., a fermentor, a bioreactor, or a shaking incubator containing one or more shake flasks). As is known in the art, a fermentor or bioreactor can have an internal volume of, e.g., about 50 mL to about 200,000 L, about 150,000 L, about 100,000 L, about 50,000 L, about 10,000 L, about 8,000 L, about 6,000 L, about 5,000 L, about 4,000 L, about 3,000 L, about 2,000 L, about 1,000 L, about 900 L, about 800 L, about 700 L, about 600 L, about 500 L, about 450 L, about 400 L, about 350 L, about 300 L, about 250 L, about 200 L, about 180 L, about 160 L, about 140 L, about 120 L, about 100 L, about 80 L, about 60 L, about 50 L, about 40 L, about 30 L, about 20 L, about 15 L, about 10 L, about 8 L, about 6 L, about 4 L, about 2 L, about 1 L, about 500 mL, about 250 mL, or about 100 mL; about 100 mL to about 200,000 L, about 150,000 L, about 100,000 L, about 50,000 L, about 10,000 L, about 8,000 L, about 6,000 L, about 5,000 L, about 4,000 L, about 3,000 L, about 2,000 L, about 1,000 L, about 900 L, about 800 L, about 700 L, about 600 L, about 500 L, about 450 L, about 400 L, about 350 L, about 300 L, about 250 L, about 200 L, about 180 L, about 160 L, about 140 L, about 120 L, about 100 L, about 80 L, about 60 L, about 50 L, about 40 L, about 30 L, about 20 L, about 15 L, about 10 L, about 8 L, about 6 L, about 4 L, about 2 L, about 1 L, about 500 mL, or about 250 mL; about 250 mL to about 200,000 L, about 150,000 L, about 100,000 L, about 50,000 L, about 10,000 L, about 8,000 L, about 6,000 L, about 5,000 L, about 4,000 L, about 3,000 L, about 2,000 L, about 1,000 L, about 900 L, about 800 L, about 700 L, about 600 L, about 500 L, about 450 L, about 400 L, about 350 L, about 300 L, about 250 L, about 200 L, about 180 L, about 160 L, about 140 L, about 120 L, about 100 L, about 80 L, about 60 L, about 50 L, about 40 L, about 30 L, about 20 L, about 15 L, about 10 L, about 8 L, about 6 L, about 4 L, about 2 L, about 1 L, or about 500 mL; about 500 mL to about 200,000 L, about 150,000 L, about 100,000 L, about 50,000 L, about 10,000 L, about 8,000 L, about 6,000 L, about 5,000 L, about 4,000 L, about 3,000 L, about 2,000 L, about 1,000 L, about 900 L, about 800 L, about 700 L, about 600 L, about 500 L, about 450 L, about 400 L, about 350 L, about 300 L, about 250 L, about 200 L, about 180 L, about 160 L, about 140 L, about 120 L, about 100 L, about 80 L, about 60 L, about 50 L, about 40 L, about 30 L, about 20 L, about 15 L, about 10 L, about 8 L, about 6 L, about 4 L, about 2 L, or about 1 L; about 1 L to about 200,000 L, about 150,000 L, about 100,000 L, about 50,000 L, about 10,000 L, about 8,000 L, about 6,000 L, about 5,000 L, about 4,000 L, about 3,000 L, about 2,000 L, about 1,000 L, about 900 L, about 800 L, about 700 L, about 600 L, about 500 L, about 450 L, about 400 L, about 350 L, about 300 L, about 250 L, about 200 L, about 180 L, about 160 L, about 140 L, about 120 L, about 100 L, about 80 L, about 60 L, about 50 L, about 40 L, about 30 L, about 20 L, about 15 L, about 10 L, about 8 L, about 6 L, or about 4 L; about 4 L to about 200,000 L, about 150,000 L, about 100,000 L, about 50,000 L, about 10,000 L, about 8,000 L, about 6,000 L, about 5,000 L, about 4,000 L, about 3,000 L, about 2,000 L, about 1,000 L, about 900 L, about 800 L, about 700 L, about 600 L, about 500 L, about 450 L, about 400 L, about 350 L, about 300 L, about 250 L, about 200 L, about 180 L, about 160 L, about 140 L, about 120 L, about 100 L, about 80 L, about 60 L, about 50 L, about 40 L, about 30 L, about 20 L, about 15 L, about 10 L, about 8 L, or about 6 L; about 6 L to about 200,000 L, about 150,000 L, about 100,000 L, about 50,000 L, about 10,000 L, about 8,000 L, about 6,000 L, about 5,000 L, about 4,000 L, about 3,000 L, about 2,000 L, about 1,000 L, about 900 L, about 800 L, about 700 L, about 600 L, about 500 L, about 450 L, about 400 L, about 350 L, about 300 L, about 250 L, about 200 L, about 180 L, about 160 L, about 140 L, about 120 L, about 100 L, about 80 L, about 60 L, about 50 L, about 40 L, about 30 L, about 20 L, about 15 L, about 10 L, or about 8 L; about 8 L to about 200,000 L, about 150,000 L, about 100,000 L, about 50,000 L, about 10,000 L, about 8,000 L, about 6,000 L, about 5,000 L, about 4,000 L, about 3,000 L, about 2,000 L, about 1,000 L, about 900 L, about 800 L, about 700 L, about 600 L, about 500 L, about 450 L, about 400 L, about 350 L, about 300 L, about 250 L, about 200 L, about 180 L, about 160 L, about 140 L, about 120 L, about 100 L, about 80 L, about 60 L, about 50 L, about 40 L, about 30 L, about 20 L, about 15 L, or about 10 L; about 10 L to about 200,000 L, about 150,000 L, about 100,000 L, about 50,000 L, about 10,000 L, about 8,000 L, about 6,000 L, about 5,000 L, about 4,000 L, about 3,000 L, about 2,000 L, about 1,000 L, about 900 L, about 800 L, about 700 L, about 600 L, about 500 L, about 450 L, about 400 L, about 350 L, about 300 L, about 250 L, about 200 L, about 180 L, about 160 L, about 140 L, about 120 L, about 100 L, about 80 L, about 60 L, about 50 L, about 40 L, about 30 L, about 20 L, or about 15 L; about 15 L to about 200,000 L, about 150,000 L, about 100,000 L, about 50,000 L, about 10,000 L, about 8,000 L, about 6,000 L, about 5,000 L, about 4,000 L, about 3,000 L, about 2,000 L, about 1,000 L, about 900 L, about 800 L, about 700 L, about 600 L, about 500 L, about 450 L, about 400 L, about 350 L, about 300 L, about 250 L, about 200 L, about 180 L, about 160 L, about 140 L, about 120 L, about 100 L, about 80 L, about 60 L, about 50 L, about 40 L, about 30 L, or about 20 L; about 20 L to about 200,000 L, about 150,000 L, about 100,000 L, about 50,000 L, about 10,000 L, about 8,000 L, about 6,000 L, about 5,000 L, about 4,000 L, about 3,000 L, about 2,000 L, about 1,000 L, about 900 L, about 800 L, about 700 L, about 600 L, about 500 L, about 450 L, about 400 L, about 350 L, about 300 L, about 250 L, about 200 L, about 180 L, about 160 L, about 140 L, about 120 L, about 100 L, about 80 L, about 60 L, about 50 L, about 40 L, or about 30 L; about 40 L to about 200,000 L, about 150,000 L, about 100,000 L, about 50,000 L, about 10,000 L, about 8,000 L, about 6,000 L, about 5,000 L, about 4,000 L, about 3,000 L, about 2,000 L, about 1,000 L, about 900 L, about 800 L, about 700 L, about 600 L, about 500 L, about 450 L, about 400 L, about 350 L, about 300 L, about 250 L, about 200 L, about 180 L, about 160 L, about 140 L, about 120 L, about 100 L, about 80 L, about 60 L, or about 50 L; about 50 L to about 200,000 L, about 150,000 L, about 100,000 L, about 50,000 L, about 10,000 L, about 8,000 L, about 6,000 L, about 5,000 L, about 4,000 L, about 3,000 L, about 2,000 L, about 1,000 L, about 900 L, about 800 L, about 700 L, about 600 L, about 500 L, about 450 L, about 400 L, about 350 L, about 300 L, about 250 L, about 200 L, about 180 L, about 160 L, about 140 L, about 120 L, about 100 L, about 80 L, or about 60 L; about 60 L to about 200,000 L, about 150,000 L, about 100,000 L, about 50,000 L, about 10,000 L, about 8,000 L, about 6,000 L, about 5,000 L, about 4,000 L, about 3,000 L, about 2,000 L, about 1,000 L, about 900 L, about 800 L, about 700 L, about 600 L, about 500 L, about 450 L, about 400 L, about 350 L, about 300 L, about 250 L, about 200 L, about 180 L, about 160 L, about 140 L, about 120 L, about 100 L, or about 80 L; about 80 L to about 200,000 L, about 150,000 L, about 100,000 L, about 50,000 L, about 10,000 L, about 8,000 L, about 6,000 L, about 5,000 L, about 4,000 L, about 3,000 L, about 2,000 L, about 1,000 L, about 900 L, about 800 L, about 700 L, about 600 L, about 500 L, about 450 L, about 400 L, about 350 L, about 300 L, about 250 L, about 200 L, about 180 L, about 160 L, about 140 L, about 120 L, or about 100 L; about 100 L to about 200,000 L, about 150,000 L, about 100,000 L, about 50,000 L, about 10,000 L, about 8,000 L, about 6,000 L, about 5,000 L, about 4,000 L, about 3,000 L, about 2,000 L, about 1,000 L, about 900 L, about 800 L, about 700 L, about 600 L, about 500 L, about 450 L, about 400 L, about 350 L, about 300 L, about 250 L, about 200 L, about 180 L, about 160 L, about 140 L, or about 120 L; about 120 L to about 200,000 L, about 150,000 L, about 100,000 L, about 50,000 L, about 10,000 L, about 8,000 L, about 6,000 L, about 5,000 L, about 4,000 L, about 3,000 L, about 2,000 L, about 1,000 L, about 900 L, about 800 L, about 700 L, about 600 L, about 500 L, about 450 L, about 400 L, about 350 L, about 300 L, about 250 L, about 200 L, about 180 L, about 160 L, or about 140 L; about 140 L to about 200,000 L, about 150,000 L, about 100,000 L, about 50,000 L, about 10,000 L, about 8,000 L, about 6,000 L, about 5,000 L, about 4,000 L, about 3,000 L, about 2,000 L, about 1,000 L, about 900 L, about 800 L, about 700 L, about 600 L, about 500 L, about 450 L, about 400 L, about 350 L, about 300 L, about 250 L, about 200 L, about 180 L, or about 160 L; about 160 L to about 200,000 L, about 150,000 L, about 100,000 L, about 50,000 L, about 10,000 L, about 8,000 L, about 6,000 L, about 5,000 L, about 4,000 L, about 3,000 L, about 2,000 L, about 1,000 L, about 900 L, about 800 L, about 700 L, about 600 L, about 500 L, about 450 L, about 400 L, about 350 L, about 300 L, about 250 L, about 200 L, or about 180 L; about 180 L to about 200,000 L, about 150,000 L, about 100,000 L, about 50,000 L, about 10,000 L, about 8,000 L, about 6,000 L, about 5,000 L, about 4,000 L, about 3,000 L, about 2,000 L, about 1,000 L, about 900 L, about 800 L, about 700 L, about 600 L, about 500 L, about 450 L, about 400 L, about 350 L, about 300 L, about 250 L, or about 200 L; about 200 L to about 200,000 L, about 150,000 L, about 100,000 L, about 50,000 L, about 10,000 L, about 8,000 L, about 6,000 L, about 5,000 L, about 4,000 L, about 3,000 L, about 2,000 L, about 1,000 L, about 900 L, about 800 L, about 700 L, about 600 L, about 500 L, about 450 L, about 400 L, about 350 L, about 300 L, or about 250 L; about 250 L to about 200,000 L, about 150,000 L, about 100,000 L, about 50,000 L, about 10,000 L, about 8,000 L, about 6,000 L, about 5,000 L, about 4,000 L, about 3,000 L, about 2,000 L, about 1,000 L, about 900 L, about 800 L, about 700 L, about 600 L, about 500 L, about 450 L, about 400 L, about 350 L, or about 300 L; about 300 L to about 200,000 L, about 150,000 L, about 100,000 L, about 50,000 L, about 10,000 L, about 8,000 L, about 6,000 L, about 5,000 L, about 4,000 L, about 3,000 L, about 2,000 L, about 1,000 L, about 900 L, about 800 L, about 700 L, about 600 L, about 500 L, about 450 L, about 400 L, or about 350 L; about 350 L to about 200,000 L, about 150,000 L, about 100,000 L, about 50,000 L, about 10,000 L, about 8,000 L, about 6,000 L, about 5,000 L, about 4,000 L, about 3,000 L, about 2,000 L, about 1,000 L, about 900 L, about 800 L, about 700 L, about 600 L, about 500 L, about 450 L, or about 400 L; about 400 L to about 200,000 L, about 150,000 L, about 100,000 L, about 50,000 L, about 10,000 L, about 8,000 L, about 6,000 L, about 5,000 L, about 4,000 L, about 3,000 L, about 2,000 L, about 1,000 L, about 900 L, about 800 L, about 700 L, about 600 L, about 500 L, or about 450 L; about 450 L to about 200,000 L, about 150,000 L, about 100,000 L, about 50,000 L, about 10,000 L, about 8,000 L, about 6,000 L, about 5,000 L, about 4,000 L, about 3,000 L, about 2,000 L, about 1,000 L, about 900 L, about 800 L, about 700 L, about 600 L, or about 500 L; about 500 L to about 200,000 L, about 150,000 L, about 100,000 L, about 50,000 L, about 10,000 L, about 8,000 L, about 6,000 L, about 5,000 L, about 4,000 L, about 3,000 L, about 2,000 L, about 1,000 L, about 900 L, about 800 L, about 700 L, or about 600 L; about 600 L to about 200,000 L, about 150,000 L, about 100,000 L, about 50,000 L, about 10,000 L, about 8,000 L, about 6,000 L, about 5,000 L, about 4,000 L, about 3,000 L, about 2,000 L, about 1,000 L, about 900 L, about 800 L, or about 700 L; about 700 L to about 200,000 L, about 150,000 L, about 100,000 L, about 50,000 L, about 10,000 L, about 8,000 L, about 6,000 L, about 5,000 L, about 4,000 L, about 3,000 L, about 2,000 L, about 1,000 L, about 900 L, or about 800 L; about 800 L to about 200,000 L, about 150,000 L, about 100,000 L, about 50,000 L, about 10,000 L, about 8,000 L, about 6,000 L, about 5,000 L, about 4,000 L, about 3,000 L, about 2,000 L, about 1,000 L, or about 900 L; about 900 L to about 200,000 L, about 150,000 L, about 100,000 L, about 50,000 L, about 10,000 L, about 8,000 L, about 6,000 L, about 5,000 L, about 4,000 L, about 3,000 L, about 2,000 L, or about 1,000 L; about 1,000 L to about 200,000 L, about 150,000 L, about 100,000 L, about 50,000 L, about 10,000 L, about 8,000 L, about 6,000 L, about 5,000 L, about 4,000 L, about 3,000 L, or about 2,000 L; about 2,000 L to about 200,000 L, about 150,000 L, about 100,000 L, about 50,000 L, about 10,000 L, about 8,000 L, about 6,000 L, about 5,000 L, about 4,000 L, or about 3,000 L; about 3,000 L to about 200,000 L, about 150,000 L, about 100,000 L, about 50,000 L, about 10,000 L, about 8,000 L, about 6,000 L, about 5,000 L, or about 4,000 L; about 4,000 L to about 200,000 L, about 150,000 L, about 100,000 L, about 50,000 L, about 10,000 L, about 8,000 L, about 6,000 L, or about 5,000 L; about 5,000 L to about 200,000 L, about 150,000 L, about 100,000 L, about 50,000 L, about 10,000 L, about 8,000 L, or about 6,000 L; about 6,000 L to about 10,000 L or about 8,000 L; about 8,000 L to about 200,000 L, about 150,000 L, about 100,000 L, about 50,000 L, or about 10,000 L; about 10,000 L to about 200,000 L, about 150,000 L, about 100,000 L, or about 50,000 L; about 50,000 L to about 200,000 L, about 150,000 L, or about 100,000 L; about 100,000 L to about 200,000 L, or about 150,000 L; or about 150,000 L to about 200,000 L.

The volume of a culture medium (e.g., any of the exemplary culture media described herein or known in the art) that may be disposed a bioreactor or fermentor to culture the cells can be, e.g., about 10 mL to about 150,000 L, about 125,000 L, about 100,000 L, about 80,000 L, about 60,000 L, about 40,000 L, about 20,000 L, about 10,000 L, about 8,000 L, about 7,000 L, about 6,000 L, about 5,000 L, about 4,000 L, about 3,000 L, about 2,000 L, about 1,000 L, about 900 L, about 800 L, about 700 L, about 600 L, about 500 L, about 450 L, about 400 L, about 350 L, about 300 L, about 250 L, about 200 L, about 150 L, about 100 L, about 80 L, about 60 L, about 40 L, about 20 L, about 10 L, about 5 L, about 2 L, about 1 L, about 800 mL, about 600 mL, about 400 mL, about 200 mL, about 100 mL, or about 50 mL; about 50 mL to about 150,000 L, about 125,000 L, about 100,000 L, about 80,000 L, about 60,000 L, about 40,000 L, about 20,000 L, about 10,000 L, about 8,000 L, about 7,000 L, about 6,000 L, about 5,000 L, about 4,000 L, about 3,000 L, about 2,000 L, about 1,000 L, about 900 L, about 800 L, about 700 L, about 600 L, about 500 L, about 450 L, about 400 L, about 350 L, about 300 L, about 250 L, about 200 L, about 150 L, about 100 L, about 80 L, about 60 L, about 40 L, about 20 L, about 10 L, about 5 L, about 2 L, about 1 L, about 800 mL, about 600 mL, about 400 mL, about 200 mL, or about 100 mL; about 100 mL to about 150,000 L, about 125,000 L, about 100,000 L, about 80,000 L, about 60,000 L, about 40,000 L, about 20,000 L, about 10,000 L, about 8,000 L, about 7,000 L, about 6,000 L, about 5,000 L, about 4,000 L, about 3,000 L, about 2,000 L, about 1,000 L, about 900 L, about 800 L, about 700 L, about 600 L, about 500 L, about 450 L, about 400 L, about 350 L, about 300 L, about 250 L, about 200 L, about 150 L, about 100 L, about 80 L, about 60 L, about 40 L, about 20 L, about 10 L, about 5 L, about 2 L, about 1 L, about 800 mL, about 600 mL, about 400 mL, or about 200 mL; about 200 mL to about 150,000 L, about 125,000 L, about 100,000 L, about 80,000 L, about 60,000 L, about 40,000 L, about 20,000 L, about 10,000 L, about 8,000 L, about 7,000 L, about 6,000 L, about 5,000 L, about 4,000 L, about 3,000 L, about 2,000 L, about 1,000 L, about 900 L, about 800 L, about 700 L, about 600 L, about 500 L, about 450 L, about 400 L, about 350 L, about 300 L, about 250 L, about 200 L, about 150 L, about 100 L, about 80 L, about 60 L, about 40 L, about 20 L, about 10 L, about 5 L, about 2 L, about 1 L, about 800 mL, about 600 mL, or about 400 mL; about 400 mL to about 150,000 L, about 125,000 L, about 100,000 L, about 80,000 L, about 60,000 L, about 40,000 L, about 20,000 L, about 10,000 L, about 8,000 L, about 7,000 L, about 6,000 L, about 5,000 L, about 4,000 L, about 3,000 L, about 2,000 L, about 1,000 L, about 900 L, about 800 L, about 700 L, about 600 L, about 500 L, about 450 L, about 400 L, about 350 L, about 300 L, about 250 L, about 200 L, about 150 L, about 100 L, about 80 L, about 60 L, about 40 L, about 20 L, about 10 L, about 5 L, about 2 L, about 1 L, about 800 mL, or about 600 mL; about 600 mL to about 150,000 L, about 125,000 L, about 100,000 L, about 80,000 L, about 60,000 L, about 40,000 L, about 20,000 L, about 10,000 L, about 8,000 L, about 7,000 L, about 6,000 L, about 5,000 L, about 4,000 L, about 3,000 L, about 2,000 L, about 1,000 L, about 900 L, about 800 L, about 700 L, about 600 L, about 500 L, about 450 L, about 400 L, about 350 L, about 300 L, about 250 L, about 200 L, about 150 L, about 100 L, about 80 L, about 60 L, about 40 L, about 20 L, about 10 L, about 5 L, about 2 L, about 1 L, or about 800 mL; about 800 mL to about 150,000 L, about 125,000 L, about 100,000 L, about 80,000 L, about 60,000 L, about 40,000 L, about 20,000 L, about 10,000 L, about 8,000 L, about 7,000 L, about 6,000 L, about 5,000 L, about 4,000 L, about 3,000 L, about 2,000 L, about 1,000 L, about 900 L, about 800 L, about 700 L, about 600 L, about 500 L, about 450 L, about 400 L, about 350 L, about 300 L, about 250 L, about 200 L, about 150 L, about 100 L, about 80 L, about 60 L, about 40 L, about 20 L, about 10 L, about 5 L, about 2 L, or about 1 L; about 1 L to about 150,000 L, about 125,000 L, about 100,000 L, about 80,000 L, about 60,000 L, about 40,000 L, about 20,000 L, about 10,000 L, about 8,000 L, about 7,000 L, about 6,000 L, about 5,000 L, about 4,000 L, about 3,000 L, about 2,000 L, about 1,000 L, about 900 L, about 800 L, about 700 L, about 600 L, about 500 L, about 450 L, about 400 L, about 350 L, about 300 L, about 250 L, about 200 L, about 150 L, about 100 L, about 80 L, about 60 L, about 40 L, about 20 L, about 10 L, about 5 L, or about 2 L; about 2 L to about 150,000 L, about 125,000 L, about 100,000 L, about 80,000 L, about 60,000 L, about 40,000 L, about 20,000 L, about 10,000 L, about 8,000 L, about 7,000 L, about 6,000 L, about 5,000 L, about 4,000 L, about 3,000 L, about 2,000 L, about 1,000 L, about 900 L, about 800 L, about 700 L, about 600 L, about 500 L, about 450 L, about 400 L, about 350 L, about 300 L, about 250 L, about 200 L, about 150 L, about 100 L, about 80 L, about 60 L, about 40 L, about 20 L, about 10 L, or about 5 L; about 5 L to about 150,000 L, about 125,000 L, about 100,000 L, about 80,000 L, about 60,000 L, about 40,000 L, about 20,000 L, about 10,000 L, about 8,000 L, about 7,000 L, about 6,000 L, about 5,000 L, about 4,000 L, about 3,000 L, about 2,000 L, about 1,000 L, about 900 L, about 800 L, about 700 L, about 600 L, about 500 L, about 450 L, about 400 L, about 350 L, about 300 L, about 250 L, about 200 L, about 150 L, about 100 L, about 80 L, about 60 L, about 40 L, about 20 L, or about 10 L; about 10 L to about 150,000 L, about 125,000 L, about 100,000 L, about 80,000 L, about 60,000 L, about 40,000 L, about 20,000 L, about 10,000 L, about 8,000 L, about 7,000 L, about 6,000 L, about 5,000 L, about 4,000 L, about 3,000 L, about 2,000 L, about 1,000 L, about 900 L, about 800 L, about 700 L, about 600 L, about 500 L, about 450 L, about 400 L, about 350 L, about 300 L, about 250 L, about 200 L, about 150 L, about 100 L, about 80 L, about 60 L, about 40 L, or about 20 L; about 20 L to about 150,000 L, about 125,000 L, about 100,000 L, about 80,000 L, about 60,000 L, about 40,000 L, about 20,000 L, about 10,000 L, about 8,000 L, about 7,000 L, about 6,000 L, about 5,000 L, about 4,000 L, about 3,000 L, about 2,000 L, about 1,000 L, about 900 L, about 800 L, about 700 L, about 600 L, about 500 L, about 450 L, about 400 L, about 350 L, about 300 L, about 250 L, about 200 L, about 150 L, about 100 L, about 80 L, about 60 L, or about 40 L; about 40 L to about 150,000 L, about 125,000 L, about 100,000 L, about 80,000 L, about 60,000 L, about 40,000 L, about 20,000 L, about 10,000 L, about 8,000 L, about 7,000 L, about 6,000 L, about 5,000 L, about 4,000 L, about 3,000 L, about 2,000 L, about 1,000 L, about 900 L, about 800 L, about 700 L, about 600 L, about 500 L, about 450 L, about 400 L, about 350 L, about 300 L, about 250 L, about 200 L, about 150 L, about 100 L, about 80 L, or about 60 L; about 60 L to about 150,000 L, about 125,000 L, about 100,000 L, about 80,000 L, about 60,000 L, about 40,000 L, about 20,000 L, about 10,000 L, about 8,000 L, about 7,000 L, about 6,000 L, about 5,000 L, about 4,000 L, about 3,000 L, about 2,000 L, about 1,000 L, about 900 L, about 800 L, about 700 L, about 600 L, about 500 L, about 450 L, about 400 L, about 350 L, about 300 L, about 250 L, about 200 L, about 150 L, about 100 L, or about 80 L; about 80 L to about 150,000 L, about 125,000 L, about 100,000 L, about 80,000 L, about 60,000 L, about 40,000 L, about 20,000 L, about 10,000 L, about 8,000 L, about 7,000 L, about 6,000 L, about 5,000 L, about 4,000 L, about 3,000 L, about 2,000 L, about 1,000 L, about 900 L, about 800 L, about 700 L, about 600 L, about 500 L, about 450 L, about 400 L, about 350 L, about 300 L, about 250 L, about 200 L, about 150 L, about 100 L; about 100 L to about 150,000 L, about 125,000 L, about 100,000 L, about 80,000 L, about 60,000 L, about 40,000 L, about 20,000 L, about 10,000 L, about 8,000 L, about 7,000 L, about 6,000 L, about 5,000 L, about 4,000 L, about 3,000 L, about 2,000 L, about 1,000 L, about 900 L, about 800 L, about 700 L, about 600 L, about 500 L, about 450 L, about 400 L, about 350 L, about 300 L, about 250 L, about 200 L, or about 150 L; about 150 L to about 8,000 L, about 7,000 L, about 6,000 L, about 5,000 L, about 4,000 L, about 3,000 L, about 2,000 L, about 1,000 L, about 900 L, about 800 L, about 700 L, about 600 L, about 500 L, about 450 L, about 400 L, about 350 L, about 300 L, about 250 L, or about 200 L; about 200 L to about 150,000 L, about 125,000 L, about 100,000 L, about 80,000 L, about 60,000 L, about 40,000 L, about 20,000 L, about 10,000 L, about 8,000 L, about 7,000 L, about 6,000 L, about 5,000 L, about 4,000 L, about 3,000 L, about 2,000 L, about 1,000 L, about 900 L, about 800 L, about 700 L, about 600 L, about 500 L, about 450 L, about 400 L, about 350 L, about 300 L, or about 250 L; about 250 L to about 150,000 L, about 125,000 L, about 100,000 L, about 80,000 L, about 60,000 L, about 40,000 L, about 20,000 L, about 10,000 L, about 8,000 L, about 7,000 L, about 6,000 L, about 5,000 L, about 4,000 L, about 3,000 L, about 2,000 L, about 1,000 L, about 900 L, about 800 L, about 700 L, about 600 L, about 500 L, about 450 L, about 400 L, about 350 L, or about 300 L; about 300 L to about 150,000 L, about 125,000 L, about 100,000 L, about 80,000 L, about 60,000 L, about 40,000 L, about 20,000 L, about 10,000 L, about 8,000 L, about 7,000 L, about 6,000 L, about 5,000 L, about 4,000 L, about 3,000 L, about 2,000 L, about 1,000 L, about 900 L, about 800 L, about 700 L, about 600 L, about 500 L, about 450 L, about 400 L, or about 350 L; about 350 L to about 150,000 L, about 125,000 L, about 100,000 L, about 80,000 L, about 60,000 L, about 40,000 L, about 20,000 L, about 10,000 L, about 8,000 L, about 7,000 L, about 6,000 L, about 5,000 L, about 4,000 L, about 3,000 L, about 2,000 L, about 1,000 L, about 900 L, about 800 L, about 700 L, about 600 L, about 500 L, about 450 L, or about 400 L; about 400 L to about 150,000 L, about 125,000 L, about 100,000 L, about 80,000 L, about 60,000 L, about 40,000 L, about 20,000 L, about 10,000 L, about 8,000 L, about 7,000 L, about 6,000 L, about 5,000 L, about 4,000 L, about 3,000 L, about 2,000 L, about 1,000 L, about 900 L, about 800 L, about 700 L, about 600 L, about 500 L, or about 450 L; about 450 L to about 150,000 L, about 125,000 L, about 100,000 L, about 80,000 L, about 60,000 L, about 40,000 L, about 20,000 L, about 10,000 L, about 8,000 L, about 7,000 L, about 6,000 L, about 5,000 L, about 4,000 L, about 3,000 L, about 2,000 L, about 1,000 L, about 900 L, about 800 L, about 700 L, about 600 L, or about 500 L; about 500 L to about 150,000 L, about 125,000 L, about 100,000 L, about 80,000 L, about 60,000 L, about 40,000 L, about 20,000 L, about 10,000 L, about 8,000 L, about 7,000 L, about 6,000 L, about 5,000 L, about 4,000 L, about 3,000 L, about 2,000 L, about 1,000 L, about 900 L, about 800 L, about 700 L, or about 600 L; about 600 L to about 8,000 L, about 7,000 L, about 6,000 L, about 5,000 L, about 4,000 L, about 3,000 L, about 2,000 L, about 1,000 L, about 900 L, about 800 L, or about 700 L; about 700 L to about 150,000 L, about 125,000 L, about 100,000 L, about 80,000 L, about 60,000 L, about 40,000 L, about 20,000 L, about 10,000 L, about 8,000 L, about 7,000 L, about 6,000 L, about 5,000 L, about 4,000 L, about 3,000 L, about 2,000 L, about 1,000 L, about 900 L, or about 800 L; about 800 L to about 150,000 L, about 125,000 L, about 100,000 L, about 80,000 L, about 60,000 L, about 40,000 L, about 20,000 L, about 10,000 L, about 8,000 L, about 7,000 L, about 6,000 L, about 5,000 L, about 4,000 L, about 3,000 L, about 2,000 L, about 1,000 L, or about 900 L; about 900 L to about 150,000 L, about 125,000 L, about 100,000 L, about 80,000 L, about 60,000 L, about 40,000 L, about 20,000 L, about 10,000 L, about 8,000 L, about 7,000 L, about 6,000 L, about 5,000 L, about 4,000 L, about 3,000 L, about 2,000 L, or about 1,000 L; about 1,000 L to about 150,000 L, about 125,000 L, about 100,000 L, about 80,000 L, about 60,000 L, about 40,000 L, about 20,000 L, about 10,000 L, about 8,000 L, about 7,000 L, about 6,000 L, about 5,000 L, about 4,000 L, about 3,000 L, or about 2,000 L; about 2,000 L to about 150,000 L, about 125,000 L, about 100,000 L, about 80,000 L, about 60,000 L, about 40,000 L, about 20,000 L, about 10,000 L, about 8,000 L, about 7,000 L, about 6,000 L, about 5,000 L, about 4,000 L, or about 3,000 L; about 3,000 L to about 150,000 L, about 125,000 L, about 100,000 L, about 80,000 L, about 60,000 L, about 40,000 L, about 20,000 L, about 10,000 L, about 8,000 L, about 7,000 L, about 6,000 L, about 5,000 L, or about 4,000 L; about 4,000 L to about 150,000 L, about 125,000 L, about 100,000 L, about 80,000 L, about 60,000 L, about 40,000 L, about 20,000 L, about 10,000 L, about 8,000 L, about 7,000 L, about 6,000 L, or about 5,000 L; about 5,000 L to about 150,000 L, about 125,000 L, about 100,000 L, about 80,000 L, about 60,000 L, about 40,000 L, about 20,000 L, about 10,000 L, about 8,000 L, about 7,000 L, or about 6,000 L; about 6,000 L to about 8,000 L or about 7,000 L; about 7,000 L to about 150,000 L, about 125,000 L, about 100,000 L, about 80,000 L, about 60,000 L, about 40,000 L, about 20,000 L, about 10,000 L, or about 8,000 L; about 10,000 L to about 150,000 L, about 125,000 L, about 100,000 L, about 80,000 L, about 60,000 L, about 40,000 L, or about 20,000 L; about 20,000 L to about 150,000 L, about 125,000 L, about 100,000 L, about 80,000 L, about 60,000 L, or about 40,000 L; about 40,000 L to about 150,000 L, about 125,000 L, about 100,000 L, about 80,000 L, or about 60,000 L; about 60,000 L to about 150,000 L, about 125,000 L, about 100,000 L, or about 80,000 L; about 80,000 L to about 150,000 L, about 125,000 L, or about 100,000 L; about 100,000 L to about 150,000 L or about 125,000 L; or about 125,000 L to about 150,000 L.

The step of culturing of any of the microorganisms provided herein can be performed at a temperature of about 15° C. to about 45° C. Skilled practitioners will appreciate that the temperature can be changed at specific time point(s) in during the culturing step, e.g., on an hourly or daily basis. For example, the temperature can be changed or shifted (e.g., increased or decreased) at about one day, two days, three days, four days, five days, six days, seven days, eight days, nine days, ten days, eleven days, twelve days, fourteen days, fifteen days, sixteen days, seventeen days, eighteen days, nineteen days, or about twenty days or more after the initial seeding of the fermentor, bioreactor, or shake flask with the microorganism (e.g., any of the microorganisms provided herein). For example, the temperature can be shifted upwards (e.g., a change of up to or about 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10, 11, 12, 13, 14, 15, 16, 17, 18, 19, or up to or about 20 degrees C.). For example, the temperature can be shifted downwards (e.g., a change of up to or about 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10, 11, 12, 13, 14, 15, 16, 17, 18, 19, or up to or about 20° C.).

The culturing step can include agitation. For example, the culture medium including the microorganism (e.g., any of the microorganisms provided herein) can be agitated (e.g., using rotary agitation) at a speed sufficient to accomplish mixing and/or aeration of the culture medium. In some embodiments, the culture medium including the microorganism can be agitated (e.g., using rotary agitation) at a rate of, e.g., about 15 RPM to about 400 RPM, about 380 RPM, about 360 RPM, about 340 RPM, about 320 RPM, about 300 RPM, about 280 RPM, about 260 RPM, about 240 RPM, about 220 RPM, about 200 RPM, about 180 RPM, about 160 RPM, about 140 RPM, about 120 RPM, about 100 RPM, about 80 RPM, about 60 RPM, about 40 RPM, or about 20 RPM; about 20 RPM to about 400 RPM, about 380 RPM, about 360 RPM, about 340 RPM, about 320 RPM, about 300 RPM, about 280 RPM, about 260 RPM, about 240 RPM, about 220 RPM, about 200 RPM, about 180 RPM, about 160 RPM, about 140 RPM, about 120 RPM, about 100 RPM, about 80 RPM, about 60 RPM, or about 40 RPM; about 40 RPM to about 400 RPM, about 380 RPM, about 360 RPM, about 340 RPM, about 320 RPM, about 300 RPM, about 280 RPM, about 260 RPM, about 240 RPM, about 220 RPM, about 200 RPM, about 180 RPM, about 160 RPM, about 140 RPM, about 120 RPM, about 100 RPM, about 80 RPM, or about 60 RPM; about 60 RPM to about 400 RPM, about 380 RPM, about 360 RPM, about 340 RPM, about 320 RPM, about 300 RPM, about 280 RPM, about 260 RPM, about 240 RPM, about 220 RPM, about 200 RPM, about 180 RPM, about 160 RPM, about 140 RPM, about 120 RPM, about 100 RPM, or about 80 RPM; about 80 RPM to about 400 RPM, about 380 RPM, about 360 RPM, about 340 RPM, about 320 RPM, about 300 RPM, about 280 RPM, about 260 RPM, about 240 RPM, about 220 RPM, about 200 RPM, about 180 RPM, about 160 RPM, about 140 RPM, about 120 RPM, or about 100 RPM; about 100 RPM to about 400 RPM, about 380 RPM, about 360 RPM, about 340 RPM, about 320 RPM, about 300 RPM, about 280 RPM, about 260 RPM, about 240 RPM, about 220 RPM, about 200 RPM, about 180 RPM, about 160 RPM, about 140 RPM, or about 120 RPM; about 120 RPM to about 400 RPM, about 380 RPM, about 360 RPM, about 340 RPM, about 320 RPM, about 300 RPM, about 280 RPM, about 260 RPM, about 240 RPM, about 220 RPM, about 200 RPM, about 180 RPM, about 160 RPM, about 140 RPM; about 140 RPM to about 400 RPM, about 380 RPM, about 360 RPM, about 340 RPM, about 320 RPM, about 300 RPM, about 280 RPM, about 260 RPM, about 240 RPM, about 220 RPM, about 200 RPM, about 180 RPM, or about 160 RPM; about 160 RPM to about 400 RPM, about 380 RPM, about 360 RPM, about 340 RPM, about 320 RPM, about 300 RPM, about 280 RPM, about 260 RPM, about 240 RPM, about 220 RPM, about 200 RPM, or about 180 RPM; about 180 RPM to about 400 RPM, about 380 RPM, about 360 RPM, about 340 RPM, about 320 RPM, about 300 RPM, about 280 RPM, about 260 RPM, about 240 RPM, about 220 RPM, or about 200 RPM; about 200 RPM to about 400 RPM, about 380 RPM, about 360 RPM, about 340 RPM, about 320 RPM, about 300 RPM, about 280 RPM, about 260 RPM, about 240 RPM, or about 220 RPM; about 220 RPM to about 400 RPM, about 380 RPM, about 360 RPM, about 340 RPM, about 320 RPM, about 300 RPM, about 280 RPM, about 260 RPM, or about 240 RPM; about 240 RPM to about 400 RPM, about 380 RPM, about 360 RPM, about 340 RPM, about 320 RPM, about 300 RPM, about 280 RPM, or about 260 RPM; about 260 RPM to about 400 RPM, about 380 RPM, about 360 RPM, about 340 RPM, about 320 RPM, about 300 RPM, or about 280 RPM; about 280 RPM to about 400 RPM, about 380 RPM, about 360 RPM, about 340 RPM, about 320 RPM, or about 300 RPM; about 300 RPM to about 400 RPM, about 380 RPM, about 360 RPM, about 340 RPM, or about 320 RPM; about 320 RPM to about 400 RPM, about 380 RPM, about 360 RPM, or about 340 RPM; about 340 RPM to about 400 RPM, about 380 RPM, or about 360 RPM; about 360 RPM to about 400 RPM or about 380 RPM; or about 380 RPM to about 400 RPM.

The culturing step can be performed for a period of about 2 hours to about 30 days, about 28 days, about 26 days, about 24 days, about 22 days, about 20 days, about 18 days, about 16 days, about 14 days, about 12 days, about 10 days, about 8 days, about 6 days, about 4 days, about 2 days, about 1 day, about 20 hours, about 16 hours, about 12 hours, about 8 hours, or about 4 hours; about 4 hours to about 30 days, about 28 days, about 26 days, about 24 days, about 22 days, about 20 days, about 18 days, about 16 days, about 14 days, about 12 days, about 10 days, about 8 days, about 6 days, about 4 days, about 2 days, about 1 day, about 20 hours, about 16 hours, about 12 hours, or about 8 hours; about 8 hours to about 30 days, about 28 days, about 26 days, about 24 days, about 22 days, about 20 days, about 18 days, about 16 days, about 14 days, about 12 days, about 10 days, about 8 days, about 6 days, about 4 days, about 2 days, about 1 day, about 20 hours, about 16 hours, or about 12 hours; about 12 hours to about 30 days, about 28 days, about 26 days, about 24 days, about 22 days, about 20 days, about 18 days, about 16 days, about 14 days, about 12 days, about 10 days, about 8 days, about 6 days, about 4 days, about 2 days, about 1 day, about 20 hours, or about 16 hours; about 16 hours to about 30 days, about 28 days, about 26 days, about 24 days, about 22 days, about 20 days, about 18 days, about 16 days, about 14 days, about 12 days, about 10 days, about 8 days, about 6 days, about 4 days, about 2 days, about 1 day, or about 20 hours; about 20 hours to about 30 days, about 28 days, about 26 days, about 24 days, about 22 days, about 20 days, about 18 days, about 16 days, about 14 days, about 12 days, about 10 days, about 8 days, about 6 days, about 4 days, about 2 days, or about 1 day; about 1 day to about 30 days, about 28 days, about 26 days, about 24 days, about 22 days, about 20 days, about 18 days, about 16 days, about 14 days, about 12 days, about 10 days, about 8 days, about 6 days, about 4 days, or about 2 days; about 2 days to about 30 days, about 28 days, about 26 days, about 24 days, about 22 days, about 20 days, about 18 days, about 16 days, about 14 days, about 12 days, about 10 days, about 8 days, about 6 days, or about 4 days; about 4 days to about 30 days, about 28 days, about 26 days, about 24 days, about 22 days, about 20 days, about 18 days, about 16 days, about 14 days, about 12 days, about 10 days, about 8 days, or about 6 days; about 6 days to about 30 days, about 28 days, about 26 days, about 24 days, about 22 days, about 20 days, about 18 days, about 16 days, about 14 days, about 12 days, about 10 days, or about 8 days; about 8 days to about 30 days, about 28 days, about 26 days, about 24 days, about 22 days, about 20 days, about 18 days, about 16 days, about 14 days, about 12 days, or about 10 days; about 10 days to about 30 days, about 28 days, about 26 days, about 24 days, about 22 days, about 20 days, about 18 days, about 16 days, about 14 days, or about 12 days; about 12 days to about 30 days, about 28 days, about 26 days, about 24 days, about 22 days, about 20 days, about 18 days, about 16 days, or about 14 days; about 14 days to about 30 days, about 28 days, about 26 days, about 24 days, about 22 days, about 20 days, about 18 days, or about 16 days; about 16 days to about 30 days, about 28 days, about 26 days, about 24 days, about 22 days, about 20 days, or about 18 days; about 18 days to about 30 days, about 28 days, about 26 days, about 24 days, about 22 days, or about 20 days; about 20 days to about 30 days, about 28 days, about 26 days, about 24 days, or about 22 days; about 22 days to about 30 days, about 28 days, about 26 days, or about 24 days; about 24 days to about 30 days, about 28 days, or about 26 days; about 26 days to about 30 days or about 28 days; or about 28 days to about 30 days.

Methods of Producing One or More Purine Alkaloids

Also provided herein are methods of producing one or more purine alkaloid that include culturing any of the microorganisms described herein in a culture medium (e.g., any of the culture media described herein) under conditions sufficient to produce the one or more purine alkaloid (e.g., any of the exemplary conditions described herein), and harvesting the one or more purine alkaloid. In some examples, the one or more purine alkaloid is harvested from the culture medium. In other methods, the one or more purine alkaloid is harvested from the microorganism (e.g., the cytosol of the microorganism). In some examples, the culture medium includes (i) a one-carbon donor (e.g., any of the one carbon donors described herein), and (ii) a nucleobase, a nucleoside, or a nucleotide (e.g., any of the exemplary nucleobases, nucleosides, or nucleotides described herein). In some examples, the culture medium includes (i) a carbon source (e.g., any of the carbon sources described herein), and (ii) a nitrogen source (e.g., any of the nitrogen sources described herein). In some embodiments, the one or more purine alkaloid produced is selected from the group of paraxanthine, theobromine, caffeine, theophylline, and theacrine.

It would be appreciated by a skilled artisan that the conditions under which a microorganism is cultured will be dependent upon the particular background of the microorganism as well as the combination of endogenous and heterologous nucleic acids that are functionally expressed by the microorganism.

In some examples, the culturing results in the production of a culture medium including a total concentration of at least 0.01 mg/mL, at least 0.05 mg/mL, at least 0.1 mg/mL, at least 0.15 mg/mL, at least 0.2 mg/mL, at least 0.25 mg/mL, at least 0.3 mg/mL, at least 0.35 mg/mL, at least 0.4 mg/mL, at least 0.45 mg/mL, at least 0.5 mg/mL, at least 0.55 mg/mL, at least 0.6 mg/mL, at least 0.65 mg/mL, at least 0.7 mg/mL, at least 0.75 mg/mL, at least 0.80 mg/mL, at least 0.85 mg/mL, at least 0.90 mg/mL, at least 0.95 mg/mL, at least 1.0 mg/mL, at least 1.05 mg/mL, at least 1.10 mg/mL, at least 1.15 mg/mL, at least 1.2 mg/mL, at least 1.25 mg/mL, at least 1.30 mg/mL, at least 1.35 mg/mL, at least 1.4 mg/mL, at least 1.45 mg/mL, at least 1.5 mg/mL, at least 1.6 mg/mL, at least 1.7 mg/mL, at least 1.8 mg/mL, at least 1.9 mg/mL, at least 2.0 mg/mL, at least 2.1 mg/mL, at least 2.2 mg/mL, at least 2.3 mg/mL, at least 2.4 mg/mL, at least 2.5 mg/mL, at least 2.6 mg/mL, at least 2.7 mg/mL, at least 2.8 mg/mL, at least 2.9 mg/mL, at least 3.0 mg/mL, at least 3.1 mg/mL, at least 3.2 mg/mL, at least 3.3 mg/mL, at least 3.4 mg/mL, at least 3.5 mg/mL, at least 3.6 mg/mL, at least 3.7 mg/mL, at least 3.8 mg/mL, at least 3.9 mg/mL, at least 4.0 mg/mL, at least 4.1 mg/mL, at least 4.2 mg/mL, at least 4.3 mg/mL, at least 4.4 mg/mL, at least 4.5 mg/mL, at least 4.6 mg/mL, at least 4.7 mg/mL, at least 4.8 mg/mL, at least 4.9 mg/mL, at least 5.0 mg/mL, at least 5.5 mg/mL, at least 6.0 mg/mL, at least 6.5 mg/mL, at least 7.0 mg/mL, at least 7.5 mg/mL, at least 8.0 mg/mL, at least 8.5 mg/mL, at least 9.0 mg/mL, at least 9.5 mg/mL, at least 10.0 mg/mL, at least 12 mg/mL, at least 14 mg/mL, at least 16 mg/mL, at least 18 mg/mL, at least 20 mg/mL, at least 22 mg/mL, at least 24 mg/mL, at least 26 mg/mL, at least 28 mg/mL, at least 30 mg/mL, at least 32 mg/mL, at least 34 mg/mL, at least 36 mg/mL, at least 38 mg/mL, at least 40 mg/mL, at least 42 mg/mL, at least 44 mg/mL, at least 46 mg/mL, at least 48 mg/mL, at least 50 mg/mL, at least 52 mg/mL, at least 54 mg/mL, at least 56 mg/mL, at least 58 mg/mL or at least 60 mg/mL of the purine alkaloid (or each of two or more purine alkaloids in examples where two or more purine alkaloids are produced).

In some examples, the culturing results in the production of a culture medium including a total concentration of about 0.01 mg to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, about 3.4 mg/mL, about 3.3 mg/mL, about 3.2 mg/mL, about 3.1 mg/mL, about 3.0 mg/mL, about 2.9 mg/mL, about 2.8 mg/mL, about 2.7 mg/mL, about 2.6 mg/mL, about 2.5 mg/mL, about 2.4 mg/mL, about 2.3 mg/mL, about 2.2 mg/mL, about 2.1 mg/mL, about 2.0 mg/mL, about 1.9 mg/mL, about 1.8 mg/mL, about 1.7 mg/mL, about 1.6 mg/mL, about 1.5 mg/mL, about 1.45 mg/mL, about 1.4 mg/mL, about 1.35 mg/mL, about 1.3 mg/mL, about 1.25 mg/mL, about 1.2 mg/mL, about 1.15 mg/mL, about 1.1 mg/mL, about 1.05 mg/mL, about 1.0 mg/mL, about 0.95 mg/mL, about 0.9 mg/mL, about 0.85 mg/mL, about 0.8 mg/mL, about 0.75 mg/mL, about 0.7 mg/mL, about 0.65 mg/mL, about 0.6 mg/mL, about 0.55 mg/mL, about 0.5 mg/mL, about 0.45 mg/mL, about 0.4 mg/mL, about 0.35 mg/mL, about 0.3 mg/mL, about 0.25 mg/mL, about 0.2 mg/mL, about 0.15 mg/mL, about 0.10 mg/mL, or about 0.05 mg/mL; about 0.05 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, about 3.4 mg/mL, about 3.3 mg/mL, about 3.2 mg/mL, about 3.1 mg/mL, about 3.0 mg/mL, about 2.9 mg/mL, about 2.8 mg/mL, about 2.7 mg/mL, about 2.6 mg/mL, about 2.5 mg/mL, about 2.4 mg/mL, about 2.3 mg/mL, about 2.2 mg/mL, about 2.1 mg/mL, about 2.0 mg/mL, about 1.9 mg/mL, about 1.8 mg/mL, about 1.7 mg/mL, about 1.6 mg/mL, about 1.5 mg/mL, about 1.45 mg/mL, about 1.4 mg/mL, about 1.35 mg/mL, about 1.3 mg/mL, about 1.25 mg/mL, about 1.2 mg/mL, about 1.15 mg/mL, about 1.1 mg/mL, about 1.05 mg/mL, about 1.0 mg/mL, about 0.95 mg/mL, about 0.9 mg/mL, about 0.85 mg/mL, about 0.8 mg/mL, about 0.75 mg/mL, about 0.7 mg/mL, about 0.65 mg/mL, about 0.6 mg/mL, about 0.55 mg/mL, about 0.5 mg/mL, about 0.45 mg/mL, about 0.4 mg/mL, about 0.35 mg/mL, about 0.3 mg/mL, about 0.25 mg/mL, about 0.2 mg/mL, about 0.15 mg/mL, or about 0.10 mg/mL; about 0.10 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, about 3.4 mg/mL, about 3.3 mg/mL, about 3.2 mg/mL, about 3.1 mg/mL, about 3.0 mg/mL, about 2.9 mg/mL, about 2.8 mg/mL, about 2.7 mg/mL, about 2.6 mg/mL, about 2.5 mg/mL, about 2.4 mg/mL, about 2.3 mg/mL, about 2.2 mg/mL, about 2.1 mg/mL, about 2.0 mg/mL, about 1.9 mg/mL, about 1.8 mg/mL, about 1.7 mg/mL, about 1.6 mg/mL, about 1.5 mg/mL, about 1.45 mg/mL, about 1.4 mg/mL, about 1.35 mg/mL, about 1.3 mg/mL, about 1.25 mg/mL, about 1.2 mg/mL, about 1.15 mg/mL, about 1.1 mg/mL, about 1.05 mg/mL, about 1.0 mg/mL, about 0.95 mg/mL, about 0.9 mg/mL, about 0.85 mg/mL, about 0.8 mg/mL, about 0.75 mg/mL, about 0.7 mg/mL, about 0.65 mg/mL, about 0.6 mg/mL, about 0.55 mg/mL, about 0.5 mg/mL, about 0.45 mg/mL, about 0.4 mg/mL, about 0.35 mg/mL, about 0.3 mg/mL, about 0.25 mg/mL, or about 0.2 mg/mL; about 0.2 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, about 3.4 mg/mL, about 3.3 mg/mL, about 3.2 mg/mL, about 3.1 mg/mL, about 3.0 mg/mL, about 2.9 mg/mL, about 2.8 mg/mL, about 2.7 mg/mL, about 2.6 mg/mL, about 2.5 mg/mL, about 2.4 mg/mL, about 2.3 mg/mL, about 2.2 mg/mL, about 2.1 mg/mL, about 2.0 mg/mL, about 1.9 mg/mL, about 1.8 mg/mL, about 1.7 mg/mL, about 1.6 mg/mL, about 1.5 mg/mL, about 1.45 mg/mL, about 1.4 mg/mL, about 1.35 mg/mL, about 1.3 mg/mL, about 1.25 mg/mL, about 1.2 mg/mL, about 1.15 mg/mL, about 1.1 mg/mL, about 1.05 mg/mL, about 1.0 mg/mL, about 0.95 mg/mL, about 0.9 mg/mL, about 0.85 mg/mL, about 0.8 mg/mL, about 0.75 mg/mL, about 0.7 mg/mL, about 0.65 mg/mL, about 0.6 mg/mL, about 0.55 mg/mL, about 0.5 mg/mL, about 0.45 mg/mL, about 0.4 mg/mL, about 0.35 mg/mL, about 0.3 mg/mL, or about 0.25 mg/mL; about 0.25 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, about 3.4 mg/mL, about 3.3 mg/mL, about 3.2 mg/mL, about 3.1 mg/mL, about 3.0 mg/mL, about 2.9 mg/mL, about 2.8 mg/mL, about 2.7 mg/mL, about 2.6 mg/mL, about 2.5 mg/mL, about 2.4 mg/mL, about 2.3 mg/mL, about 2.2 mg/mL, about 2.1 mg/mL, about 2.0 mg/mL, about 1.9 mg/mL, about 1.8 mg/mL, about 1.7 mg/mL, about 1.6 mg/mL, about 1.5 mg/mL, about 1.45 mg/mL, about 1.4 mg/mL, about 1.35 mg/mL, about 1.3 mg/mL, about 1.25 mg/mL, about 1.2 mg/mL, about 1.15 mg/mL, about 1.1 mg/mL, about 1.05 mg/mL, about 1.0 mg/mL, about 0.95 mg/mL, about 0.9 mg/mL, about 0.85 mg/mL, about 0.8 mg/mL, about 0.75 mg/mL, about 0.7 mg/mL, about 0.65 mg/mL, about 0.6 mg/mL, about 0.55 mg/mL, about 0.5 mg/mL, about 0.45 mg/mL, about 0.4 mg/mL, about 0.35 mg/mL, or about 0.3 mg/mL; about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 0.3 mg/mL to about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, about 3.4 mg/mL, about 3.3 mg/mL, about 3.2 mg/mL, about 3.1 mg/mL, about 3.0 mg/mL, about 2.9 mg/mL, about 2.8 mg/mL, about 2.7 mg/mL, about 2.6 mg/mL, about 2.5 mg/mL, about 2.4 mg/mL, about 2.3 mg/mL, about 2.2 mg/mL, about 2.1 mg/mL, about 2.0 mg/mL, about 1.9 mg/mL, about 1.8 mg/mL, about 1.7 mg/mL, about 1.6 mg/mL, about 1.5 mg/mL, about 1.45 mg/mL, about 1.4 mg/mL, about 1.35 mg/mL, about 1.3 mg/mL, about 1.25 mg/mL, about 1.2 mg/mL, about 1.15 mg/mL, about 1.1 mg/mL, about 1.05 mg/mL, about 1.0 mg/mL, about 0.95 mg/mL, about 0.9 mg/mL, about 0.85 mg/mL, about 0.8 mg/mL, about 0.75 mg/mL, about 0.7 mg/mL, about 0.65 mg/mL, about 0.6 mg/mL, about 0.55 mg/mL, about 0.5 mg/mL, about 0.45 mg/mL, or about 0.4 mg/mL; about 0.4 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, about 3.4 mg/mL, about 3.3 mg/mL, about 3.2 mg/mL, about 3.1 mg/mL, about 3.0 mg/mL, about 2.9 mg/mL, about 2.8 mg/mL, about 2.7 mg/mL, about 2.6 mg/mL, about 2.5 mg/mL, about 2.4 mg/mL, about 2.3 mg/mL, about 2.2 mg/mL, about 2.1 mg/mL, about 2.0 mg/mL, about 1.9 mg/mL, about 1.8 mg/mL, about 1.7 mg/mL, about 1.6 mg/mL, about 1.5 mg/mL, about 1.45 mg/mL, about 1.4 mg/mL, about 1.35 mg/mL, about 1.3 mg/mL, about 1.25 mg/mL, about 1.2 mg/mL, about 1.15 mg/mL, about 1.1 mg/mL, about 1.05 mg/mL, about 1.0 mg/mL, about 0.95 mg/mL, about 0.9 mg/mL, about 0.85 mg/mL, about 0.8 mg/mL, about 0.75 mg/mL, about 0.7 mg/mL, about 0.65 mg/mL, about 0.6 mg/mL, about 0.55 mg/mL, about 0.5 mg/mL, or about 0.45 mg/mL; about 0.45 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, about 3.4 mg/mL, about 3.3 mg/mL, about 3.2 mg/mL, about 3.1 mg/mL, about 3.0 mg/mL, about 2.9 mg/mL, about 2.8 mg/mL, about 2.7 mg/mL, about 2.6 mg/mL, about 2.5 mg/mL, about 2.4 mg/mL, about 2.3 mg/mL, about 2.2 mg/mL, about 2.1 mg/mL, about 2.0 mg/mL, about 1.9 mg/mL, about 1.8 mg/mL, about 1.7 mg/mL, about 1.6 mg/mL, about 1.5 mg/mL, about 1.45 mg/mL, about 1.4 mg/mL, about 1.35 mg/mL, about 1.3 mg/mL, about 1.25 mg/mL, about 1.2 mg/mL, about 1.15 mg/mL, about 1.1 mg/mL, about 1.05 mg/mL, about 1.0 mg/mL, about 0.95 mg/mL, about 0.9 mg/mL, about 0.85 mg/mL, about 0.8 mg/mL, about 0.75 mg/mL, about 0.7 mg/mL, about 0.65 mg/mL, about 0.6 mg/mL, about 0.55 mg/mL, or about 0.5 mg/mL; about 0.5 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, about 3.4 mg/mL, about 3.3 mg/mL, about 3.2 mg/mL, about 3.1 mg/mL, about 3.0 mg/mL, about 2.9 mg/mL, about 2.8 mg/mL, about 2.7 mg/mL, about 2.6 mg/mL, about 2.5 mg/mL, about 2.4 mg/mL, about 2.3 mg/mL, about 2.2 mg/mL, about 2.1 mg/mL, about 2.0 mg/mL, about 1.9 mg/mL, about 1.8 mg/mL, about 1.7 mg/mL, about 1.6 mg/mL, about 1.5 mg/mL, about 1.45 mg/mL, about 1.4 mg/mL, about 1.35 mg/mL, about 1.3 mg/mL, about 1.25 mg/mL, about 1.2 mg/mL, about 1.15 mg/mL, about 1.1 mg/mL, about 1.05 mg/mL, about 1.0 mg/mL, about 0.95 mg/mL, about 0.9 mg/mL, about 0.85 mg/mL, about 0.8 mg/mL, about 0.75 mg/mL, about 0.7 mg/mL, about 0.65 mg/mL, or about 0.6 mg/mL; about 0.6 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, about 3.4 mg/mL, about 3.3 mg/mL, about 3.2 mg/mL, about 3.1 mg/mL, about 3.0 mg/mL, about 2.9 mg/mL, about 2.8 mg/mL, about 2.7 mg/mL, about 2.6 mg/mL, about 2.5 mg/mL, about 2.4 mg/mL, about 2.3 mg/mL, about 2.2 mg/mL, about 2.1 mg/mL, about 2.0 mg/mL, about 1.9 mg/mL, about 1.8 mg/mL, about 1.7 mg/mL, about 1.6 mg/mL, about 1.5 mg/mL, about 1.45 mg/mL, about 1.4 mg/mL, about 1.35 mg/mL, about 1.3 mg/mL, about 1.25 mg/mL, about 1.2 mg/mL, about 1.15 mg/mL, about 1.1 mg/mL, about 1.05 mg/mL, about 1.0 mg/mL, about 0.95 mg/mL, about 0.9 mg/mL, about 0.85 mg/mL, about 0.8 mg/mL, about 0.75 mg/mL, about 0.7 mg/mL, or about 0.65 mg/mL; about 0.65 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, about 3.4 mg/mL, about 3.3 mg/mL, about 3.2 mg/mL, about 3.1 mg/mL, about 3.0 mg/mL, about 2.9 mg/mL, about 2.8 mg/mL, about 2.7 mg/mL, about 2.6 mg/mL, about 2.5 mg/mL, about 2.4 mg/mL, about 2.3 mg/mL, about 2.2 mg/mL, about 2.1 mg/mL, about 2.0 mg/mL, about 1.9 mg/mL, about 1.8 mg/mL, about 1.7 mg/mL, about 1.6 mg/mL, about 1.5 mg/mL, about 1.45 mg/mL, about 1.4 mg/mL, about 1.35 mg/mL, about 1.3 mg/mL, about 1.25 mg/mL, about 1.2 mg/mL, about 1.15 mg/mL, about 1.1 mg/mL, about 1.05 mg/mL, about 1.0 mg/mL, about 0.95 mg/mL, about 0.9 mg/mL, about 0.85 mg/mL, about 0.8 mg/mL, about 0.75 mg/mL, or about 0.7 mg/mL; about 0.7 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, about 3.4 mg/mL, about 3.3 mg/mL, about 3.2 mg/mL, about 3.1 mg/mL, about 3.0 mg/mL, about 2.9 mg/mL, about 2.8 mg/mL, about 2.7 mg/mL, about 2.6 mg/mL, about 2.5 mg/mL, about 2.4 mg/mL, about 2.3 mg/mL, about 2.2 mg/mL, about 2.1 mg/mL, about 2.0 mg/mL, about 1.9 mg/mL, about 1.8 mg/mL, about 1.7 mg/mL, about 1.6 mg/mL, about 1.5 mg/mL, about 1.45 mg/mL, about 1.4 mg/mL, about 1.35 mg/mL, about 1.3 mg/mL, about 1.25 mg/mL, about 1.2 mg/mL, about 1.15 mg/mL, about 1.1 mg/mL, about 1.05 mg/mL, about 1.0 mg/mL, about 0.95 mg/mL, about 0.9 mg/mL, about 0.85 mg/mL, about 0.8 mg/mL, or about 0.75 mg/mL; about 0.75 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, about 3.4 mg/mL, about 3.3 mg/mL, about 3.2 mg/mL, about 3.1 mg/mL, about 3.0 mg/mL, about 2.9 mg/mL, about 2.8 mg/mL, about 2.7 mg/mL, about 2.6 mg/mL, about 2.5 mg/mL, about 2.4 mg/mL, about 2.3 mg/mL, about 2.2 mg/mL, about 2.1 mg/mL, about 2.0 mg/mL, about 1.9 mg/mL, about 1.8 mg/mL, about 1.7 mg/mL, about 1.6 mg/mL, about 1.5 mg/mL, about 1.45 mg/mL, about 1.4 mg/mL, about 1.35 mg/mL, about 1.3 mg/mL, about 1.25 mg/mL, about 1.2 mg/mL, about 1.15 mg/mL, about 1.1 mg/mL, about 1.05 mg/mL, about 1.0 mg/mL, about 0.95 mg/mL, about 0.9 mg/mL, or about 0.8 mg/mL; about 0.8 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, about 3.4 mg/mL, about 3.3 mg/mL, about 3.2 mg/mL, about 3.1 mg/mL, about 3.0 mg/mL, about 2.9 mg/mL, about 2.8 mg/mL, about 2.7 mg/mL, about 2.6 mg/mL, about 2.5 mg/mL, about 2.4 mg/mL, about 2.3 mg/mL, about 2.2 mg/mL, about 2.1 mg/mL, about 2.0 mg/mL, about 1.9 mg/mL, about 1.8 mg/mL, about 1.7 mg/mL, about 1.6 mg/mL, about 1.5 mg/mL, about 1.45 mg/mL, about 1.4 mg/mL, about 1.35 mg/mL, about 1.3 mg/mL, about 1.25 mg/mL, about 1.2 mg/mL, about 1.15 mg/mL, about 1.1 mg/mL, about 1.05 mg/mL, about 1.0 mg/mL, about 0.95 mg/mL, about 0.9 mg/mL, or about 0.85 mg/mL; about 0.85 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, about 3.4 mg/mL, about 3.3 mg/mL, about 3.2 mg/mL, about 3.1 mg/mL, about 3.0 mg/mL, about 2.9 mg/mL, about 2.8 mg/mL, about 2.7 mg/mL, about 2.6 mg/mL, about 2.5 mg/mL, about 2.4 mg/mL, about 2.3 mg/mL, about 2.2 mg/mL, about 2.1 mg/mL, about 2.0 mg/mL, about 1.9 mg/mL, about 1.8 mg/mL, about 1.7 mg/mL, about 1.6 mg/mL, about 1.5 mg/mL, about 1.45 mg/mL, about 1.4 mg/mL, about 1.35 mg/mL, about 1.3 mg/mL, about 1.25 mg/mL, about 1.2 mg/mL, about 1.15 mg/mL, about 1.1 mg/mL, about 1.05 mg/mL, about 1.0 mg/mL, about 0.95 mg/mL, or about 0.9 mg/mL; about 0.9 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, about 3.4 mg/mL, about 3.3 mg/mL, about 3.2 mg/mL, about 3.1 mg/mL, about 3.0 mg/mL, about 2.9 mg/mL, about 2.8 mg/mL, about 2.7 mg/mL, about 2.6 mg/mL, about 2.5 mg/mL, about 2.4 mg/mL, about 2.3 mg/mL, about 2.2 mg/mL, about 2.1 mg/mL, about 2.0 mg/mL, about 1.9 mg/mL, about 1.8 mg/mL, about 1.7 mg/mL, about 1.6 mg/mL, about 1.5 mg/mL, about 1.45 mg/mL, about 1.4 mg/mL, about 1.35 mg/mL, about 1.3 mg/mL, about 1.25 mg/mL, about 1.2 mg/mL, about 1.15 mg/mL, about 1.1 mg/mL, about 1.05 mg/mL, about 1.0 mg/mL, or about 0.95 mg/mL; about 0.95 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, about 3.4 mg/mL, about 3.3 mg/mL, about 3.2 mg/mL, about 3.1 mg/mL, about 3.0 mg/mL, about 2.9 mg/mL, about 2.8 mg/mL, about 2.7 mg/mL, about 2.6 mg/mL, about 2.5 mg/mL, about 2.4 mg/mL, about 2.3 mg/mL, about 2.2 mg/mL, about 2.1 mg/mL, about 2.0 mg/mL, about 1.9 mg/mL, about 1.8 mg/mL, about 1.7 mg/mL, about 1.6 mg/mL, about 1.5 mg/mL, about 1.45 mg/mL, about 1.4 mg/mL, about 1.35 mg/mL, about 1.3 mg/mL, about 1.25 mg/mL, about 1.2 mg/mL, about 1.15 mg/mL, about 1.1 mg/mL, about 1.05 mg/mL, or about 1.0 mg/mL; about 1.0 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, about 3.4 mg/mL, about 3.3 mg/mL, about 3.2 mg/mL, about 3.1 mg/mL, about 3.0 mg/mL, about 2.9 mg/mL, about 2.8 mg/mL, about 2.7 mg/mL, about 2.6 mg/mL, about 2.5 mg/mL, about 2.4 mg/mL, about 2.3 mg/mL, about 2.2 mg/mL, about 2.1 mg/mL, about 2.0 mg/mL, about 1.9 mg/mL, about 1.8 mg/mL, about 1.7 mg/mL, about 1.6 mg/mL, about 1.5 mg/mL, about 1.45 mg/mL, about 1.4 mg/mL, about 1.35 mg/mL, about 1.3 mg/mL, about 1.25 mg/mL, about 1.2 mg/mL, about 1.15 mg/mL, about 1.1 mg/mL, or about 1.05 mg/mL; about 1.05 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, about 3.4 mg/mL, about 3.3 mg/mL, about 3.2 mg/mL, about 3.1 mg/mL, about 3.0 mg/mL, about 2.9 mg/mL, about 2.8 mg/mL, about 2.7 mg/mL, about 2.6 mg/mL, about 2.5 mg/mL, about 2.4 mg/mL, about 2.3 mg/mL, about 2.2 mg/mL, about 2.1 mg/mL, about 2.0 mg/mL, about 1.9 mg/mL, about 1.8 mg/mL, about 1.7 mg/mL, about 1.6 mg/mL, about 1.5 mg/mL, about 1.45 mg/mL, about 1.4 mg/mL, about 1.35 mg/mL, about 1.3 mg/mL, about 1.25 mg/mL, about 1.2 mg/mL, about 1.15 mg/mL, or about 1.1 mg/mL; about 1.1 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, about 3.4 mg/mL, about 3.3 mg/mL, about 3.2 mg/mL, about 3.1 mg/mL, about 3.0 mg/mL, about 2.9 mg/mL, about 2.8 mg/mL, about 2.7 mg/mL, about 2.6 mg/mL, about 2.5 mg/mL, about 2.4 mg/mL, about 2.3 mg/mL, about 2.2 mg/mL, about 2.1 mg/mL, about 2.0 mg/mL, about 1.9 mg/mL, about 1.8 mg/mL, about 1.7 mg/mL, about 1.6 mg/mL, about 1.5 mg/mL, about 1.45 mg/mL, about 1.4 mg/mL, about 1.35 mg/mL, about 1.3 mg/mL, about 1.25 mg/mL, about 1.2 mg/mL, or about 1.15 mg/mL; about 1.15 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, about 3.4 mg/mL, about 3.3 mg/mL, about 3.2 mg/mL, about 3.1 mg/mL, about 3.0 mg/mL, about 2.9 mg/mL, about 2.8 mg/mL, about 2.7 mg/mL, about 2.6 mg/mL, about 2.5 mg/mL, about 2.4 mg/mL, about 2.3 mg/mL, about 2.2 mg/mL, about 2.1 mg/mL, about 2.0 mg/mL, about 1.9 mg/mL, about 1.8 mg/mL, about 1.7 mg/mL, about 1.6 mg/mL, about 1.5 mg/mL, about 1.45 mg/mL, about 1.4 mg/mL, about 1.35 mg/mL, about 1.3 mg/mL, about 1.25 mg/mL, or about 1.2 mg/mL; about 1.2 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, about 3.4 mg/mL, about 3.3 mg/mL, about 3.2 mg/mL, about 3.1 mg/mL, about 3.0 mg/mL, about 2.9 mg/mL, about 2.8 mg/mL, about 2.7 mg/mL, about 2.6 mg/mL, about 2.5 mg/mL, about 2.4 mg/mL, about 2.3 mg/mL, about 2.2 mg/mL, about 2.1 mg/mL, about 2.0 mg/mL, about 1.9 mg/mL, about 1.8 mg/mL, about 1.7 mg/mL, about 1.6 mg/mL, about 1.5 mg/mL, about 1.45 mg/mL, about 1.4 mg/mL, about 1.35 mg/mL, about 1.3 mg/mL, or about 1.25 mg/mL; about 1.25 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, about 3.4 mg/mL, about 3.3 mg/mL, about 3.2 mg/mL, about 3.1 mg/mL, about 3.0 mg/mL, about 2.9 mg/mL, about 2.8 mg/mL, about 2.7 mg/mL, about 2.6 mg/mL, about 2.5 mg/mL, about 2.4 mg/mL, about 2.3 mg/mL, about 2.2 mg/mL, about 2.1 mg/mL, about 2.0 mg/mL, about 1.9 mg/mL, about 1.8 mg/mL, about 1.7 mg/mL, about 1.6 mg/mL, about 1.5 mg/mL, about 1.45 mg/mL, about 1.4 mg/mL, about 1.35 mg/mL, or about 1.3 mg/mL; about 1.3 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, about 3.4 mg/mL, about 3.3 mg/mL, about 3.2 mg/mL, about 3.1 mg/mL, about 3.0 mg/mL, about 2.9 mg/mL, about 2.8 mg/mL, about 2.7 mg/mL, about 2.6 mg/mL, about 2.5 mg/mL, about 2.4 mg/mL, about 2.3 mg/mL, about 2.2 mg/mL, about 2.1 mg/mL, about 2.0 mg/mL, about 1.9 mg/mL, about 1.8 mg/mL, about 1.7 mg/mL, about 1.6 mg/mL, about 1.5 mg/mL, about 1.45 mg/mL, or about 1.4 mg/mL; about 1.4 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, about 3.4 mg/mL, about 3.3 mg/mL, about 3.2 mg/mL, about 3.1 mg/mL, about 3.0 mg/mL, about 2.9 mg/mL, about 2.8 mg/mL, about 2.7 mg/mL, about 2.6 mg/mL, about 2.5 mg/mL, about 2.4 mg/mL, about 2.3 mg/mL, about 2.2 mg/mL, about 2.1 mg/mL, about 2.0 mg/mL, about 1.9 mg/mL, about 1.8 mg/mL, about 1.7 mg/mL, about 1.6 mg/mL, about 1.5 mg/mL, or about 1.45 mg/mL; about 1.45 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, about 3.4 mg/mL, about 3.3 mg/mL, about 3.2 mg/mL, about 3.1 mg/mL, about 3.0 mg/mL, about 2.9 mg/mL, about 2.8 mg/mL, about 2.7 mg/mL, about 2.6 mg/mL, about 2.5 mg/mL, about 2.4 mg/mL, about 2.3 mg/mL, about 2.2 mg/mL, about 2.1 mg/mL, about 2.0 mg/mL, about 1.9 mg/mL, about 1.8 mg/mL, about 1.7 mg/mL, about 1.6 mg/mL, or about 1.5 mg/mL; about 1.5 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, about 3.4 mg/mL, about 3.3 mg/mL, about 3.2 mg/mL, about 3.1 mg/mL, about 3.0 mg/mL, about 2.9 mg/mL, about 2.8 mg/mL, about 2.7 mg/mL, about 2.6 mg/mL, about 2.5 mg/mL, about 2.4 mg/mL, about 2.3 mg/mL, about 2.2 mg/mL, about 2.1 mg/mL, about 2.0 mg/mL, about 1.9 mg/mL, about 1.8 mg/mL, about 1.7 mg/mL, or about 1.6 mg/mL; about 1.6 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, about 3.4 mg/mL, about 3.3 mg/mL, about 3.2 mg/mL, about 3.1 mg/mL, about 3.0 mg/mL, about 2.9 mg/mL, about 2.8 mg/mL, about 2.7 mg/mL, about 2.6 mg/mL, about 2.5 mg/mL, about 2.4 mg/mL, about 2.3 mg/mL, about 2.2 mg/mL, about 2.1 mg/mL, about 2.0 mg/mL, about 1.9 mg/mL, or about 1.8 mg/mL; about 1.7 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, about 3.4 mg/mL, about 3.3 mg/mL, about 3.2 mg/mL, about 3.1 mg/mL, about 3.0 mg/mL, about 2.9 mg/mL, about 2.8 mg/mL, about 2.7 mg/mL, about 2.6 mg/mL, about 2.5 mg/mL, about 2.4 mg/mL, about 2.3 mg/mL, about 2.2 mg/mL, about 2.1 mg/mL, about 2.0 mg/mL, about 1.9 mg/mL, or about 1.8 mg/mL; about 1.8 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, about 3.4 mg/mL, about 3.3 mg/mL, about 3.2 mg/mL, about 3.1 mg/mL, about 3.0 mg/mL, about 2.9 mg/mL, about 2.8 mg/mL, about 2.7 mg/mL, about 2.6 mg/mL, about 2.5 mg/mL, about 2.4 mg/mL, about 2.3 mg/mL, about 2.2 mg/mL, about 2.1 mg/mL, about 2.0 mg/mL, or about 1.9 mg/mL; about 1.9 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, about 3.4 mg/mL, about 3.3 mg/mL, about 3.2 mg/mL, about 3.1 mg/mL, about 3.0 mg/mL, about 2.9 mg/mL, about 2.8 mg/mL, about 2.7 mg/mL, about 2.6 mg/mL, about 2.5 mg/mL, about 2.4 mg/mL, about 2.3 mg/mL, about 2.2 mg/mL, about 2.1 mg/mL, or about 2.0 mg/mL; about 2.0 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, about 3.4 mg/mL, about 3.3 mg/mL, about 3.2 mg/mL, about 3.1 mg/mL, about 3.0 mg/mL, about 2.9 mg/mL, about 2.8 mg/mL, about 2.7 mg/mL, about 2.6 mg/mL, about 2.5 mg/mL, about 2.4 mg/mL, about 2.3 mg/mL, about 2.2 mg/mL, or about 2.1 mg/mL; about 2.1 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, about 3.4 mg/mL, about 3.3 mg/mL, about 3.2 mg/mL, about 3.1 mg/mL, about 3.0 mg/mL, about 2.9 mg/mL, about 2.8 mg/mL, about 2.7 mg/mL, about 2.6 mg/mL, about 2.5 mg/mL, about 2.4 mg/mL, or about 2.3 mg/mL; about 2.3 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, about 3.4 mg/mL, about 3.3 mg/mL, about 3.2 mg/mL, about 3.1 mg/mL, about 3.0 mg/mL, about 2.9 mg/mL, about 2.8 mg/mL, about 2.7 mg/mL, about 2.6 mg/mL, about 2.5 mg/mL, or about 2.4 mg/mL; about 2.4 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, about 3.4 mg/mL, about 3.3 mg/mL, about 3.2 mg/mL, about 3.1 mg/mL, about 3.0 mg/mL, about 2.9 mg/mL, about 2.8 mg/mL, about 2.7 mg/mL, about 2.6 mg/mL, or about 2.5 mg/mL; about 2.5 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, about 3.4 mg/mL, about 3.3 mg/mL, about 3.2 mg/mL, about 3.1 mg/mL, about 3.0 mg/mL, about 2.9 mg/mL, about 2.8 mg/mL, about 2.7 mg/mL, or about 2.6 mg/mL; about 2.6 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, about 3.4 mg/mL, about 3.3 mg/mL, about 3.2 mg/mL, about 3.1 mg/mL, about 3.0 mg/mL, about 2.9 mg/mL, about 2.8 mg/mL, or about 2.7 mg/mL; about 2.7 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, about 3.4 mg/mL, about 3.3 mg/mL, about 3.2 mg/mL, about 3.1 mg/mL, about 3.0 mg/mL, about 2.9 mg/mL, or about 2.8 mg/mL; about 2.8 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, about 3.4 mg/mL, about 3.3 mg/mL, about 3.2 mg/mL, about 3.1 mg/mL, about 3.0 mg/mL, or about 2.9 mg/mL; about 2.9 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, about 3.4 mg/mL, about 3.3 mg/mL, about 3.2 mg/mL, about 3.1 mg/mL, or about 3.0 mg/mL; about 3.0 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, about 3.4 mg/mL, about 3.3 mg/mL, about 3.2 mg/mL, or about 3.1 mg/mL; about 3.1 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, about 3.4 mg/mL, about 3.3 mg/mL, or about 3.2 mg/mL; about 3.2 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, about 3.4 mg/mL, or about 3.3 mg/mL; about 3.3 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, or about 3.4 mg/mL; about 3.4 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, or about 3.5 mg/mL; about 3.5 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, or about 3.6 mg/mL; about 3.6 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, or about 3.7 mg/mL; about 3.7 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, or about 3.8 mg/mL; about 3.8 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 4.0 mg/mL, or about 3.9 mg/mL; about 3.9 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, or about 4.0 mg/mL; about 4.0 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, or about 4.1 mg/mL; about 4.1 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, or about 4.2 mg/mL; about 4.2 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, or about 4.3 mg/mL; about 4.3 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, or about 4.5 mg/mL; about 4.5 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, or about 4.6 mg/mL; about 4.6 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, or about 4.7 mg/mL; about 4.7 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, or about 4.8 mg/mL; about 4.8 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL or about 4.9 mg/mL; about 4.9 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, or about 5.0 mg/mL; about 5.0 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, or about 5.5 mg/mL; about 5.5 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, or about 6.0 mg/mL; about 6.0 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, or about 6.5 mg/mL; about 6.5 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, or about 7.0 mg/mL; about 7.0 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, or about 7.5 mg/mL; about 7.5 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, or about 8.5 mg/mL; about 8.5 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, or about 9.0 mg/mL; about 9.0 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, or about 9.5 mg/mL; about 9.5 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, or about 10 mg/mL; about 10 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, or about 12 mg/mL; about 12 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, or about 14 mg/mL; about 14 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, or about 16 mg/mL; about 16 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, or about 18 mg/mL; about 18 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, or about 20 mg/mL; about 20 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, or about 22 mg/mL; about 22 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, or about 24 mg/mL; about 24 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, or about 26 mg/mL; about 26 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, or about 28 mg/mL; about 28 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, or about 30 mg/mL; about 30 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, or about 32 mg/mL; about 32 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, or about 34 mg/mL; about 34 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, or about 36 mg/mL; about 36 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, or about 38 mg/mL; about 38 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, or about 40 mg/mL; about 40 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, or about 42 mg/mL; about 42 mg/mL to about 60 mg/mL, about 58 mg/mL, about 56 mg/mL, about 54 mg/mL, about 52 mg/mL, about 50 mg/mL, about 48 mg/mL, about 46 mg/mL, or about 44 mg/mL; about 44 mg/mL to about 60 mg/mL, about 58 mg/mL, about 56 mg/mL, about 54 mg/mL, about 52 mg/mL, about 50 mg/mL, about 48 mg/mL, or about 46 mg/mL; about 46 mg/mL to about 60 mg/mL, about 58 mg/mL, about 56 mg/mL, about 54 mg/mL, about 52 mg/mL, about 50 mg/mL, or about 48 mg/mL; about 48 mg/mL to about 60 mg/mL, about 58 mg/mL, about 56 mg/mL, about 54 mg/mL, about 52 mg/mL, or about 50 mg/mL; about 50 mg/mL to about 60 mg/mL, about 58 mg/mL, about 56 mg/mL, about 54 mg/mL, or about 52 mg/mL; about 52 mg/mL to about 60 mg/mL, about 58 mg/mL, about 56 mg/mL, or about 54 mg/mL; about 54 mg/mL to about 60 mg/mL, about 58 mg/mL, or about 56 mg/mL; about 56 mg/mL to about 60 mg/mL or about 58 mg/mL; or about 58 mg/mL to about 60 mg/mL, of the purine alkaloid (or each of two or more purine alkaloids in examples where two or more purine alkaloids are produced).

Also provided herein are methods of producing one or more purine alkaloid that include mixing a composition including a lysate (e.g., a cell-free lysate) of any of the microorganisms described herein with one or more substrate(s) to generate a mixture, and incubating the mixture under conditions sufficient to produce the one or more purine alkaloid, and harvesting the one or more purine alkaloid. Also provided are methods of producing one or more purine alkaloid that include mixing a composition including (i) a lysate (e.g., a cell-free lysate) of any of the microorganisms described herein and (ii) lysate (e.g., a cell-free lysate) of another microorganism (e.g., *Ashbya gossypi* or *Corynebacterium ammoniagenes*) with one or more substrate(s) to generate a mixture, and incubating the mixture under conditions sufficient to produce the one or more purine alkaloid, and harvesting the one or more purine alkaloid.

In some examples, the one or more substrate(s) can include a nucleobase, a nucleoside, or a nucleotide present in a plant nucleic acid hydrolysate. Methods for preparing a plant nucleic acid hydrolysate can include incubating a plant nucleic acid with one or more nucleases (e.g., a DNase) under conditions sufficient to yield a plant nucleic acid hydrolysate including a nucleobase, a nucleoside, and/or a nucleotide. Non-limiting examples of substrates that can be mixed with the lysate include one or more of: (i) a carbon source, (ii) a nitrogen source, (iii) a one-carbon donor, and (iv) a nucleobase, a nucleoside, or a nucleotide. In some examples, the one or more substrate(s) includes: (i) a one-carbon donor and (ii) a nucleobase, a nucleoside, or a nucleotide. In some examples, the one or more substrate(s) can include a nucleobase, a nucleoside, or a nucleotide present in a plant nucleic acid hydrolysate. Methods for preparing a plant nucleic acid hydrolysate can include incubating a plant nucleic acid with one or more nucleases (e.g., a DNase) under conditions sufficient to yield a plant nucleic acid hydrolysate including a nucleobase, a nucleoside, and/or a nucleotide. In some examples, the one or more substrate(s) include (i) a carbon source and (ii) a nitrogen source. For example, the carbon source can be selected from $CO_2$, acetate, glycerol, a sugar, a hydrocarbon (e.g., methane), formic acid, or an alcohol (e.g., methanol). For example the nitrogen source can be, e.g., nitrate, ammonium, or urea. In some examples, the one-carbon donor can be S-adenosyl-methionine, methionine, and 2-hydroxy-4-(methylthio) butanoate. In some examples, the nucleobase is selected from the group of adenine, guanine, cytosine, and thymine. In some examples, the nucleoside is a modified nucleoside (e.g., inosine or xanthosine). In some examples, the nucleoside is selected from the group of: adenosine, deoxyadenosine, guanosine, deoxyguanosine, S-methyluridine, thymidine, uridine, deoxyuridine, cytidine, and deoxycytidine. In some examples, the nucleotide is selected from the group of: adenine triphosphate (ATP), guanosine 5'-triphosphate (GTP), cytidine triphosphate (CTP), and uridine-5'-triphosphate (UTP). In some examples, the nucleobase, the nucleoside, or the nucleotide is a nucleobase, a nucleoside, or a nucleotide present in plant nucleic acid hydrolysate. Methods for preparing a plant nucleic acid hydrolysate can include incubating a plant nucleic acid with one or more nucleases (e.g., a DNase) under conditions sufficient to yield a plant nucleic acid hydrolysate including a nucleobase, a nucleoside, and/or a nucleotide.

In some embodiments of these methods, the one or more purine alkaloid is theobromine, caffeine, theophylline, and theacrine.

The mixture can be incubated at a temperature of about 25° C. to about 40° C. Skilled practitioners will appreciate that the temperature can be changed at specific time point(s) in during the incubating step, e.g., on an hourly or daily basis. For example, the temperature can be changed or shifted (e.g., increased or decreased) at about one day, two days, three days, four days, five days, six days, seven days, eight days, nine days, ten days, eleven days, twelve days, fourteen days, fifteen days, sixteen days, seventeen days, eighteen days, nineteen days, or about twenty days or more after the start of the incubation. For example, the temperature can be shifted upwards (e.g., a change of up to or about 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10, 11, 12, 13, 14, 15, 16, 17, 18, 19, or up to or about 20 degrees C.). For example, the temperature can be shifted downwards (e.g., a change of up to or about 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10, 11, 12, 13, 14, 15, 16, 17, 18, 19, or up to or about 20° C.).

The mixture can include a buffered solution (e.g., any of the buffered solutions described herein). For example, the mixture can have a pH of about 6.8 to about 7.8, about 7.7, about 7.6, about 7.5, about 7.4, about 7.3, about 7.2, about 7.1, about 7.0, or about 6.9; about to 6.9 to about 7.8, about 7.7, about 7.6, about 7.5, about 7.4, about 7.3, about 7.2, about 7.1, or about 7.0; about 7.0 to about 7.8, about 7.7, about 7.6, about 7.5, about 7.4, about 7.3, about 7.2, about 7.1; about 7.1 to about 7.8, about 7.7, about 7.6, about 7.5, about 7.4, about 7.3, or about 7.2; about 7.2 to about 7.8, about 7.7, about 7.6, about 7.5, about 7.4, or about 7.3; about 7.3 to about 7.8, about 7.7, about 7.6, about 7.5, or about 7.4; about 7.4 to about 7.8, about 7.7, about 7.6, or about 7.5; about 7.5 to about 7.8, about 7.7, or bout 7.6; about 7.6 to about 7.8 or about 7.7; or about 7.7 to about 7.8.

The incubating can be performed over a period of about 1 minute to about 30 days, about 28 days, about 26 days, about 24 days, about 22 days, about 20 days, about 18 days, about 16 days, about 14 days, about 12 days, about 10 days, about 9 days, about 8 days, about 7 days, about 6 days, about 5 days, about 4 days, about 3 days, about 2 days, about 36 hours, about 24 hours, about 20 hours, about 16 hours, about 12 hours, about 8 hours, about 4 hours, about 2 hours, about 1 hour, about 30 minutes, or about 15 minutes; about 15 minutes to about 30 days, about 28 days, about 26 days, about 24 days, about 22 days, about 20 days, about 18 days, about 16 days, about 14 days, about 12 days, about 10 days, about 9 days, about 8 days, about 7 days, about 6 days, about 5 days, about 4 days, about 3 days, about 2 days, about 36 hours, about 24 hours, about 20 hours, about 16 hours, about 12 hours, about 8 hours, about 4 hours, about 2 hours, about 1 hour, or about 30 minutes; about 30 minutes to about 30 days, about 28 days, about 26 days, about 24 days, about 22 days, about 20 days, about 18 days, about 16 days, about 14 days, about 12 days, about 10 days, about 9 days, about 8 days, about 7 days, about 6 days, about 5 days, about 4 days, about 3 days, about 2 days, about 36 hours, about 24 hours, about 20 hours, about 16 hours, about 12 hours, about 8 hours, about 4 hours, about 2 hours, or about 1 hour; about 1 hour to about 30 days, about 28 days, about 26 days, about 24 days, about 22 days, about 20 days, about 18 days, about 16 days, about 14 days, about 12 days, about 10 days, about 9 days, about 8 days, about 7 days, about 6 days, about 5 days, about 4 days, about 3 days, about 2 days, about 36 hours, about 24 hours, about 20 hours, about 16 hours, about 12 hours, about 8 hours, about 4 hours, to about 2 hours; about 2 hours to about 30 days, about 28 days, about 26 days, about 24 days, about 22 days, about 20 days, about 18 days, about 16 days, about 14 days, about 12 days, about 10 days, about 9 days, about 8 days, about 7 days, about 6 days, about 5 days, about 4 days, about 3 days, about 2 days, about 36 hours, about 24 hours, about 20 hours, about 16 hours, about 12 hours, about 8 hours, or about 4 hours; about 4 hours to about 30 days, about 28 days, about 26 days, about 24 days, about 22 days, about 20 days, about 18 days, about 16 days, about 14 days, about 12 days, about 10 days, about 9 days, about 8 days, about 7 days, about 6 days, about 5 days, about 4 days, about 3 days, about 2 days, about 36 hours, about 24 hours, about 20 hours, about 16 hours, about 12 hours, or about 8 hours; about 8 hours to about 30 days, about 28 days, about 26 days, about 24 days, about 22 days, about 20 days, about 18 days, about 16 days, about 14 days, about 12 days, about 10 days, about 9 days, about 8 days, about 7 days, about 6 days, about 5 days, about 4 days, about 3 days, about 2 days, about 36 hours, about 24 hours, about 20 hours, about 16 hours, or about 12 hours; about 12 hours to about 30 days, about 28 days, about 26 days, about 24 days, about 22 days, about 20 days, about 18 days, about 16 days, about 14 days, about 12 days, about 10 days, about 9 days, about 8 days, about 7 days, about 6 days, about 5 days, about 4 days, about 3 days, about 2 days, about 36 hours, about 24 hours, about 20 hours, or about 16 hours; about 16 hours to about 30 days, about 28 days, about 26 days, about 24 days, about 22 days, about 20 days, about 18 days, about 16 days, about 14 days, about 12 days, about 10 days, about 9 days, about 8 days, about 7 days, about 6 days, about 5 days, about 4 days, about 3 days, about 2 days, about 36 hours, about 24 hours, or about 20 hours; about 20 hours to about 30 days, about 28 days, about 26 days, about 24 days, about 22 days, about 20 days, about 18 days, about 16 days, about 14 days, about 12 days, about 10 days, about 9 days, about 8 days, about 7 days, about 6 days, about 5 days, about 4 days, about 3 days, about 2 days, about 36 hours, or about 24 hours; about 24 hours to about 30 days, about 28 days, about 26 days, about 24 days, about 22 days, about 20 days, about 18 days, about 16 days, about 14 days, about 12 days, about 10 days, about 9 days, about 8 days, about 7 days, about 6 days, about 5 days, about 4 days, about 3 days, about 2 days, or about 36 hours; about 36 hours to about 30 days, about 28 days, about 26 days, about 24 days, about 22 days, about 20 days, about 18 days, about 16 days, about 14 days, about 12 days, about 10 days, about 9 days, about 8 days, about 7 days, about 6 days, about 5 days, about 4 days, about 3 days, or about 2 days; about 2 days to about 30 days, about 28 days, about 26 days, about 24 days, about 22 days, about 20 days, about 18 days, about 16 days, about 14 days, about 12 days, about 10 days, about 9 days, about 8 days, about 7 days, about 6 days, about 5 days, about 4 days, or about 3 days; about 3 days to about 30 days, about 28 days, about 26 days, about 24 days, about 22 days, about 20 days, about 18 days, about 16 days, about 14 days, about 12 days, about 10 days, about 9 days, about 8 days, about 7 days, about 6 days, about 5 days, or about 4 days; about 4 days to about 30 days, about 28 days, about 26 days, about 24 days, about 22 days, about 20 days, about 18 days, about 16 days, about 14 days, about 12 days, about 10 days, about 9 days, about 8 days, about 7 days, about 6 days, or about 5 days; about 5 days to about 30 days, about 28 days, about 26 days, about 24 days, about 22 days, about 20 days, about 18 days, about 16 days, about 14 days, about 12 days, about 10 days, about 9 days, about 8 days, about 7 days, to about 6 days; about 6 days to about 30 days, about 28 days, about 26 days, about 24 days, about 22 days, about 20 days, about 18 days, about 16 days, about 14 days, about 12 days, about 10 days, about 9 days, about 8 days, to about 7 days; about 7 days to about 30 days, about 28 days, about 26 days, about 24 days, about 22 days, about 20 days, about 18 days, about 16 days, about 14 days, about 12 days, about 10 days, about 9 days, or about 8 days; about 8 days to about 30 days, about 28 days, about 26 days, about 24 days, about 22 days, about 20 days, about 18 days, about 16 days, about 14 days, about 12 days, about 10 days, or about 9 days; about 9 days to about 30 days, about 28 days, about 26 days, about 24 days, about 22 days, about 20 days, about 18 days, about 16 days, about 14 days, about 12 days, or about 10 days; about 10 days to about 30 days, about 28 days, about 26 days, about 24 days, about 22 days, about 20 days, about 18 days, about 16 days, about 14 days, or about 12 days; about 12 days to about 30 days, about 28 days, about 26 days, about 24 days, about 22 days, about 20 days, about 18 days, about 16 days, or about 14 days; about 14 days to about 30 days, about 28 days, about 26 days, about 24 days, about 22 days, about 20 days, about 18 days, or about 16 days; about 16 days to about 30 days, about 28 days, about 26 days, about 24 days, about 22 days, about 20 days, or about 18 days; about 18 days to about 30 days, about 28 days, about 26 days, about 24 days, about 22 days, or about 20 days; about 20 days to about 30 days, about 28 days, about 26 days, about 24 days, or about 22 days; about 22 days to about 30 days, about 28 days, about 26 days, or about 24 days; about 24 days to about 30 days, about 28 days or about 26 days; about 26 days to about 30 days or about 28 days; or about 28 days to about 30 days.

In some examples, the incubating results in the production of a mixture including a total concentration of at least 0.01 mg/mL, at least 0.05 mg/mL, at least 0.1 mg/mL, at least 0.15 mg/mL, at least 0.2 mg/mL, at least 0.25 mg/mL, at least 0.3 mg/mL, at least 0.35 mg/mL, at least 0.4 mg/mL, at least 0.45 mg/mL, at least 0.5 mg/mL, at least 0.55 mg/mL, at least 0.6 mg/mL, at least 0.65 mg/mL, at least 0.7 mg/mL, at least 0.75 mg/mL, at least 0.80 mg/mL, at least 0.85 mg/mL, at least 0.90 mg/mL, at least 0.95 mg/mL, at least 1.0 mg/mL, at least 1.05 mg/mL, at least 1.10 mg/mL, at least 1.15 mg/mL, at least 1.2 mg/mL, at least 1.25 mg/mL, at least 1.30 mg/mL, at least 1.35 mg/mL, at least 1.4 mg/mL, at least 1.45 mg/mL, at least 1.5 mg/mL, at least 1.6 mg/mL, at least 1.7 mg/mL, at least 1.8 mg/mL, at least 1.9 mg/mL, at least 2.0 mg/mL, at least 2.1 mg/mL, at least 2.2 mg/mL, at least 2.3 mg/mL, at least 2.4 mg/mL, at least 2.5 mg/mL, at least 2.6 mg/mL, at least 2.7 mg/mL, at least 2.8 mg/mL, at least 2.9 mg/mL, at least 3.0 mg/mL, at least 3.1 mg/mL, at least 3.2 mg/mL, at least 3.3 mg/mL, at least 3.4 mg/mL, at least 3.5 mg/mL, at least 3.6 mg/mL, at least 3.7 mg/mL, at least 3.8 mg/mL, at least 3.9 mg/mL, at least 4.0 mg/mL, at least 4.1 mg/mL, at least 4.2 mg/mL, at least 4.3 mg/mL, at least 4.4 mg/mL, at least 4.5 mg/mL, at least 4.6 mg/mL, at least 4.7 mg/mL, at least 4.8 mg/mL, at least 4.9 mg/mL, at least 5.0 mg/mL, at least 5.5 mg/mL, about 6.0 mg/mL, about 6.5 mg/mL, about 7.0 mg/mL, about 7.5 mg/mL, about 8.0 mg/mL, about 8.5 mg/mL, about 9.0 mg/mL, about 9.5 mg/mL, about 10 mg/mL, about 12 mg/mL, about 14 mg/mL, about 16 mg/mL, about 18 mg/mL, about 20 mg/mL, about 22 mg/mL, about 24 mg/mL, about 26 mg/mL, about 28 mg/mL, about 30 mg/mL, about 32 mg/mL, about 34 mg/mL, about 36 mg/mL, about 38 mg/mL, about 40 mg/mL, about 42 mg/mL, about 44 mg/mL, about 46 mg/mL, about 48 mg/mL, about 50 mg/mL, about 52 mg/mL, about 54 mg/mL, about 56 mg/mL, about 58 mg/mL or about 60 mg/mL of the purine alkaloid (or each of two or more purine alkaloids in examples where two or more purine alkaloids are produced).

In some examples, the incubating results in the production of a mixture including a total concentration of about 0.01 mg to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, about 3.4 mg/mL, about 3.3 mg/mL, about 3.2 mg/mL, about 3.1 mg/mL, about 3.0 mg/mL, about 2.9 mg/mL, about 2.8 mg/mL, about 2.7 mg/mL, about 2.6 mg/mL, about 2.5 mg/mL, about 2.4 mg/mL, about 2.3 mg/mL, about 2.2 mg/mL, about 2.1 mg/mL, about 2.0 mg/mL, about 1.9 mg/mL, about 1.8 mg/mL, about 1.7 mg/mL, about 1.6 mg/mL, about 1.5 mg/mL, about 1.45 mg/mL, about 1.4 mg/mL, about 1.35 mg/mL, about 1.3 mg/mL, about 1.25 mg/mL, about 1.2 mg/mL, about 1.15 mg/mL, about 1.1 mg/mL, about 1.05 mg/mL, about 1.0 mg/mL, about 0.95 mg/mL, about 0.9 mg/mL, about 0.85 mg/mL, about 0.8 mg/mL, about 0.75 mg/mL, about 0.7 mg/mL, about 0.65 mg/mL, about 0.6 mg/mL, about 0.55 mg/mL, about 0.5 mg/mL, about 0.45 mg/mL, about 0.4 mg/mL, about 0.35 mg/mL, about 0.3 mg/mL, about 0.25 mg/mL, about 0.2 mg/mL, about 0.15 mg/mL, about 0.10 mg/mL, or about 0.05 mg/mL; about 0.05 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, about 3.4 mg/mL, about 3.3 mg/mL, about 3.2 mg/mL, about 3.1 mg/mL, about 3.0 mg/mL, about 2.9 mg/mL, about 2.8 mg/mL, about 2.7 mg/mL, about 2.6 mg/mL, about 2.5 mg/mL, about 2.4 mg/mL, about 2.3 mg/mL, about 2.2 mg/mL, about 2.1 mg/mL, about 2.0 mg/mL, about 1.9 mg/mL, about 1.8 mg/mL, about 1.7 mg/mL, about 1.6 mg/mL, about 1.5 mg/mL, about 1.45 mg/mL, about 1.4 mg/mL, about 1.35 mg/mL, about 1.3 mg/mL, about 1.25 mg/mL, about 1.2 mg/mL, about 1.15 mg/mL, about 1.1 mg/mL, about 1.05 mg/mL, about 1.0 mg/mL, about 0.95 mg/mL, about 0.9 mg/mL, about 0.85 mg/mL, about 0.8 mg/mL, about 0.75 mg/mL, about 0.7 mg/mL, about 0.65 mg/mL, about 0.6 mg/mL, about 0.55 mg/mL, about 0.5 mg/mL, about 0.45 mg/mL, about 0.4 mg/mL, about 0.35 mg/mL, about 0.3 mg/mL, about 0.25 mg/mL, about 0.2 mg/mL, about 0.15 mg/mL, or about 0.10 mg/mL; about 0.10 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, about 3.4 mg/mL, about 3.3 mg/mL, about 3.2 mg/mL, about 3.1 mg/mL, about 3.0 mg/mL, about 2.9 mg/mL, about 2.8 mg/mL, about 2.7 mg/mL, about 2.6 mg/mL, about 2.5 mg/mL, about 2.4 mg/mL, about 2.3 mg/mL, about 2.2 mg/mL, about 2.1 mg/mL, about 2.0 mg/mL, about 1.9 mg/mL, about 1.8 mg/mL, about 1.7 mg/mL, about 1.6 mg/mL, about 1.5 mg/mL, about 1.45 mg/mL, about 1.4 mg/mL, about 1.35 mg/mL, about 1.3 mg/mL, about 1.25 mg/mL, about 1.2 mg/mL, about 1.15 mg/mL, about 1.1 mg/mL, about 1.05 mg/mL, about 1.0 mg/mL, about 0.95 mg/mL, about 0.9 mg/mL, about 0.85 mg/mL, about 0.8 mg/mL, about 0.75 mg/mL, about 0.7 mg/mL, about 0.65 mg/mL, about 0.6 mg/mL, about 0.55 mg/mL, about 0.5 mg/mL, about 0.45 mg/mL, about 0.4 mg/mL, about 0.35 mg/mL, about 0.3 mg/mL, about 0.25 mg/mL, or about 0.2 mg/mL; about 0.2 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, about 3.4 mg/mL, about 3.3 mg/mL, about 3.2 mg/mL, about 3.1 mg/mL, about 3.0 mg/mL, about 2.9 mg/mL, about 2.8 mg/mL, about 2.7 mg/mL, about 2.6 mg/mL, about 2.5 mg/mL, about 2.4 mg/mL, about 2.3 mg/mL, about 2.2 mg/mL, about 2.1 mg/mL, about 2.0 mg/mL, about 1.9 mg/mL, about 1.8 mg/mL, about 1.7 mg/mL, about 1.6 mg/mL, about 1.5 mg/mL, about 1.45 mg/mL, about 1.4 mg/mL, about 1.35 mg/mL, about 1.3 mg/mL, about 1.25 mg/mL, about 1.2 mg/mL, about 1.15 mg/mL, about 1.1 mg/mL, about 1.05 mg/mL, about 1.0 mg/mL, about 0.95 mg/mL, about 0.9 mg/mL, about 0.85 mg/mL, about 0.8 mg/mL, about 0.75 mg/mL, about 0.7 mg/mL, about 0.65 mg/mL, about 0.6 mg/mL, about 0.55 mg/mL, about 0.5 mg/mL, about 0.45 mg/mL, about 0.4 mg/mL, about 0.35 mg/mL, about 0.3 mg/mL, or about 0.25 mg/mL; about 0.25 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, about 3.4 mg/mL, about 3.3 mg/mL, about 3.2 mg/mL, about 3.1 mg/mL, about 3.0 mg/mL, about 2.9 mg/mL, about 2.8 mg/mL, about 2.7 mg/mL, about 2.6 mg/mL, about 2.5 mg/mL, about 2.4 mg/mL, about 2.3 mg/mL, about 2.2 mg/mL, about 2.1 mg/mL, about 2.0 mg/mL, about 1.9 mg/mL, about 1.8 mg/mL, about 1.7 mg/mL, about 1.6 mg/mL, about 1.5 mg/mL, about 1.45 mg/mL, about 1.4 mg/mL, about 1.35 mg/mL, about 1.3 mg/mL, about 1.25 mg/mL, about 1.2 mg/mL, about 1.15 mg/mL, about 1.1 mg/mL, about 1.05 mg/mL, about 1.0 mg/mL, about 0.95 mg/mL, about 0.9 mg/mL, about 0.85 mg/mL, about 0.8 mg/mL, about 0.75 mg/mL, about 0.7 mg/mL, about 0.65 mg/mL, about 0.6 mg/mL, about 0.55 mg/mL, about 0.5 mg/mL, about 0.45 mg/mL, about 0.4 mg/mL, about 0.35 mg/mL, or about 0.3 mg/mL; about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 0.3 mg/mL to about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, about 3.4 mg/mL, about 3.3 mg/mL, about 3.2 mg/mL, about 3.1 mg/mL, about 3.0 mg/mL, about 2.9 mg/mL, about 2.8 mg/mL, about 2.7 mg/mL, about 2.6 mg/mL, about 2.5 mg/mL, about 2.4 mg/mL, about 2.3 mg/mL, about 2.2 mg/mL, about 2.1 mg/mL, about 2.0 mg/mL, about 1.9 mg/mL, about 1.8 mg/mL, about 1.7 mg/mL, about 1.6 mg/mL, about 1.5 mg/mL, about 1.45 mg/mL, about 1.4 mg/mL, about 1.35 mg/mL, about 1.3 mg/mL, about 1.25 mg/mL, about 1.2 mg/mL, about 1.15 mg/mL, about 1.1 mg/mL, about 1.05 mg/mL, about 1.0 mg/mL, about 0.95 mg/mL, about 0.9 mg/mL, about 0.85 mg/mL, about 0.8 mg/mL, about 0.75 mg/mL, about 0.7 mg/mL, about 0.65 mg/mL, about 0.6 mg/mL, about 0.55 mg/mL, about 0.5 mg/mL, about 0.45 mg/mL, about 0.4 mg/mL, or about 0.35 mg/mL; about 0.35 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, about 3.4 mg/mL, about 3.3 mg/mL, about 3.2 mg/mL, about 3.1 mg/mL, about 3.0 mg/mL, about 2.9 mg/mL, about 2.8 mg/mL, about 2.7 mg/mL, about 2.6 mg/mL, about 2.5 mg/mL, about 2.4 mg/mL, about 2.3 mg/mL, about 2.2 mg/mL, about 2.1 mg/mL, about 2.0 mg/mL, about 1.9 mg/mL, about 1.8 mg/mL, about 1.7 mg/mL, about 1.6 mg/mL, about 1.5 mg/mL, about 1.45 mg/mL, about 1.4 mg/mL, about 1.35 mg/mL, about 1.3 mg/mL, about 1.25 mg/mL, about 1.2 mg/mL, about 1.15 mg/mL, about 1.1 mg/mL, about 1.05 mg/mL, about 1.0 mg/mL, about 0.95 mg/mL, about 0.9 mg/mL, about 0.85 mg/mL, about 0.8 mg/mL, about 0.75 mg/mL, about 0.7 mg/mL, about 0.65 mg/mL, about 0.6 mg/mL, about 0.55 mg/mL, about 0.5 mg/mL, or about 0.45 mg/mL; about 0.45 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, about 3.4 mg/mL, about 3.3 mg/mL, about 3.2 mg/mL, about 3.1 mg/mL, about 3.0 mg/mL, about 2.9 mg/mL, about 2.8 mg/mL, about 2.7 mg/mL, about 2.6 mg/mL, about 2.5 mg/mL, about 2.4 mg/mL, about 2.3 mg/mL, about 2.2 mg/mL, about 2.1 mg/mL, about 2.0 mg/mL, about 1.9 mg/mL, about 1.8 mg/mL, about 1.7 mg/mL, about 1.6 mg/mL, about 1.5 mg/mL, about 1.45 mg/mL, about 1.4 mg/mL, about 1.35 mg/mL, about 1.3 mg/mL, about 1.25 mg/mL, about 1.2 mg/mL, about 1.15 mg/mL, about 1.1 mg/mL, about 1.05 mg/mL, about 1.0 mg/mL, about 0.95 mg/mL, about 0.9 mg/mL, about 0.85 mg/mL, about 0.8 mg/mL, about 0.75 mg/mL, about 0.7 mg/mL, about 0.65 mg/mL, about 0.6 mg/mL, about 0.55 mg/mL, or about 0.5 mg/mL; about 0.5 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, about 3.4 mg/mL, about 3.3 mg/mL, about 3.2 mg/mL, about 3.1 mg/mL, about 3.0 mg/mL, about 2.9 mg/mL, about 2.8 mg/mL, about 2.7 mg/mL, about 2.6 mg/mL, about 2.5 mg/mL, about 2.4 mg/mL, about 2.3 mg/mL, about 2.2 mg/mL, about 2.1 mg/mL, about 2.0 mg/mL, about 1.9 mg/mL, about 1.8 mg/mL, about 1.7 mg/mL, about 1.6 mg/mL, about 1.5 mg/mL, about 1.45 mg/mL, about 1.4 mg/mL, about 1.35 mg/mL, about 1.3 mg/mL, about 1.25 mg/mL, about 1.2 mg/mL, about 1.15 mg/mL, about 1.1 mg/mL, about 1.05 mg/mL, about 1.0 mg/mL, about 0.95 mg/mL, about 0.9 mg/mL, about 0.85 mg/mL, about 0.8 mg/mL, about 0.75 mg/mL, about 0.7 mg/mL, about 0.65 mg/mL, about 0.6 mg/mL, or about 0.55 mg/mL; about 0.55 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, about 3.4 mg/mL, about 3.3 mg/mL, about 3.2 mg/mL, about 3.1 mg/mL, about 3.0 mg/mL, about 2.9 mg/mL, about 2.8 mg/mL, about 2.7 mg/mL, about 2.6 mg/mL, about 2.5 mg/mL, about 2.4 mg/mL, about 2.3 mg/mL, about 2.2 mg/mL, about 2.1 mg/mL, about 2.0 mg/mL, about 1.9 mg/mL, about 1.8 mg/mL, about 1.7 mg/mL, about 1.6 mg/mL, about 1.5 mg/mL, about 1.45 mg/mL, about 1.4 mg/mL, about 1.35 mg/mL, about 1.3 mg/mL, about 1.25 mg/mL, about 1.2 mg/mL, about 1.15 mg/mL, about 1.1 mg/mL, about 1.05 mg/mL, about 1.0 mg/mL, about 0.95 mg/mL, about 0.9 mg/mL, about 0.85 mg/mL, about 0.8 mg/mL, about 0.75 mg/mL, about 0.7 mg/mL, or about 0.65 mg/mL; about 0.65 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, about 3.4 mg/mL, about 3.3 mg/mL, about 3.2 mg/mL, about 3.1 mg/mL, about 3.0 mg/mL, about 2.9 mg/mL, about 2.8 mg/mL, about 2.7 mg/mL, about 2.6 mg/mL, about 2.5 mg/mL, about 2.4 mg/mL, about 2.3 mg/mL, about 2.2 mg/mL, about 2.1 mg/mL, about 2.0 mg/mL, about 1.9 mg/mL, about 1.8 mg/mL, about 1.7 mg/mL, about 1.6 mg/mL, about 1.5 mg/mL, about 1.45 mg/mL, about 1.4 mg/mL, about 1.35 mg/mL, about 1.3 mg/mL, about 1.25 mg/mL, about 1.2 mg/mL, about 1.15 mg/mL, about 1.1 mg/mL, about 1.05 mg/mL, about 1.0 mg/mL, about 0.95 mg/mL, about 0.9 mg/mL, about 0.85 mg/mL, about 0.8 mg/mL, about 0.75 mg/mL, or about 0.7 mg/mL; about 0.7 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, about 3.4 mg/mL, about 3.3 mg/mL, about 3.2 mg/mL, about 3.1 mg/mL, about 3.0 mg/mL, about 2.9 mg/mL, about 2.8 mg/mL, about 2.7 mg/mL, about 2.6 mg/mL, about 2.5 mg/mL, about 2.4 mg/mL, about 2.3 mg/mL, about 2.2 mg/mL, about 2.1 mg/mL, about 2.0 mg/mL, about 1.9 mg/mL, about 1.8 mg/mL, about 1.7 mg/mL, about 1.6 mg/mL, about 1.5 mg/mL, about 1.45 mg/mL, about 1.4 mg/mL, about 1.35 mg/mL, about 1.3 mg/mL, about 1.25 mg/mL, about 1.2 mg/mL, about 1.15 mg/mL, about 1.1 mg/mL, about 1.05 mg/mL, about 1.0 mg/mL, about 0.95 mg/mL, about 0.9 mg/mL, about 0.85 mg/mL, about 0.8 mg/mL, or about 0.75 mg/mL; about 0.75 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, about 3.4 mg/mL, about 3.3 mg/mL, about 3.2 mg/mL, about 3.1 mg/mL, about 3.0 mg/mL, about 2.9 mg/mL, about 2.8 mg/mL, about 2.7 mg/mL, about 2.6 mg/mL, about 2.5 mg/mL, about 2.4 mg/mL, about 2.3 mg/mL, about 2.2 mg/mL, about 2.1 mg/mL, about 2.0 mg/mL, about 1.9 mg/mL, about 1.8 mg/mL, about 1.7 mg/mL, about 1.6 mg/mL, about 1.5 mg/mL, about 1.45 mg/mL, about 1.4 mg/mL, about 1.35 mg/mL, about 1.3 mg/mL, about 1.25 mg/mL, about 1.2 mg/mL, about 1.15 mg/mL, about 1.1 mg/mL, about 1.05 mg/mL, about 1.0 mg/mL, about 0.95 mg/mL, about 0.9 mg/mL, about 0.85 mg/mL, or about 0.8 mg/mL; about 0.8 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, about 3.4 mg/mL, about 3.3 mg/mL, about 3.2 mg/mL, about 3.1 mg/mL, about 3.0 mg/mL, about 2.9 mg/mL, about 2.8 mg/mL, about 2.7 mg/mL, about 2.6 mg/mL, about 2.5 mg/mL, about 2.4 mg/mL, about 2.3 mg/mL, about 2.2 mg/mL, about 2.1 mg/mL, about 2.0 mg/mL, about 1.9 mg/mL, about 1.8 mg/mL, about 1.7 mg/mL, about 1.6 mg/mL, about 1.5 mg/mL, about 1.45 mg/mL, about 1.4 mg/mL, about 1.35 mg/mL, about 1.3 mg/mL, about 1.25 mg/mL, about 1.2 mg/mL, about 1.15 mg/mL, about 1.1 mg/mL, about 1.05 mg/mL, about 1.0 mg/mL, about 0.95 mg/mL, or about 0.9 mg/mL; about 0.9 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, about 3.4 mg/mL, about 3.3 mg/mL, about 3.2 mg/mL, about 3.1 mg/mL, about 3.0 mg/mL, about 2.9 mg/mL, about 2.8 mg/mL, about 2.7 mg/mL, about 2.6 mg/mL, about 2.5 mg/mL, about 2.4 mg/mL, about 2.3 mg/mL, about 2.2 mg/mL, about 2.1 mg/mL, about 2.0 mg/mL, about 1.9 mg/mL, about 1.8 mg/mL, about 1.7 mg/mL, about 1.6 mg/mL, about 1.5 mg/mL, about 1.45 mg/mL, about 1.4 mg/mL, about 1.35 mg/mL, about 1.3 mg/mL, about 1.25 mg/mL, about 1.2 mg/mL, about 1.15 mg/mL, about 1.1 mg/mL, about 1.05 mg/mL, about 1.0 mg/mL, or about 0.95 mg/mL; about 0.95 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, about 3.4 mg/mL, about 3.3 mg/mL, about 3.2 mg/mL, about 3.1 mg/mL, about 3.0 mg/mL, about 2.9 mg/mL, about 2.8 mg/mL, about 2.7 mg/mL, about 2.6 mg/mL, about 2.5 mg/mL, about 2.4 mg/mL, about 2.3 mg/mL, about 2.2 mg/mL, about 2.1 mg/mL, about 2.0 mg/mL, about 1.9 mg/mL, about 1.8 mg/mL, about 1.7 mg/mL, about 1.6 mg/mL, about 1.5 mg/mL, about 1.45 mg/mL, about 1.4 mg/mL, about 1.35 mg/mL, about 1.3 mg/mL, about 1.25 mg/mL, about 1.2 mg/mL, about 1.15 mg/mL, about 1.1 mg/mL, about 1.05 mg/mL, or about 1.0 mg/mL; about 1.0 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, about 3.4 mg/mL, about 3.3 mg/mL, about 3.2 mg/mL, about 3.1 mg/mL, about 3.0 mg/mL, about 2.9 mg/mL, about 2.8 mg/mL, about 2.7 mg/mL, about 2.6 mg/mL, about 2.5 mg/mL, about 2.4 mg/mL, about 2.3 mg/mL, about 2.2 mg/mL, about 2.1 mg/mL, about 2.0 mg/mL, about 1.9 mg/mL, about 1.8 mg/mL, about 1.7 mg/mL, about 1.6 mg/mL, about 1.5 mg/mL, about 1.45 mg/mL, about 1.4 mg/mL, about 1.35 mg/mL, about 1.3 mg/mL, about 1.25 mg/mL, about 1.2 mg/mL, about 1.15 mg/mL, about 1.1 mg/mL, or about 1.05 mg/mL; about 1.05 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, about 3.4 mg/mL, about 3.3 mg/mL, about 3.2 mg/mL, about 3.1 mg/mL, about 3.0 mg/mL, about 2.9 mg/mL, about 2.8 mg/mL, about 2.7 mg/mL, about 2.6 mg/mL, about 2.5 mg/mL, about 2.4 mg/mL, about 2.3 mg/mL, about 2.2 mg/mL, about 2.1 mg/mL, about 2.0 mg/mL, about 1.9 mg/mL, about 1.8 mg/mL, about 1.7 mg/mL, about 1.6 mg/mL, about 1.5 mg/mL, about 1.45 mg/mL, about 1.4 mg/mL, about 1.35 mg/mL, about 1.3 mg/mL, about 1.25 mg/mL, about 1.2 mg/mL, about 1.15 mg/mL, or about 1.1 mg/mL; about 1.1 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, about 3.4 mg/mL, about 3.3 mg/mL, about 3.2 mg/mL, about 3.1 mg/mL, about 3.0 mg/mL, about 2.9 mg/mL, about 2.8 mg/mL, about 2.7 mg/mL, about 2.6 mg/mL, about 2.5 mg/mL, about 2.4 mg/mL, about 2.3 mg/mL, about 2.2 mg/mL, about 2.1 mg/mL, about 2.0 mg/mL, about 1.9 mg/mL, about 1.8 mg/mL, about 1.7 mg/mL, about 1.6 mg/mL, about 1.5 mg/mL, about 1.45 mg/mL, about 1.4 mg/mL, about 1.35 mg/mL, about 1.3 mg/mL, about 1.25 mg/mL, about 1.2 mg/mL, or about 1.15 mg/mL; about 1.15 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, about 3.4 mg/mL, about 3.3 mg/mL, about 3.2 mg/mL, about 3.1 mg/mL, about 3.0 mg/mL, about 2.9 mg/mL, about 2.8 mg/mL, about 2.7 mg/mL, about 2.6 mg/mL, about 2.5 mg/mL, about 2.4 mg/mL, about 2.3 mg/mL, about 2.2 mg/mL, about 2.1 mg/mL, about 2.0 mg/mL, about 1.9 mg/mL, about 1.8 mg/mL, about 1.7 mg/mL, about 1.6 mg/mL, about 1.5 mg/mL, about 1.45 mg/mL, about 1.4 mg/mL, about 1.35 mg/mL, about 1.3 mg/mL, about 1.25 mg/mL, or about 1.2 mg/mL; about 1.2 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, about 3.4 mg/mL, about 3.3 mg/mL, about 3.2 mg/mL, about 3.1 mg/mL, about 3.0 mg/mL, about 2.9 mg/mL, about 2.8 mg/mL, about 2.7 mg/mL, about 2.6 mg/mL, about 2.5 mg/mL, about 2.4 mg/mL, about 2.3 mg/mL, about 2.2 mg/mL, about 2.1 mg/mL, about 2.0 mg/mL, about 1.9 mg/mL, about 1.8 mg/mL, about 1.7 mg/mL, about 1.6 mg/mL, about 1.5 mg/mL, about 1.45 mg/mL, about 1.4 mg/mL, about 1.35 mg/mL, about 1.3 mg/mL, or about 1.25 mg/mL; about 1.25 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, about 3.4 mg/mL, about 3.3 mg/mL, about 3.2 mg/mL, about 3.1 mg/mL, about 3.0 mg/mL, about 2.9 mg/mL, about 2.8 mg/mL, about 2.7 mg/mL, about 2.6 mg/mL, about 2.5 mg/mL, about 2.4 mg/mL, about 2.3 mg/mL, about 2.2 mg/mL, about 2.1 mg/mL, about 2.0 mg/mL, about 1.9 mg/mL, about 1.8 mg/mL, about 1.7 mg/mL, about 1.6 mg/mL, about 1.5 mg/mL, about 1.45 mg/mL, about 1.4 mg/mL, about 1.35 mg/mL, or about 1.3 mg/mL; about 1.3 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, about 3.4 mg/mL, about 3.3 mg/mL, about 3.2 mg/mL, about 3.1 mg/mL, about 3.0 mg/mL, about 2.9 mg/mL, about 2.8 mg/mL, about 2.7 mg/mL, about 2.6 mg/mL, about 2.5 mg/mL, about 2.4 mg/mL, about 2.3 mg/mL, about 2.2 mg/mL, about 2.1 mg/mL, about 2.0 mg/mL, about 1.9 mg/mL, about 1.8 mg/mL, about 1.7 mg/mL, about 1.6 mg/mL, about 1.5 mg/mL, about 1.45 mg/mL, or about 1.4 mg/mL; about 1.4 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, about 3.4 mg/mL, about 3.3 mg/mL, about 3.2 mg/mL, about 3.1 mg/mL, about 3.0 mg/mL, about 2.9 mg/mL, about 2.8 mg/mL, about 2.7 mg/mL, about 2.6 mg/mL, about 2.5 mg/mL, about 2.4 mg/mL, about 2.3 mg/mL, about 2.2 mg/mL, about 2.1 mg/mL, about 2.0 mg/mL, about 1.9 mg/mL, about 1.8 mg/mL, about 1.7 mg/mL, about 1.6 mg/mL, about 1.5 mg/mL, or about 1.45 mg/mL; about 1.45 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, about 3.4 mg/mL, about 3.3 mg/mL, about 3.2 mg/mL, about 3.1 mg/mL, about 3.0 mg/mL, about 2.9 mg/mL, about 2.8 mg/mL, about 2.7 mg/mL, about 2.6 mg/mL, about 2.5 mg/mL, about 2.4 mg/mL, about 2.3 mg/mL, about 2.2 mg/mL, about 2.1 mg/mL, about 2.0 mg/mL, about 1.9 mg/mL, about 1.8 mg/mL, about 1.7 mg/mL, about 1.6 mg/mL, or about 1.5 mg/mL; about 1.5 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, about 3.4 mg/mL, about 3.3 mg/mL, about 3.2 mg/mL, about 3.1 mg/mL, about 3.0 mg/mL, about 2.9 mg/mL, about 2.8 mg/mL, about 2.7 mg/mL, about 2.6 mg/mL, about 2.5 mg/mL, about 2.4 mg/mL, about 2.3 mg/mL, about 2.2 mg/mL, about 2.1 mg/mL, about 2.0 mg/mL, about 1.9 mg/mL, about 1.8 mg/mL, about 1.7 mg/mL, or about 1.6 mg/mL; about 1.6 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, about 3.4 mg/mL, about 3.3 mg/mL, about 3.2 mg/mL, about 3.1 mg/mL, about 3.0 mg/mL, about 2.9 mg/mL, about 2.8 mg/mL, about 2.7 mg/mL, about 2.6 mg/mL, about 2.5 mg/mL, about 2.4 mg/mL, about 2.3 mg/mL, about 2.2 mg/mL, about 2.1 mg/mL, about 2.0 mg/mL, about 1.9 mg/mL, or about 1.8 mg/mL; about 1.8 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, about 3.4 mg/mL, about 3.3 mg/mL, about 3.2 mg/mL, about 3.1 mg/mL, about 3.0 mg/mL, about 2.9 mg/mL, about 2.8 mg/mL, about 2.7 mg/mL, about 2.6 mg/mL, about 2.5 mg/mL, about 2.4 mg/mL, about 2.3 mg/mL, about 2.2 mg/mL, about 2.1 mg/mL, about 2.0 mg/mL, or about 1.9 mg/mL; about 1.9 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, about 3.4 mg/mL, about 3.3 mg/mL, about 3.2 mg/mL, about 3.1 mg/mL, about 3.0 mg/mL, about 2.9 mg/mL, about 2.8 mg/mL, about 2.7 mg/mL, about 2.6 mg/mL, about 2.5 mg/mL, about 2.4 mg/mL, about 2.3 mg/mL, about 2.2 mg/mL, about 2.1 mg/mL, or about 2.0 mg/mL; about 2.0 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, about 3.4 mg/mL, about 3.3 mg/mL, about 3.2 mg/mL, about 3.1 mg/mL, about 3.0 mg/mL, about 2.9 mg/mL, about 2.8 mg/mL, about 2.7 mg/mL, about 2.6 mg/mL, about 2.5 mg/mL, about 2.4 mg/mL, about 2.3 mg/mL, about 2.2 mg/mL, or about 2.1 mg/mL; about 2.1 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, about 3.4 mg/mL, about 3.3 mg/mL, about 3.2 mg/mL, about 3.1 mg/mL, about 3.0 mg/mL, about 2.9 mg/mL, about 2.8 mg/mL, about 2.7 mg/mL, about 2.6 mg/mL, about 2.5 mg/mL, about 2.4 mg/mL, about 2.3 mg/mL, or about 2.2 mg/mL; about 2.2 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, about 3.4 mg/mL, about 3.3 mg/mL, about 3.2 mg/mL, about 3.1 mg/mL, about 3.0 mg/mL, about 2.9 mg/mL, about 2.8 mg/mL, about 2.7 mg/mL, about 2.6 mg/mL, or about 2.5 mg/mL; about 2.5 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, about 3.4 mg/mL, about 3.3 mg/mL, about 3.2 mg/mL, about 3.1 mg/mL, about 3.0 mg/mL, about 2.9 mg/mL, about 2.8 mg/mL, about 2.7 mg/mL, or about 2.6 mg/mL; about 2.6 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, about 3.4 mg/mL, about 3.3 mg/mL, about 3.2 mg/mL, about 3.1 mg/mL, about 3.0 mg/mL, about 2.9 mg/mL, about 2.8 mg/mL, or about 2.7 mg/mL; about 2.7 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, about 3.4 mg/mL, about 3.3 mg/mL, about 3.2 mg/mL, about 3.1 mg/mL, about 3.0 mg/mL, about 2.9 mg/mL, or about 2.8 mg/mL; about 2.8 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, about 3.4 mg/mL, about 3.3 mg/mL, about 3.2 mg/mL, about 3.1 mg/mL, about 3.0 mg/mL, or about 2.9 mg/mL; about 2.9 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, about 3.4 mg/mL, about 3.3 mg/mL, about 3.2 mg/mL, about 3.1 mg/mL, or about 3.0 mg/mL; about 3.0 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, about 3.4 mg/mL, about 3.3 mg/mL, about 3.2 mg/mL, or about 3.1 mg/mL; about 3.1 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, about 3.4 mg/mL, about 3.3 mg/mL, or about 3.2 mg/mL; about 3.2 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, about 3.4 mg/mL, or about 3.3 mg/mL; about 3.3 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, about 3.5 mg/mL, or about 3.4 mg/mL; about 3.4 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, about 3.6 mg/mL, or about 3.5 mg/mL; about 3.5 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, about 3.7 mg/mL, or about 3.6 mg/mL; about 3.6 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, about 3.8 mg/mL, or about 3.7 mg/mL; about 3.7 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, about 4.0 mg/mL, about 3.9 mg/mL, or about 3.8 mg/mL; about 3.8 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, about 4.1 mg/mL, or about 4.0 mg/mL; about 4.0 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, about 4.2 mg/mL, or about 4.1 mg/mL; about 4.1 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, about 4.3 mg/mL, or about 4.2 mg/mL; about 4.2 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, about 4.4 mg/mL, or about 4.3 mg/mL; about 4.3 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, about 4.5 mg/mL, or about 4.4 mg/mL; about 4.4 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, about 4.6 mg/mL, or about 4.5 mg/mL; about 4.5 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, about 4.7 mg/mL, or about 4.6 mg/mL; about 4.6 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, about 4.8 mg/mL, or about 4.7 mg/mL; about 4.7 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.9 mg/mL, or about 4.8 mg/mL; about 4.8 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL or about 4.9 mg/mL; about 4.9 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, or about 5.0 mg/mL; about 5.0 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, or about 5.5 mg/mL; about 5.5 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, about 6.5 mg/mL, or about 6.0 mg/mL; about 6.0 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, about 7.0 mg/mL, or about 6.5 mg/mL; about 6.5 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, about 7.5 mg/mL, or about 7.0 mg/mL; about 7.0 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, about 8.0 mg/mL, or about 7.5 mg/mL; about 7.5 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, about 8.5 mg/mL, or about 8.0 mg/mL; about 8.0 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, about 9.0 mg/mL, or about 8.5 mg/mL; about 8.5 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9.5 mg/mL, or about 9.0 mg/mL; about 9.0 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, or about 9.5 mg/mL; about 9.5 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, or about 10 mg/mL; about 10 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, or about 12 mg/mL; about 12 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, or about 14 mg/mL; about 14 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, or about 16 mg/mL; about 16 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, or about 18 mg/mL; about 18 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, or about 20 mg/mL; about 20 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, or about 22 mg/mL; about 22 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, or about 24 mg/mL; about 24 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, or about 26 mg/mL; about 26 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, or about 28 mg/mL; about 28 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, or about 30 mg/mL; about 30 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, or about 32 mg/mL; about 32 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, or about 34 mg/mL; about 34 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, or about 36 mg/mL; about 36 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, or about 38 mg/mL; about 38 mg/mL to about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, or about 40 mg/mL; about 40 mg/mL to about 60 mg/mL, about 58 mg/mL, about 56 mg/mL, about 54 mg/mL, about 52 mg/mL, about 50 mg/mL, about 48 mg/mL, about 46 mg/mL, or about 44 mg/mL; about 44 mg/mL to about 60 mg/mL, about 58 mg/mL, about 56 mg/mL, about 54 mg/mL, about 52 mg/mL, about 50 mg/mL, about 48 mg/mL, or about 46 mg/mL; about 46 mg/mL to about 60 mg/mL, about 58 mg/mL, about 56 mg/mL, about 54 mg/mL, about 52 mg/mL, about 50 mg/mL, or about 48 mg/mL; about 48 mg/mL to about 60 mg/mL, about 58 mg/mL, about 56 mg/mL, about 54 mg/mL, about 52 mg/mL, or about 50 mg/mL; about 50 mg/mL to about 60 mg/mL, about 58 mg/mL, about 56 mg/mL, about 54 mg/mL, or about 52 mg/mL; about 52 mg/mL to about 60 mg/mL, about 58 mg/mL, about 56 mg/mL, or about 54 mg/mL; about 54 mg/mL to about 60 mg/mL, about 58 mg/mL, or about 56 mg/mL; about 56 mg/mL to about 60 mg/mL or about 58 mg/mL; or about 58 mg/mL to about 60 mg/mL of the purine alkaloid (or each of two or more purine alkaloids in examples where two or more purine alkaloids are produced).

After a microorganism as described herein has been cultured and the one or more purine alkaloid has been synthesized, the one or more purine alkaloid can be harvested (and optionally purified). After a mixture (e.g., any of the mixtures described herein) has been incubated and the one or more purine alkaloid has been synthesized, the one or more purine alkaloid can be harvested from the mixture (and optionally purified). Methods for the purification of a purine alkaloid are described in, e.g., Lambert et al., *J Chromatogr A* 1075(1-2):43-49, 2005. It would be appreciated by a skilled artisan that the one or more purine alkaloid that is harvested from a culture of the microorganism (e.g., any of the microorganisms described herein) or from a mixture (e.g., any of the mixtures described herein) can be added to an animal feed or food product in a suitable amount. A suitable amount of one or more purine alkaloids will be dependent on the particular animal food or food product and its intended use.

In accordance with the present invention, there may be employed conventional molecular biology, microbiology, biochemical, and recombinant DNA techniques within the skill of the art. Such techniques are explained fully in the literature. The invention will be further described in the following examples, which do not limit the scope of the methods and compositions of matter described in the claims.

EXAMPLES

Example 1. Production of Theobromine and Caffeine by Genetically Modified *E. coli* Strains A set of experiments was performed to determine whether an *E. coli* strain could be genetically engineered to produce one or more purine alkaloids. The enzymatic pathways of producing purine alkaloids are depicted in FIG. 1.

Materials and Methods

Vectors

In these experiments, expression vectors that include heterologous sequences encoding one or more of 7-methylxanthosine synthase CaXMT from *Coffea arabica* (NCBI Accession number: AB048793), theobromine synthase CaMXMT from *Coffea arabica* (NCBI Accession number: AB048794), caffeine synthase CCS1 from *Coffea arabica* (NCBI Accession number: AB086414), and caffeine synthase TCS from *Camellia sinensis* (NCBI Accession number: AB031280). The vectors were constructed as generally described in Jin et al., *PLoS ONE* 9(8): e105368, 2014; Uefuji et al., *Plant Physiol.* 132: 372-380, 2003; and Mizuno et al., *FEBS Lett.* 534: 75-81, 2003.

Vectors encoding enzymes from the same genetic source (*Coffea arabica*) and vectors encoding enzymes from different genetic sources (*Camellia sinensis* and *Coffea arabica*) were prepared. The first vector, [1], includes sequences encoding each of *Coffea arabica* CaXMT, *Coffea arabica* CaMXMT, and *Camellia sinensis* TCS. Transcription of each of the sequences encoding *Coffea arabica* CaXMT, *Coffea arabica* CaMXMT, and *Camellia sinensis* TCS in construct [1] was regulated using T7 promoters.

The second vector, [2], includes sequences encoding each of *Coffea arabica* CaXMT, *Coffea arabica* CaMXMT, and *Coffea arabica* CCS1. Transcription of each of the sequences encoding *Coffea arabica* CaXMT, *Coffea arabica* CaMXMT, and *Coffea arabica* CCS1 in construct [2] was regulated using T7 promoters.

The sequences encoding *Coffea arabica* CaXMT, *Coffea arabica* CaMXMT, *Coffea arabica* CCS1, and *Camellia sinesis* TCS are described in FIG. 2.

Culturing and Purification

Single colonies of *E. coli* BL21 DE3 transformed with one of the above described expression vectors was used to start pre-cultures in 3 mL LB medium. The cultures were incubated over night at 37° C. with constant shaking. The pre-cultures were harvested by centrifugation at 4,000 RPM and used to inoculate 30 mL of M9 minimal medium for another overnight growth period at 37° C. before adding 0.5 mM of IPTG to induce protein expression. The cultures were incubated at 30° C. for 6 hours on an orbital shaker. The cells were then pelleted by centrifugation at 4,000 RPM for 10 min and (1) suspended in fresh M9 minimal medium containing 1 mM IPTG, corresponding antibiotics, 500 μM xanthosine, with or without 300 μM S-adenosyl L-methionine (SAM), or (2) suspended in fresh M9 minimal medium containing 1 mM IPTG, corresponding antibiotics, 500 μM xanthosine, with 300 μM SAM or 300 μM methionine as methyl group donor. After 24 hours incubation on an orbital shaker at 30° C., the cells were pelleted by centrifugation at 10,000 RPM for 15 min. Spent media was passed through a 0.22 μM filter and analyzed directly by HPLC.

High-Performance Liquid Chromatography (HLPC)

HPLC analysis was used to detect the amounts of theobromine and caffeine in the samples. The HPLC analysis was performed using a reverse-phase C18 column (Agilent Poroshell HPH-C18, 2.1, 150 mm, 2.7 μm, LC column) under isocratic conditions with 10% ACN and a flow rate of 0.2 mL/min at 22° C. and UV detection at 272 nm. The injection volume was 2 μL. HPLC chromatograms were recorded for further analysis. Commercial available caffeine and theobromine standards were used to prepare solutions of known concentrations. Two μL of each standard solution was injected into the HPLC and the peak area was plotted against the concentration to generate standard curves. The peak areas were integrated automatically using ChemStation Software (Agilent).

Results

*E. coli* strains expressing [1] *Coffea arabica* CaXMT, *Coffea arabica* CaMXMT, and *Camellia sinensis* TCS and [2] *Coffea arabica* CaXMT, *Coffea arabica* CaMXMT, and *Coffea arabica* CCS1 were cultured in M9 minimal medium with 0.2% (w/v) glucose in the presence of 500 μM xanthosine and in the presence or absence of 300 μM S-adenosyl methionine (SAM) as methyl group donor. HPLC was performed on the final product and the concentrations of theobromine and caffeine in the final product were determined. Cultures incubated without SAM produced about 5 μM (strain [1]) and 8 μM (strain [2]) theobromine. In the cultures that were incubated in the presence of 300 μM SAM, the concentration of theobromine was about 11 μM using strain [1] and 7.8 μM using strain [2] (FIG. 3). These data show that the addition of SAM is not required for theobromine production in the recombinant *E. coli* strains tested in these experiments.

Figure 4:
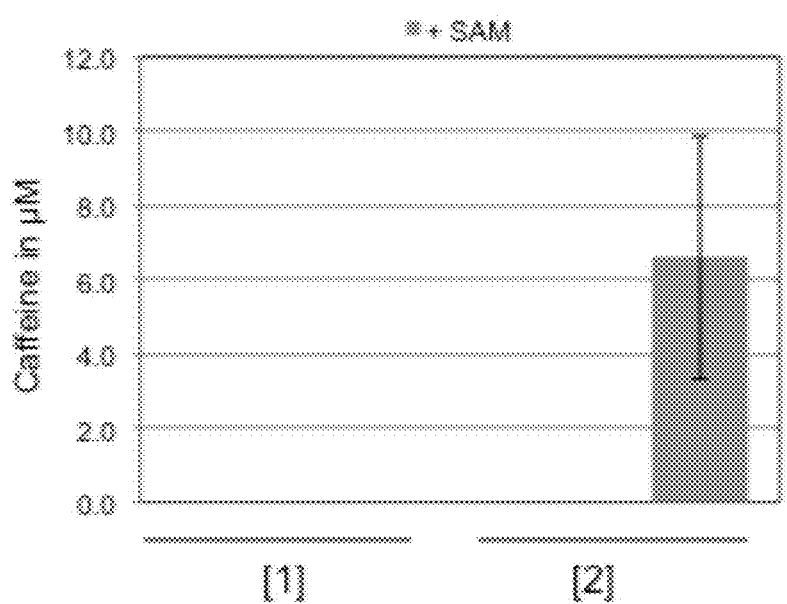
FIG. 4 is a graph showing the production of caffeine using *E. coli* containing construct [1] (expressing *Coffea arabica* 7-methylxanthosine synthase, *Coffea arabica* theobromine synthase, and *Camellia sinensis* caffeine synthase) or *E. coli* containing construct [2] (expressing *Coffea arabica* 7-methylxanthosine synthase, *Coffea arabica* theobromine synthase, and *Coffea arabica* caffeine synthase) following culture in the presence of 500 µM xanthosine and in the presence or absence of 300 µM S-adenosyl-methionine.

Caffeine was detected only in the culture medium from the *E. coli* strain [2] expressing *Coffea arabica* CaXMT, *Coffea arabica* CaMXMT, and *Coffea arabica* CCS1, when the culture was supplemented with both 500 μM xanthosine and 300 μM SAM (FIG. 4). Caffeine was not detected in the culture with *E. coli* [1] containing *Coffea arabica* CaXMT, *Coffea arabica* CaMXMT and *Camellia sinensis* TCS even though the culture was supplemented with both 500 μM xanthosine and 300 μM SAM (FIG. 4).

Figure 5:
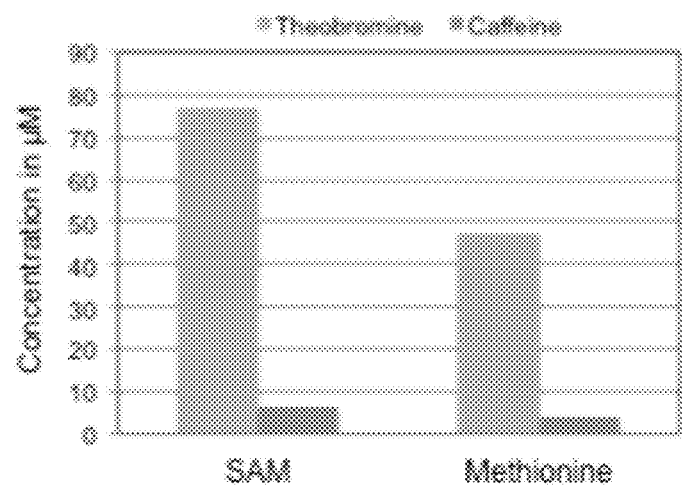
FIG. 5 is a graph showing the production of theobromine and caffeine using *E. coli* containing construct [2] (expressing *Coffea arabica* 7-methylxanthosine synthase, *Coffea arabica* theobromine synthase, and *Coffea arabica* caffeine synthase) following culture in the presence of 500 µM xanthosine and in the presence of 300 µM S-adenosyl-methionine or 300 µM methionine.

Theobromine and caffeine can also be produced using the *E. coli* strain [2] expressing Coffee *arabica* CaXMT, *Coffea arabica* CaMXMT, and *Coffea arabica* CCS1 using methionine as methyl group donor (FIG. 5).

These data show that the recombinant strains provided herein can be used to produce theobromine and caffeine.

Example 2. Production of Theobromine and Caffeine by Recombinant *E. coli* Expressing Fusion Proteins A set of experiments was performed to determine whether the expression of recombinant protein-ligand fusion proteins, a protein scaffold, S-adenosyl-L-homocysteine hydrolase and methionine adenosyltransferase would increase production of theobromine and caffeine.

Materials and Methods

An *E. coli* strain [3] expressing *Coffea arabica* 7-methylxanthosine synthase, *Coffea arabica* theobromine synthase, and *Coffea arabica* caffeine synthase as protein-ligand fusions, scaffold protein, *Corynebacterium glutamicum* or *Pichia pastoris* S-adenosyl-L-homocysteine hydrolase, and *Saccharomyces cerevisiae* methionine adenosyltransferase was included to improve the yield of theobromine and caffeine production. Each ligand domain was paired with only one specific caffeine biosynthesis enzyme. The ligand is a short peptide that interacts with a specific protein domain and is fused to the C-terminus of each protein. The protein domains are expressed in repetitive numbers resulting in a protein structure with properties suitable for use as protein scaffold. A protein scaffold is defined as proteinous structure that allows binding and co-localization of other proteins through specific protein-protein interactions.

Protein-Ligand Fusions

*Coffea arabica* caffeine synthase CCS1-PDZ ligand cDNA and protein sequences are SEQ ID NOs: 1 and 2, respectively.

*Coffea arabica* theobromine synthase CaMXMT-SH3 ligand cDNA and protein sequences are SEQ ID NOs: 3 and 4, respectively.

*Coffea arabica* 7-methylxanthosine synthase CaXMT-GBD ligand cDNA and protein sequences are SEQ ID NOs: 5 and 6, respectively.

Scaffold protein domain cDNA and protein sequences are SEQ ID NOs: 7 and 8, respectively.

Culturing and Purification

Single colonies of *E. coli* BL21 DE3 [3] and *E. coli* W3110 [WT] transformed with compatible T7 promoter or trc, tac, or lac promoter based vectors containing all genes described above and used to start pre-cultures in 3 mL LB medium. The cultures were incubated over night at 37° C. with constant shaking. The pre-cultures were harvested by centrifugation at 4,000 RPM and used to inoculate 30 mL of M9 minimal medium for another overnight growth period at 30° C. After adding of 0.5 mM IPTG to induce protein expression, the [3] cultures were incubated at 30° C. for 6 hours on an orbital shaker. The cells were then pelleted by centrifugation at 4,000 RPM for 10 min and suspended in fresh M9 minimal medium containing 1 mM IPTG, 0.4% (w/v) glucose, corresponding antibiotics, 500 µM xanthosine, and 1 mM methionine as methyl group donor. The over night *E. coli* W3110 [WT] cultures were directly pelleted by centrifugation at 4,000 RPM for 10 min and suspended in fresh M9 minimal medium containing 0.4% (w/v) glucose, 0.05% yeast extract, corresponding antibiotics, xanthosine ranging from 0.1 mM-5 mM and 1 mM methionine as methyl group donor. After 24 hours incubation on an orbital shaker at 30° C., the cells were pelleted by centrifugation at 10,000 RPM for 15 min. Spent media was passed through a 0.22 µM filter and analyzed directly by HPLC.

HPLC analysis was used to detect the amount of theobromine and caffeine in the culture medium, as described in Example 1.

Results

Figure 6:
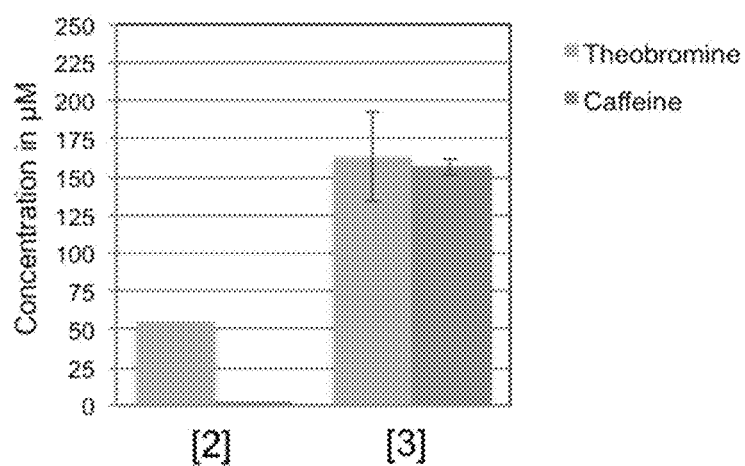
FIG. 6 is a graph showing the production of theobromine and caffeine using *E. coli* expressing *Coffea arabica* 7-methylxanthosine synthase, *Coffea arabica* theobromine synthase, and *Coffea arabica* caffeine synthase (strain [2]) or an *E. coli* strain expressing *Coffea arabica* 7-methylxanthosine synthase, *Coffea arabica* theobromine synthase, and *Coffea arabica* caffeine synthase, each as a protein ligand fusion protein, a scaffold protein, *Corynebacterium glutamicum* or *Pichia pastoris* S-adenosyl-L-homocysteine hydrolase, and *Saccharomyces cerevisiae* methionine adenosyltransferase (strain [3]) following culture in the presence of 500 µM xanthosine and in the presence of 1 mM methionine.
Figure 7:
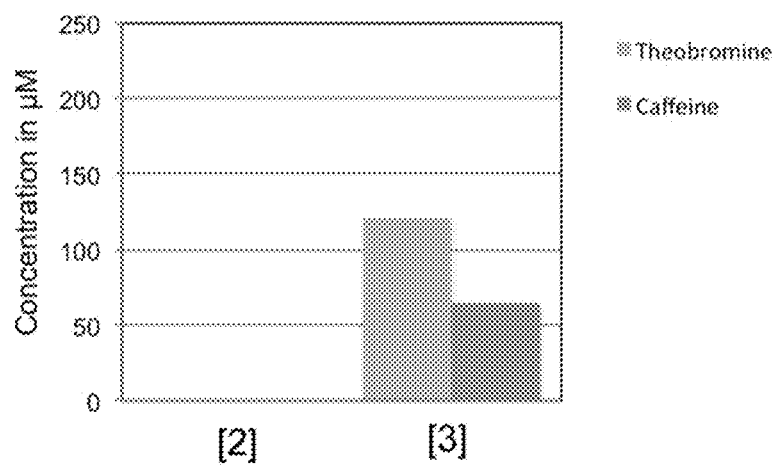
FIG. 7 is a graph showing the production of theobromine and caffeine using *E. coli* expressing *Coffea arabica* 7-methylxanthosine synthase, *Coffea arabica* theobromine synthase, and *Coffea arabica* caffeine synthase (strain [2]) or an *E. coli* strain expressing *Coffea arabica* 7-methylxanthosine synthase, *Coffea arabica* theobromine synthase, and *Coffea arabica* caffeine synthase, each as a protein ligand fusion protein, a scaffold protein, *Corynebacterium glutamicum* or *Pichia pastoris* S-adenosyl-L-homocysteine hydrolase, and *Saccharomyces cerevisiae* methionine adenosyltransferase (strain [3]) following culture in the presence of 500 µM xanthosine and in the absence of added methionine.

The data show that expression of the enzymes *Coffea arabica* 7-methylxanthosine synthase, *Coffea arabica* theobromine synthase, and *Coffea arabica* caffeine synthase as protein ligand-fusion proteins together with the expression of a scaffold protein, *Corynebacterium glutamicum* or *Pichia pastoris* S-adenosyl-L-homocysteine hydrolase, and *Saccharomyces cerevisiae* methionine adenosyltransferase results in an over 30-fold increase in the production of caffeine when cultured in the presence of 500 µM xanthosine and 1 mM methionine. Caffeine production was observed for the strain expressing the enzymes *Coffea arabica* 7-methylxanthosine synthase, *Coffea arabica* theobromine synthase, and *Coffea arabica* caffeine synthase as protein ligand-fusion proteins together with the expression of a scaffold protein, *Corynebacterium glutamicum* or *Pichia pastoris* S-adenosyl-L-homocysteine hydrolase, and *Saccharomyces cerevisiae* methionine adenosyltransferase in the presence of 500 xanthosine with or without added methionine (FIGS. 6 and 7). In contrast, a similar strain that does not express enzymes *Coffea arabica* 7-methylxanthosine synthase, *Coffea arabica* theobromine synthase, and *Coffea arabica* caffeine synthase as protein scaffold domain-fusion proteins and does not express a scaffold protein and *Corynebacterium glutamicum* or *Pichia pastoris* S-adenosyl-L-homocysteine hydrolase, and *Saccharomyces cerevisiae* methionine adenosyltransferase only produces caffeine when cultured in the presence of 500 µM xanthosine and methionine (FIGS. 5 and 7).

These data also show that expression of enzymes *Coffea arabica* 7-methylxanthosine synthase, *Coffea arabica* theobromine synthase, and *Coffea arabica* caffeine synthase as protein-ligand-fusion proteins together with a scaffold protein, *Corynebacterium glutamicum* or *Pichia pastoris* S-adenosyl-L-homocysteine hydrolase, and *Saccharomyces cerevisiae* methionine adenosyltransferase results in increased production of caffeine and theobromine.

Figure 8:
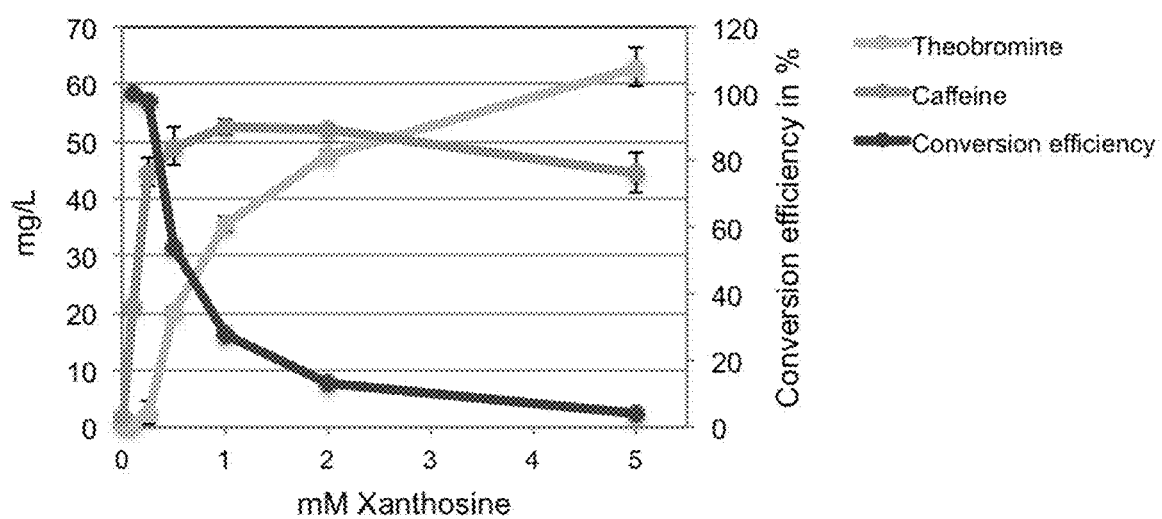
FIG. 8 is a graph of the percentage conversion efficiency of 0.1 mM to 5 mM xanthosine to theobromine or caffeine by a strain of *E. coli* W3110 transformed with expression vectors encoding *Coffea arabica* CaXMT, *Coffea arabica* CaMXMT, and *Coffea arabica* CCS1, *Corynebacterium glutamicum* or *Pichia pastoris* S-adenosyl-L-homocysteine hydrolase, and *Saccharomyces cerevisiae* methionine adenosyltransferase. In these experiments, each culture is also incubated in the presence of 1 mM methionine as the methyl group donor.

The data show that expression of the enzymes *Coffea arabica* 7-methylxanthosine synthase, *Coffea arabica* theobromine synthase, and *Coffea arabica* caffeine synthase together with the expression of a *Corynebacterium glutamicum* or *Pichia pastoris* S-adenosyl-L-homocysteine hydrolase, and *Saccharomyces cerevisiae* methionine adenosyltransferase in *E. coli* W3110 strain [WT] results in production of caffeine and theobromine when cultured in the presence of xanthosine in the range of 0.1 mM-5 mM and with 1 mM methionine as methyl donor (FIG. 8).

Example 3. Production of Theobromine and Caffeine by Recombinant *E. coli* from Preformed Nucleobases A set of experiments was performed to determine the biotransformation of nucleobases into caffeine and theobromine.

Materials and Methods

Single colonies of *E. coli* W3110 [WT] transformed with compatible trc, tac or lac promoter based vectors expressing *Coffea arabica* 7-methylxanthosine synthase, *Coffea arabica* theobromine synthase, and *Coffea arabica* caffeine synthase as protein-ligand fusions, scaffold protein, *Corynebacterium glutamicum* or *Pichia pastoris* S-adenosyl-L-homocysteine hydrolase, *Saccharomyces cerevisiae* methionine adenosyltransferase were, and *Arabidopsis thaliana* guanosine deaminase were used to start pre-cultures in 3 mL LB medium. The *E. coli* W3110 [43] was obtained by deleting the guanosine kinase (gsk, AP 001126), the purine repressor (purR, APC51920), and the purine nucleoside phosphorylase (deoD, AP 004872) in the *E. coli* W3110 strain [WT]. The *E. coli* strains were used to perform biotransformation of preformed nucleobases into theobromine and caffeine. The process of biotransformation is defined as enzymatic modification and conversion of preformed substances (such as ribonucleic acid and deoxyribonucleic acid) into the purine alkaloids in such an incubation condition that the added substances are not normally used for growth but used to produce purine alkaloids. Nucleotides are obtained by hydrolysis of deoxyribonucleic acid and deoxyribonucleic acid from plants or spent microbial strains such as yeast yielding a mixture of the purine and pyrimidine nucleotides. Biotransformation conditions are used to convert purine nucleotides into caffeine alkaloids, whereas pyrimidine nucleotides are isolated as co-products during this process.

Culturing and Purification

Single colonies of *E. coli* W3110 [WT] and [43] transformed with compatible trc, tac or lac promoter based vectors containing all genes described above were used to start pre-cultures in 3 mL LB medium. The cultures were incubated over night at 37° C. with constant shaking. The pre-cultures were harvested by centrifugation at 4,000 RPM and used to inoculate 30 mL of M9 minimal medium for another overnight growth period at 30° C. The cells were then pelleted by centrifugation at 4,000 RPM for 10 min and suspended in fresh M9 minimal medium containing 0.4% (w/v) glucose, 0.05% yeast extract, corresponding antibiotics, 0.5 mM guanosine (FIG. 9A) derived from hydrolyzed plant DNA or 0.5 mM xanthine (FIG. 9B) with 1 mM methionine as methyl group donor. After 24 hours incubation on an orbital shaker at 30° C., the cells were pelleted by centrifugation at 10,000 RPM for 15 min. Spent media was passed through a 0.22 µM filter and analyzed directly by HPLC.

HPLC analysis was used to detect the amount of theobromine and caffeine in the culture medium, as described in Example 1.

Results

Figure 9A:
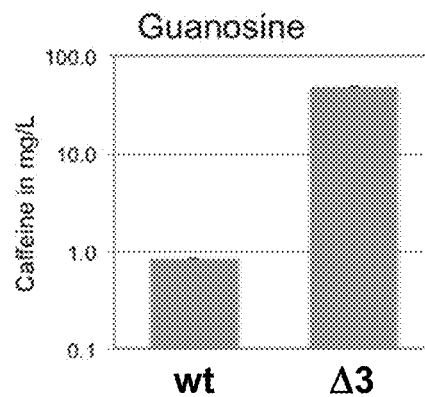
FIG. 9A-C is a set of graphs showing the concentration of caffeine produced by *E. coli* strain W3110 [WT] or *E. coli* strain W3110 with a deletion in an active purine repressor (purR), an active purine nucleoside phosphorylase (deoD), and an active guanosine kinase (gsk) [43] in the presence of 0.5 mM guanosine (FIG. 9A), 0.5 mM guanine (FIG. 9B), or 0.5 mM glucose (FIG. 9C). Both *E. coli* stains [WT] and [43] were transformed with expression vectors encoding *Coffea arabica* CaXMT, *Coffea arabica* CaMXMT, and *Coffea arabica* CCS1, *Corynebacterium glutamicum* or *Pichia pastoris* S-adenosyl-L-homocysteine hydrolase, *Saccharomyces cerevisiae* methionine adenosyltransferase, and *Arabidopsis thaliana* guanosine deaminase. Each culture was also included in the presence of 1 mM methionine as a methyl group donor.
Figure 9B:
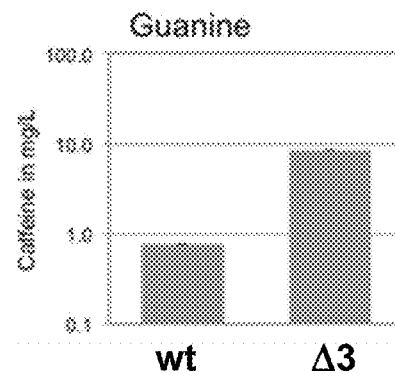

The data show that expression of the enzymes *Coffea arabica* 7-methylxanthosine synthase, *Coffea arabica* theobromine synthase, and *Coffea arabica* caffeine synthase together with the expression of a *Corynebacterium glutamicum* or *Pichia pastoris* S-adenosyl-L-homocysteine hydrolase, *Saccharomyces cerevisiae* methionine adenosyltransferase, and *Arabidopsis thaliana* guanosine deaminase results in the production of caffeine when cultured in the presence of plant DNA derived purine nucleosides and/or nucleobase such as guanosine and guanine with 1 mM methionine as methyl donor (FIGS. 9A and B).

These data also show that expression of enzymes *Coffea arabica* 7-methylxanthosine synthase, *Coffea arabica* theobromine synthase, and *Coffea arabica* caffeine synthase together with *Corynebacterium glutamicum* or *Pichia pastoris* S-adenosyl-L-homocysteine hydrolase, *Saccharomyces cerevisiae* methionine adenosyltransferase, and *Arabidopsis thaliana* guanosine deaminase result in significant increase in production of caffeine from guanosine and guanine with 1 mM methionine as methyl donor in *E. coli* W3110 [43] strain compared to *E. coli* W3110 [WT] strain (FIGS. 9A and B).

Example 4. Sugar Fermentation by Recombinant *E. coli* for Production of Purine Alkaloids A set of experiments using a recombinant *E. coli* strain was performed to produce purine alkaloids such as theobromine and caffeine directly from simple carbon substrates such as sugars, methanol, etc. *E. coli* strain [43] expressing *Coffea arabica* 7-methylxanthosine synthase, *Coffea arabica* theobromine synthase, and *Coffea arabica* caffeine synthase, *Corynebacterium glutamicum* or *Pichia pastoris* S-adenosyl-L-homocysteine hydrolase, *Saccharomyces cerevisiae* methionine adenosyltransferase, and *Arabidopsis thaliana* guanosine deaminase was included to improve the yield of caffeine from simple carbon sources.

Materials and Methods

The recombinant *E. coli* strain [43] described in example 3 was used to perform fermentation of sugars, e.g. glucose into purine alkaloids such as caffeine. The process of fermentation is defined as direct conversion of simple substrates (such as sugars and methanol) into the purine alkaloids.

Culturing and Purification

Single colonies of *E. coli* strains W3110 [WT] and [43] transformed with compatible trc, tac or lac promoter based vectors containing all genes described in example 3 were used to start pre-cultures in 3 mL LB medium. The cultures were incubated over night at 37° C. with constant shaking. The pre-cultures were harvested by centrifugation at 4,000 RPM and used to inoculate 30 mL of M9 minimal medium for another overnight growth period at 30° C. The cells were then pelleted by centrifugation at 4,000 RPM for 10 min and suspended in fresh M9 minimal medium containing 0.4% (w/v) glucose, 0.05% yeast extract, and corresponding antibiotics. After 24 hours incubation on an orbital shaker at 30° C., the cells were pelleted by centrifugation at 10,000 RPM for 15 min. Spent media was passed through a 0.22 µM filter and analyzed directly by HPLC.

HPLC analysis was used to detect the amount of theobromine and caffeine in the culture medium, as described in Example 1.

Results

Figure 9C:
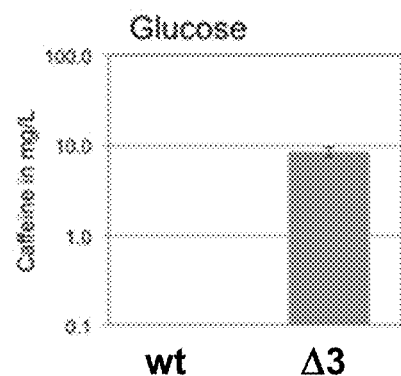
Figure 10:
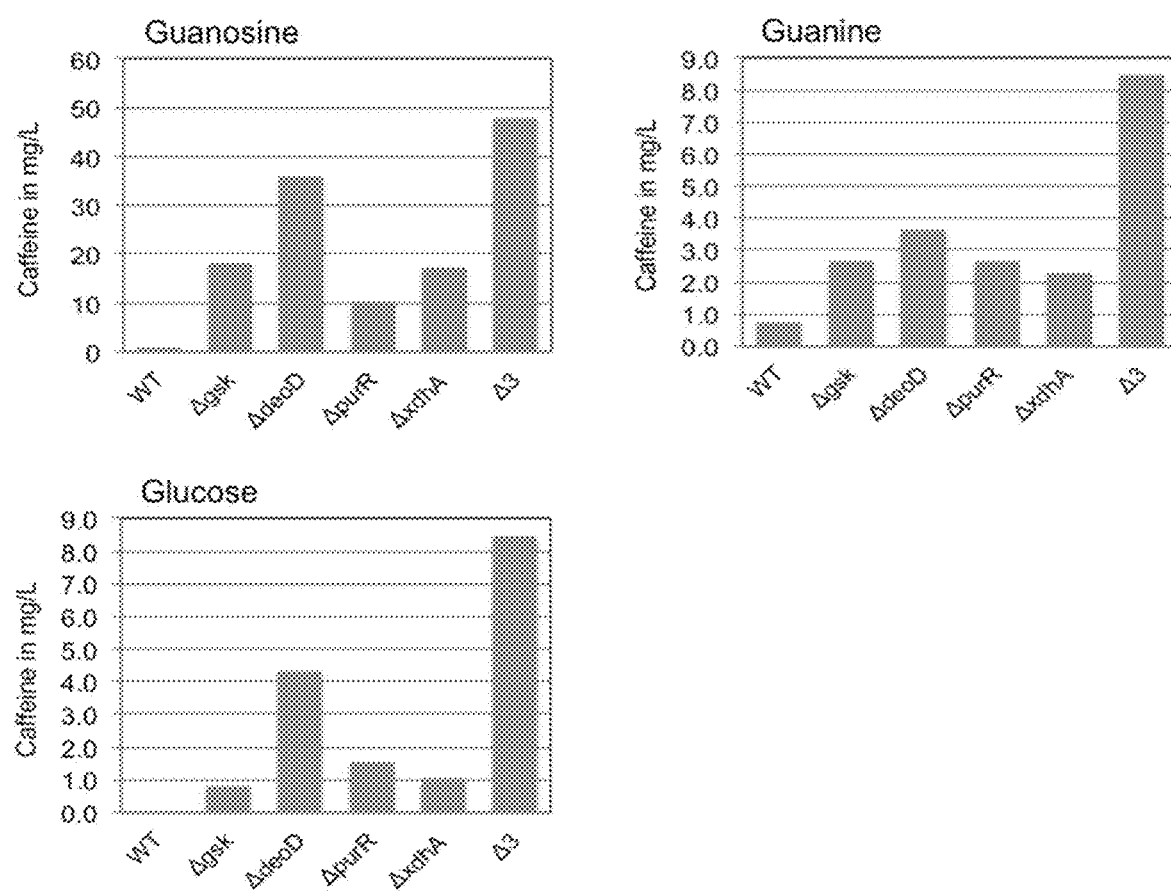
FIG. 10 is a set of graphs showing the amount of caffeine produced by *E. coli* strain W3110 [WT], *E. coli* strain W3110 including a deletion in guanosine kinase [ΔpurR], or *E. coli* strain W3110 including a deletion in the xanthine dehydrogenase [ΔxdhA], and *E. coli* strain W3110 with a deletion in an active purine repressor (purR), an active purine nucleoside phosphorylase (deoD), and an active guanosine kinase (gsk) [43] in the presence of 0.5 mM guanine, 0.5 mM guanosine or 0.4% (w/v) glucose. Each culture was also incubated in the presence of 1 mM methionine as a methyl group donor.

The data show that expression of the enzymes *Coffea arabica* 7-methylxanthosine synthase, *Coffea arabica* theobromine synthase, and *Coffea arabica* caffeine synthase together with the expression of a *Corynebacterium glutamicum* or *Pichia pastoris* S-adenosyl-L-homocysteine hydrolase, *Saccharomyces cerevisiae* methionine adenosyltransferase, and *Arabidopsis thaliana* guanosine deaminase results in the production of caffeine in *E. coli* strain [43] but not *E. coli* strain W3110 [WT] when cultured in the presence of 0.4% (w/v) glucose (FIG. 9C).

Example 5. Cell Extracts from a Recombinant *E. coli* are Mixed with Cell Extracts of Other Microbial Strains to Produce Theobromine and Caffeine A set of experiments using cell extracts of a recombinant *E. coli* strain is performed to determine the production of theobromine and caffeine after incubation with cells extracts from other microbes e.g. *Methylomicrobium buryatense* 5G, *Corynebacterium ammoniagenes*, *Saccharomyces cerevisiae*, or *Ashbya gossypii*.

Materials and Methods

Cell extracts are defined as a cell free mixture of cell constituents or subcellular materials, isolates, or substances. These extracts are prepared under conditions that maintain functional activity of the native enzyme systems.

Culturing and Purification

Single colonies of *E. coli* BL21 DE3 transformed with compatible T7 promoter based vectors containing all genes described in example 1 are used to start pre-cultures in 3 mL LB medium. The cultures are incubated over night at 37° C. with constant shaking and are used to inoculate 30 mL of LB medium. The cultures are gown for another 3 hours at 37° C. with constant shaking before adding 0.5 mM of IPTG to induce protein expression. The cultures are incubated at 30° C. for 6 hours on an orbital shaker. The cells are pelleted by centrifugation at 4,000 RPM for 10 min and suspended in a buffer e.g. 10 mM Hepes buffer pH 8.0 with 0.5 mM of IPTG. The recombinant *E. coli* cell suspension is sonicated (10 short bursts of 10 seconds followed by intervals of 5 seconds for cooling) and mixed with cell extracts from other microbes to produce Theobromine and caffeine. After 24 hours incubation on an orbital shaker at 30° C., the cells material is pelleted by centrifugation at 10,000 RPM for 15 min. Spent media is passed through a 0.22 µM filter and analyzed directly by HPLC.

HPLC analysis is used to detect the amount of theobromine and caffeine in the culture medium, as described in Example 1.

It is to be understood that, while the methods and compositions of matter have been described herein in conjunction with a number of different aspects, the foregoing description of the various aspects is intended to illustrate and not limit the scope of the methods and compositions of matter. Other aspects, advantages, and modifications are within the scope of the following claims.

Disclosed are methods and compositions that can be used for, can be used in conjunction with, can be used in preparation for, or are products of the disclosed methods and compositions. These and other materials are disclosed herein, and it is understood that combinations, subsets, interactions, groups, etc. of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each and every combination and permutation of the compositions and the methods are specifically contemplated unless specifically indicated to the contrary. Likewise, any subset or combination of these is also specifically contemplated and disclosed.

What is claimed is:

1. A recombinant *E. coli* comprising each of:
   (A) 7 methylxanthosine synthase comprising the amino acid sequence of SEQ ID NO: 6;
   (B) theobromine synthase comprising the amino acid sequence of SEQ ID NO: 4;
   (C) caffeine synthase comprising the amino acid sequence of SEQ ID NO: 2; and
   (D) S adenosyl-methionine synthetase comprising the amino acid sequence of any one of SEQ ID NOs. 9-13,
   wherein the recombinant *E. coli* is capable of producing caffeine in a culture medium.

2. The recombinant *E. coli* of claim 1, wherein the culture medium comprises one or more of the following:
   (E) a carbon source selected from the group consisting of: $CO_2$, acetate, glycerol, a sugar, methane, formic acid, and methanol;
   (F) a nitrogen source selected from the group consisting of: nitrate, ammonium, and urea;
   (G) a one-carbon donor selected from the group consisting of: S-adenosyl-methionine, glycine betaine, methionine, and 2-hydroxy-4-(methylthio) butanoate; and
   (H) a nucleobase selected from the group consisting of: adenine, guanine, xanthine, and hypoxanthine; a nucleoside selected from the group consisting of: adenosine, deoxyadenosine, guanosine, inosine, and deoxyguanosine; or a nucleotide selected from the group consisting of: adenine triphosphate (ATP), inosine monophosphate, guanosine 5'-triphosphate (GTP), and xanthosine monophosphate.

3. The recombinant *E. coli* of claim 1, wherein recombinant *E. coli* is capable of secreting or releasing caffeine into the culture medium, when the recombinant *E. coli* is cultured under conditions sufficient to produce caffeine.

4. The recombinant *E. coli* of claim 1, wherein the recombinant *E. coli* has one or both of an increased level of S-adenosyl methionine and an increased rate of recycling of S-adenosyl homocysteine, as compared to a corresponding wildtype *E. coli*.

5. A composition comprising the recombinant *E. coli* of claim 1.

6. A kit comprising a vial comprising the composition of claim 5.

7. A method of producing one or more purine alkaloid, the method comprising:
   culturing a recombinant *E. coli* of claim 1 in a culture medium under conditions sufficient to produce the one or more purine alkaloid; and
   harvesting the one or more purine alkaloid.

8. The method of claim 7, wherein the one or more purine alkaloid is theobromine, caffeine, theophylline, and theacrine.

9. A composition comprising a lysate of the recombinant *E. coli* of claim 1.

10. A composition comprising a cell free lysate containing proteins produced by the recombinant *E. coli* of claim 1.

11. A composition comprising the cell free lysate of claim 10 mixed with a lysate of another microorganism.

12. A method of producing one or more purine alkaloid, the method comprising:
    mixing the composition of claim 9 with one or more substrate(s) to generate a mixture; and
    incubating the mixture under conditions sufficient to produce the one or more purine alkaloid; and
    harvesting the one or more purine alkaloid.

13. The method of claim 12, wherein the one or more purine alkaloid is theobromine, paraxanthine, caffeine, theophylline, and theacrine.

\* \* \* \* \*

SEQUENCE LISTING

<160> NUMBER OF SEQ ID NOS: 13

<210> SEQ ID NO 1
<211> LENGTH: 1203
<212> TYPE: DNA
<213> ORGANISM: Artificial Sequence
<220> FEATURE:
<223> OTHER INFORMATION: Coffea arabica caffeine synthase CCS1-PDZ
      ligand

<400> SEQUENCE: 1

| | | | | | |
|---|---|---|---|---|---|
| atggaactgc | aagaggtgct | gcacatgaac | ggtggcgaag | gcgataccto | ctacgcaaag | 60 |
| aactcctcct | acaacctgtt | cctgatccgc | gtgaagccag | tgctggaaca | gtgcatccaa | 120 |
| gaactgcttc | gcgcaaacct | gccaaacatc | aacaagtgct | tcaaggtggg | cgatctgggc | 180 |
| tgcgcatccg | gtccaaacac | cttctccacc | gtgcgcgaca | tcgtgcagtc | catcgataag | 240 |
| gtgggccaag | aaaagaagaa | cgaactggaa | cgcccaacca | tccagatttt | cttgaacgat | 300 |
| ctcttccaga | acgatttcaa | ctccgtgttc | aagctgctgc | atccttcta | ccgcaacctg | 360 |
| gaaaaagaaa | acggtcgcaa | gatcggctcc | tgcctgatcg | tgcaatgcc | aggtccttc | 420 |
| tactcccgct | tgttcccaga | ggaatccatg | cactttctgc | actcttgcta | ctgcctgcac | 480 |
| tggctgtccc | aggtgccatc | cggtctggtg | accgaactgg | gcatctccgc | aaacaagggc | 540 |
| tgcatctact | cctccaaggc | ctccggtcca | ccaatcaaga | aggcatacct | ggatcagttc | 600 |
| accaaggatt | tcaccacctt | tctgcgcatc | cactccgaag | aactgatctc | ccgtggccgt | 660 |
| atgctgctga | ccttcatctg | caagaagat | gagttcgatc | acccaaactc | tatggatctg | 720 |
| ctggaaatgt | ccatcaacga | tctggtgatc | gaaggccacc | tggaagaaga | gaagctggat | 780 |
| tccttcaacg | tgccaatcta | cgcaccatcc | accgaagagg | tgaagcgcat | cgtggaagaa | 840 |
| gaaggctcct | tcgaaatcct | gtacctggaa | accttctacg | ctccatacga | tgcaggcttc | 900 |
| tccatcgatg | atgattacca | gggtcgctcc | cactccccag | tgtcctgcga | cgaacacgca | 960 |
| cgcgcagcac | acgtggcatc | cgtggtgcgc | tccatctacg | aaccaatcct | ggcatcccac | 1020 |
| ttcggcgaag | caatcctgcc | agacctgtcc | caccgcattg | caaagaacgc | agcaaaggtg | 1080 |
| ctgcgctccg | gcaagggctt | ctacgattcc | gtgatcatct | ccctggcaaa | gaagccagaa | 1140 |
| aaggcagata | tgggatctgg | cagcgggtcc | ggaagtggag | gcgtgaaaga | atccctggtg | 1200 |
| tag | | | | | | 1203 |

<210> SEQ ID NO 2
<211> LENGTH: 400
<212> TYPE: PRT
<213> ORGANISM: Artificial Sequence
<220> FEATURE:
<223> OTHER INFORMATION: Coffea arabica caffeine synthase CCS1-PDZ
      ligand

<400> SEQUENCE: 2

Met Glu Leu Gln Glu Val Leu His Met Asn Gly Gly Glu Gly Asp Thr
1               5                   10                  15

Ser Tyr Ala Lys Asn Ser Ser Tyr Asn Leu Phe Leu Ile Arg Val Lys
            20                  25                  30

Pro Val Leu Glu Gln Cys Ile Gln Glu Leu Leu Arg Ala Asn Leu Pro
        35                  40                  45

Asn Ile Asn Lys Cys Phe Lys Val Gly Asp Leu Gly Cys Ala Ser Gly
    50                  55                  60

Pro Asn Thr Phe Ser Thr Val Arg Asp Ile Val Gln Ser Ile Asp Lys

|    |    |    |    | 65  |    |    |    |    | 70  |    |    |    |    | 75  |    |    |    |    | 80  |
|----|----|----|----|-----|----|----|----|----|-----|----|----|----|----|-----|----|----|----|----|-----|

Val Gly Gln Glu Lys Lys Asn Glu Leu Glu Arg Pro Thr Ile Gln Ile
                    85                      90                      95

Phe Leu Asn Asp Leu Phe Gln Asn Asp Phe Asn Ser Val Phe Lys Leu
                100                     105                     110

Leu Pro Ser Phe Tyr Arg Asn Leu Glu Lys Glu Asn Gly Arg Lys Ile
                115                     120                     125

Gly Ser Cys Leu Ile Gly Ala Met Pro Gly Ser Phe Tyr Ser Arg Leu
130                     135                     140

Phe Pro Glu Glu Ser Met His Phe Leu His Ser Cys Tyr Cys Leu His
145                     150                     155                     160

Trp Leu Ser Gln Val Pro Ser Gly Leu Val Thr Glu Leu Gly Ile Ser
                165                     170                     175

Ala Asn Lys Gly Cys Ile Tyr Ser Ser Lys Ala Ser Gly Pro Pro Ile
                180                     185                     190

Lys Lys Ala Tyr Leu Asp Gln Phe Thr Lys Asp Phe Thr Thr Phe Leu
                195                     200                     205

Arg Ile His Ser Glu Glu Leu Ile Ser Arg Gly Arg Met Leu Leu Thr
210                     215                     220

Phe Ile Cys Lys Glu Asp Glu Phe Asp His Pro Asn Ser Met Asp Leu
225                     230                     235                     240

Leu Glu Met Ser Ile Asn Asp Leu Val Ile Glu Gly His Leu Glu Glu
                245                     250                     255

Glu Lys Leu Asp Ser Phe Asn Val Pro Ile Tyr Ala Pro Ser Thr Glu
                260                     265                     270

Glu Val Lys Arg Ile Val Glu Glu Gly Ser Phe Glu Ile Leu Tyr
                275                     280                     285

Leu Glu Thr Phe Tyr Ala Pro Tyr Asp Ala Gly Phe Ser Ile Asp Asp
                290                     295                     300

Asp Tyr Gln Gly Arg Ser His Ser Pro Val Ser Cys Asp Glu His Ala
305                     310                     315                     320

Arg Ala Ala His Val Ala Ser Val Val Arg Ser Ile Tyr Glu Pro Ile
                325                     330                     335

Leu Ala Ser His Phe Gly Glu Ala Ile Leu Pro Asp Leu Ser His Arg
                340                     345                     350

Ile Ala Lys Asn Ala Ala Lys Val Leu Arg Ser Gly Lys Gly Phe Tyr
                355                     360                     365

Asp Ser Val Ile Ile Ser Leu Ala Lys Lys Pro Glu Lys Ala Asp Met
                370                     375                     380

Gly Ser Gly Ser Gly Ser Gly Gly Val Lys Glu Ser Leu Val
385                     390                     395                     400

<210> SEQ ID NO 3
<211> LENGTH: 1197
<212> TYPE: DNA
<213> ORGANISM: Artificial Sequence
<220> FEATURE:
<223> OTHER INFORMATION: Coffea arabica theobromine synthase CaMXMT-SH3
      ligand

<400> SEQUENCE: 3
atggaactgc aagaggtgct gcacatgaac gaaggcgaag gcgataccte ctacgcaaag      60 aacgcatcct acaacctggc actggcaaag gtgaagccat tcctggaaca gtgcatccgc     120
gaactgcttc gcgcaaacct gccaaacatc aacagtgcat caaggtggc cgatctgggc     180

```
tgcgcatccg gtccaaacac cctgctgacc gtgcgcgaca tcgtgcagtc catcgataag    240
gtgggccaag aagaaaagaa cgaactggaa cgcccaacca tccagatttt cttgaacgat    300
ctcttccaga acgatttcaa ctccgtgttc aagctgctgc catccttcta ccgcaagctg    360
gaaaaagaaa acggtcgcaa gatcggctcc tgcctgatct ccgcaatgcc aggctccttc    420
tacggtcgcc tgttcccaga ggaatccatg cactttctgc actcttgcta ctccgtgcac    480
tggctgtccc aggtgccatc cggtctggtg atcgaactgg gcatcggtgc aaacaagggc    540
tccatctact cctccaaggg ctgccgtcca ccagtgcaga aggcatacct ggatcagttc    600
accaaggatt tcaccacctt ctgcgcatc cactccaaag aactgttctc ccgtggccgt    660
atgctgctga cctgcatctg caaggtggat gagttcgatg aaccaaaccc actggatctg    720
ctggatatgg caatcaacga tctgatcgtg gaaggcctgc tggaagaaga aaagctggat    780
tccttcaaca tcccattctt caccccatcc gctgaagagg tgaagtgcat cgtggaagaa    840
gaaggctcct gcgaaatcct gtacctggaa accttcaagg cacactacga tgcagcattc    900
tccatcgatg atgattaccc agtgcgctcc cacgagcaga tcaaggcaga atacgtggca    960
tccctgatcc gctccgtgta cgaaccaatc ctggcatccc acttcggcga agcaatcatg   1020
ccagacctgt tccaccgcct ggcaaagcac gcagccaagg tgctccacat gggcaagggc   1080
tgctacaaca acctgatcat ctccctggca aagaaaccag aaaagtccga tgtgggatct   1140
ggttcgggca gtggttctgg gcctccgcca gccttacctc cgaagcgtcg ccgttag      1197
```

<210> SEQ ID NO 4
<211> LENGTH: 398
<212> TYPE: PRT
<213> ORGANISM: Artificial Sequence
<220> FEATURE:
<223> OTHER INFORMATION: Coffea arabica theobromine synthase CaMXMT-SH3
      ligand

<400> SEQUENCE: 4

```
Met Glu Leu Gln Glu Val Leu His Met Asn Glu Gly Glu Gly Asp Thr
1               5                   10                  15

Ser Tyr Ala Lys Asn Ala Ser Tyr Asn Leu Ala Leu Ala Lys Val Lys
            20                  25                  30

Pro Phe Leu Glu Gln Cys Ile Arg Glu Leu Leu Arg Ala Asn Leu Pro
        35                  40                  45

Asn Ile Asn Lys Cys Ile Lys Val Ala Asp Leu Gly Cys Ala Ser Gly
    50                  55                  60

Pro Asn Thr Leu Leu Thr Val Arg Asp Ile Val Gln Ser Ile Asp Lys
65                  70                  75                  80

Val Gly Gln Glu Glu Lys Asn Glu Leu Glu Arg Pro Thr Ile Gln Ile
                85                  90                  95

Phe Leu Asn Asp Leu Phe Gln Asn Asp Phe Asn Ser Val Phe Lys Leu
            100                 105                 110

Leu Pro Ser Phe Tyr Arg Lys Leu Glu Lys Glu Asn Gly Arg Lys Ile
        115                 120                 125

Gly Ser Cys Leu Ile Ser Ala Met Pro Gly Ser Phe Tyr Gly Arg Leu
    130                 135                 140

Phe Pro Glu Glu Ser Met His Phe Leu His Ser Cys Tyr Ser Val His
145                 150                 155                 160

Trp Leu Ser Gln Val Pro Ser Gly Leu Val Ile Glu Leu Gly Ile Gly
                165                 170                 175

Ala Asn Lys Gly Ser Ile Tyr Ser Ser Lys Gly Cys Arg Pro Pro Val
```

|  | 180 |  |  | 185 |  |  | 190 |  |
| --- | --- | --- | --- | --- | --- | --- | --- | --- |

Gln Lys Ala Tyr Leu Asp Gln Phe Thr Lys Asp Phe Thr Thr Phe Leu
            195                 200                 205

Arg Ile His Ser Lys Glu Leu Phe Ser Arg Gly Arg Met Leu Leu Thr
    210                 215                 220

Cys Ile Cys Lys Val Asp Glu Phe Asp Glu Pro Asn Pro Leu Asp Leu
225                 230                 235                 240

Leu Asp Met Ala Ile Asn Asp Leu Ile Val Glu Gly Leu Leu Glu Glu
                245                 250                 255

Glu Lys Leu Asp Ser Phe Asn Ile Pro Phe Phe Thr Pro Ser Ala Glu
            260                 265                 270

Glu Val Lys Cys Ile Val Glu Glu Gly Ser Cys Glu Ile Leu Tyr
        275                 280                 285

Leu Glu Thr Phe Lys Ala His Tyr Asp Ala Ala Phe Ser Ile Asp Asp
        290                 295                 300

Asp Tyr Pro Val Arg Ser His Glu Gln Ile Lys Ala Glu Tyr Val Ala
305                 310                 315                 320

Ser Leu Ile Arg Ser Val Tyr Glu Pro Ile Leu Ala Ser His Phe Gly
                325                 330                 335

Glu Ala Ile Met Pro Asp Leu Phe His Arg Leu Ala Lys His Ala Ala
            340                 345                 350

Lys Val Leu His Met Gly Lys Gly Cys Tyr Asn Asn Leu Ile Ile Ser
        355                 360                 365

Leu Ala Lys Lys Pro Glu Lys Ser Asp Val Gly Ser Gly Ser Gly Ser
    370                 375                 380

Gly Ser Gly Pro Pro Pro Ala Leu Pro Pro Lys Arg Arg Arg
385                 390                 395

```
<210> SEQ ID NO 5
<211> LENGTH: 1242
<212> TYPE: DNA
<213> ORGANISM: Artificial Sequence
<220> FEATURE:
<223> OTHER INFORMATION: Coffea arabica 7-methylxanthosine synthase
      CaXMT-GBD ligand

<400> SEQUENCE: 5
```

| | | | | |
|---|---|---|---|---|
| atggaactgc aagaggtgct gcgcatgaac ggtggcgaag gcgatacctc ctacgcaaag | 60 |
| aactccgcat acaaccagct ggtgctggca aaggtgaagc cagtgctgga acagtgcgtg | 120 |
| cgcgaactgc ttcgcgcaaa cctgccaaac atcaacaagt gcatcaaggt ggccgatctg | 180 |
| ggctgcgcat ccggtccaaa caccctgctg accgtgcgcg acatcgtgca gtccatcgat | 240 |
| aaggtgggcc aagaaaagaa gaacgaactg gaacgcccaa ccatccagat tttcttgaac | 300 |
| gatctcttcc aaacgatttc aactccgtg ttcaagctgc tgccatcctt ctaccgcaag | 360 |
| ctggaaaaag aaaacggtcg caagatcggc tcctgcctga tcggtgcaat gccaggctcc | 420 |
| ttctactccc gcttgttccc agaggaatcc atgcactttc tgcactcttg ctactgcctc | 480 |
| cagtggctgt cccaggtgcc atccggtctg gtgaccgaac tgggcatctc caccaacaag | 540 |
| ggctccatct actcctccaa ggcatcccgc ttgccagtgc agaaggcata cctggatcag | 600 |
| ttcaccaagg atttcaccac ctttctgcgc atccactccg aagaactgtt ctcccacggt | 660 |
| cgcatgttgc tgacctgcat ctgcaagggc gtggaactgg atgcacgcaa cgcaatcgat | 720 |
| ctgctggaaa tggcaatcaa cgatctggtg gtggaaggcc acctggaaga agaaaagctg | 780 |
| gattccttca acctgccagt gtacatccca tccgctgaag aggtgaagtg catcgtggaa | 840 |

-continued

```
gaagaaggct ccttcgaaat cctgtacctg gaaaccttca aggtgctgta cgatgcaggc      900
ttctccatcg atgatgaaca catcaaggca gaatacgtgg catcctccgt tcgcgcagtg      960
tacgaaccaa tcctggcatc ccacttcggc gaagcaatca tcccagacat cttccaccgc     1020
ttcgcaaagc acgcagcaaa ggtgctgcca ctgggcaagg gcttctacaa caacctgatc     1080
atctccctgg caagaaaacc agaaaagtcc gatgtgggat ctgggtctgg atcgggcagc     1140
ggtctggtgg gcgcgctgat gcatgtgatg cagaaacgca gccgcgcgat tcatagcagc     1200
gatgaaggcg aagatcaggc gggcgatgaa gatgaagatt ag                        1242
```

<210> SEQ ID NO 6
<211> LENGTH: 413
<212> TYPE: PRT
<213> ORGANISM: Artificial Sequence
<220> FEATURE:
<223> OTHER INFORMATION: Coffea arabica 7-methylxanthosine synthase
      CaXMT-GBD ligand

<400> SEQUENCE: 6

```
Met Glu Leu Gln Glu Val Leu Arg Met Asn Gly Gly Glu Gly Asp Thr
1               5                   10                  15

Ser Tyr Ala Lys Asn Ser Ala Tyr Asn Gln Leu Val Leu Ala Lys Val
            20                  25                  30

Lys Pro Val Leu Glu Gln Cys Val Arg Glu Leu Leu Arg Ala Asn Leu
        35                  40                  45

Pro Asn Ile Asn Lys Cys Ile Lys Val Ala Asp Leu Gly Cys Ala Ser
    50                  55                  60

Gly Pro Asn Thr Leu Leu Thr Val Arg Asp Ile Val Gln Ser Ile Asp
65                  70                  75                  80

Lys Val Gly Gln Glu Lys Lys Asn Glu Leu Glu Arg Pro Thr Ile Gln
                85                  90                  95

Ile Phe Leu Asn Asp Leu Phe Pro Asn Asp Phe Asn Ser Val Phe Lys
            100                 105                 110

Leu Leu Pro Ser Phe Tyr Arg Lys Leu Glu Lys Glu Asn Gly Arg Lys
        115                 120                 125

Ile Gly Ser Cys Leu Ile Gly Ala Met Pro Gly Ser Phe Tyr Ser Arg
    130                 135                 140

Leu Phe Pro Glu Glu Ser Met His Phe Leu His Ser Cys Tyr Cys Leu
145                 150                 155                 160

Gln Trp Leu Ser Gln Val Pro Ser Gly Leu Val Thr Glu Leu Gly Ile
                165                 170                 175

Ser Thr Asn Lys Gly Ser Ile Tyr Ser Ser Lys Ala Ser Arg Leu Pro
            180                 185                 190

Val Gln Lys Ala Tyr Leu Asp Gln Phe Thr Lys Asp Phe Thr Thr Phe
        195                 200                 205

Leu Arg Ile His Ser Glu Glu Leu Phe Ser His Gly Arg Met Leu Leu
    210                 215                 220

Thr Cys Ile Cys Lys Gly Val Glu Leu Asp Ala Arg Asn Ala Ile Asp
225                 230                 235                 240

Leu Leu Glu Met Ala Ile Asn Asp Leu Val Val Glu Gly His Leu Glu
                245                 250                 255

Glu Glu Lys Leu Asp Ser Phe Asn Leu Pro Val Tyr Ile Pro Ser Ala
            260                 265                 270

Glu Glu Val Lys Cys Ile Val Glu Glu Gly Ser Phe Glu Ile Leu
        275                 280                 285
```

```
Tyr Leu Glu Thr Phe Lys Val Leu Tyr Asp Ala Gly Phe Ser Ile Asp
        290                 295                 300

Asp Glu His Ile Lys Ala Glu Tyr Val Ala Ser Ser Val Arg Ala Val
305                 310                 315                 320

Tyr Glu Pro Ile Leu Ala Ser His Phe Gly Glu Ala Ile Ile Pro Asp
                325                 330                 335

Ile Phe His Arg Phe Ala Lys His Ala Ala Lys Val Leu Pro Leu Gly
                340                 345                 350

Lys Gly Phe Tyr Asn Asn Leu Ile Ile Ser Leu Ala Lys Lys Pro Glu
            355                 360                 365

Lys Ser Asp Val Gly Ser Gly Ser Gly Ser Gly Leu Val Gly
        370                 375                 380

Ala Leu Met His Val Met Gln Lys Arg Ser Arg Ala Ile His Ser Ser
385                 390                 395                 400

Asp Glu Gly Glu Asp Gln Ala Gly Asp Glu Asp Glu Asp
                405                 410
```

<210> SEQ ID NO 7
<211> LENGTH: 1428
<212> TYPE: DNA
<213> ORGANISM: Artificial Sequence
<220> FEATURE:
<223> OTHER INFORMATION: Scaffold protein domain

<400> SEQUENCE: 7

```
atgggaacca aagcagatat tggcaccccg agcaattttc agcatattgg tcatgttggt      60
tgggacccga ataccggttt tgatctgaat aatctggacc cggaactgaa aaacctgttt     120
gatatgtgtg gtattagcga agcacagctg aaagatcgtg aaaccagcaa agtgatctat     180
gactttatcg aaaaaaccgg tggtgttgaa gccgtgaaaa atgaactgcg tcgtcaggca     240
ccgggaagcg gtagcggttc agggtctggt tcgggttctg gcagtggtag cggatctgcc     300
gaatatgttc gtgcactgtt tgattttaat ggcaacgatg aagaggacct gccgttcaaa     360
aaaggtgata ttctgcgtat tcgtgataaa ccggaagaac agtggtggaa tgcagaagat     420
agcgaaggta acgtggtat gattccggtt ccgtatgttg aaaaatatgg ttctggcagt     480
ggatctggca gcggctcagg cagcggttct ggctcaggat ctgccgaata tgttcgtgca     540
ctgtttgatt ttaatggcaa cgatgaagag gacctgccgt tcaaaaaagg tgatattctg     600
cgtattcgtg ataaaccgga gaacagtgg tggaatgcag aagatagcga aggtaaacgt     660
ggtatgattc cggttccgta tgttgaaaaa tatggttctg gcagtggatc tggcagcggc     720
tcaggcagcg gttctggctc aggatctctg caacgtcgtc gtgttaccgt tcgtaaagca     780
gatgccggtg gtctgggtat tagcattaaa ggtggtcgtg aaaacaaaat gccgatcctg     840
attagcaaaa tctttaaagg tctggcagca gatcagaccg aagccctgtt tgttggtgat     900
gcaattctga gcgttaatgg tgaggacctg agcagcgcaa cccatgatga gcagttcagg     960
gcactgaaaa aaacaggtaa agaagttgtg ctggaagtca atacatgaa agaagttagc    1020
ccgtatttca aaggctcagg atcaggctct ggtagtggaa gcgggagtgg gagcggaagc    1080
ggatctctgc aacgtcgtcg tgttaccgtt cgtaaagca atgccggtgg tctgggtatt    1140
agcattaaag gtggtcgtga aaacaaaatg ccgatcctga ttagcaaaat ctttaaaggt    1200
ctggcagcag atcagaccga agccctgttt gttggtgatg caattctgag cgttaatggt    1260
gaggacctga gcagcgcaac ccatgatgaa gcagttcagg cactgaaaaa aacaggtaaa    1320
```

```
gaagttgtgc tggaagtcaa atacatgaaa gaagttagcc cgtatttcaa aggctcagga      1380
tcaggctctg gtagtggaag cgggagtggg agcggaagcg gatcctag                  1428
```

<210> SEQ ID NO 8
<211> LENGTH: 475
<212> TYPE: PRT
<213> ORGANISM: Artificial Sequence
<220> FEATURE:
<223> OTHER INFORMATION: Scaffold protein domain

<400> SEQUENCE: 8

```
Met Gly Thr Lys Ala Asp Ile Gly Thr Pro Ser Asn Phe Gln His Ile
1               5                   10                  15

Gly His Val Gly Trp Asp Pro Asn Thr Gly Phe Asp Leu Asn Asn Leu
            20                  25                  30

Asp Pro Glu Leu Lys Asn Leu Phe Asp Met Cys Gly Ile Ser Glu Ala
        35                  40                  45

Gln Leu Lys Asp Arg Glu Thr Ser Lys Val Ile Tyr Asp Phe Ile Glu
    50                  55                  60

Lys Thr Gly Gly Val Glu Ala Val Lys Asn Glu Leu Arg Arg Gln Ala
65                  70                  75                  80

Pro Gly Ser Gly Ser Gly Ser Gly Ser Gly Ser Gly Ser Gly Ser Gly
                85                  90                  95

Ser Gly Ser Ala Glu Tyr Val Arg Ala Leu Phe Asp Phe Asn Gly Asn
            100                 105                 110

Asp Glu Glu Asp Leu Pro Phe Lys Lys Gly Asp Ile Leu Arg Ile Arg
        115                 120                 125

Asp Lys Pro Glu Glu Gln Trp Trp Asn Ala Glu Asp Ser Glu Gly Lys
    130                 135                 140

Arg Gly Met Ile Pro Val Pro Tyr Val Glu Lys Tyr Gly Ser Gly Ser
145                 150                 155                 160

Gly Ser Gly Ser Gly Ser Gly Ser Gly Ser Gly Ser Gly Ser Ala Glu
                165                 170                 175

Tyr Val Arg Ala Leu Phe Asp Phe Asn Gly Asn Asp Glu Glu Asp Leu
            180                 185                 190

Pro Phe Lys Lys Gly Asp Ile Leu Arg Ile Arg Asp Lys Pro Glu Glu
        195                 200                 205

Gln Trp Trp Asn Ala Glu Asp Ser Glu Gly Lys Arg Gly Met Ile Pro
    210                 215                 220

Val Pro Tyr Val Glu Lys Tyr Gly Ser Gly Ser Gly Ser Gly Ser Gly
225                 230                 235                 240

Ser Gly Ser Gly Ser Gly Ser Leu Gln Arg Arg Val Thr
                245                 250                 255

Val Arg Lys Ala Asp Ala Gly Gly Leu Gly Ile Ser Ile Lys Gly Gly
            260                 265                 270

Arg Glu Asn Lys Met Pro Ile Leu Ile Ser Lys Ile Phe Lys Gly Leu
        275                 280                 285

Ala Ala Asp Gln Thr Glu Ala Leu Phe Val Gly Asp Ala Ile Leu Ser
    290                 295                 300

Val Asn Gly Glu Asp Leu Ser Ser Ala Thr His Asp Glu Ala Val Gln
305                 310                 315                 320

Ala Leu Lys Lys Thr Gly Lys Glu Val Val Leu Glu Val Lys Tyr Met
                325                 330                 335

Lys Glu Val Ser Pro Tyr Phe Lys Gly Ser Gly Ser Gly Ser Gly Ser
            340                 345                 350
```

Gly Ser Gly Ser Gly Ser Gly Ser Leu Gln Arg Arg Val
            355                 360             365

Thr Val Arg Lys Ala Asp Ala Gly Gly Leu Gly Ile Ser Ile Lys Gly
    370             375             380

Gly Arg Glu Asn Lys Met Pro Ile Leu Ile Ser Lys Ile Phe Lys Gly
385             390                 395                 400

Leu Ala Ala Asp Gln Thr Glu Ala Leu Phe Val Gly Asp Ala Ile Leu
                405                 410                 415

Ser Val Asn Gly Glu Asp Leu Ser Ser Ala Thr His Asp Glu Ala Val
            420                 425                 430

Gln Ala Leu Lys Lys Thr Gly Lys Glu Val Val Leu Glu Val Lys Tyr
        435                 440                 445

Met Lys Glu Val Ser Pro Tyr Phe Lys Gly Ser Gly Ser Gly Ser Gly
    450                 455                 460

Ser Gly Ser Gly Ser Gly Ser Gly Ser
465             470             475

<210> SEQ ID NO 9
<211> LENGTH: 384
<212> TYPE: PRT
<213> ORGANISM: E. coli

<400> SEQUENCE: 9

Met Ala Lys His Leu Phe Thr Ser Glu Ser Val Ser Glu Gly His Pro
1               5                   10                  15

Asp Lys Ile Ala Asp Gln Ile Ser Asp Ala Val Leu Asp Ala Ile Leu
            20                  25                  30

Glu Gln Asp Pro Lys Ala Arg Val Ala Cys Glu Thr Tyr Val Lys Thr
        35                  40                  45

Gly Met Val Leu Val Gly Gly Glu Ile Thr Thr Ser Ala Trp Val Asp
    50                  55                  60

Ile Glu Glu Ile Thr Arg Asn Thr Val Arg Glu Ile Gly Tyr Val His
65                  70                  75                  80

Ser Asp Met Gly Phe Asp Ala Asn Ser Cys Ala Val Leu Ser Ala Ile
                85                  90                  95

Gly Lys Gln Ser Pro Asp Ile Asn Gln Gly Val Asp Arg Ala Asp Pro
            100                 105                 110

Leu Glu Gln Gly Ala Gly Asp Gln Gly Leu Met Phe Gly Tyr Ala Thr
        115                 120                 125

Asn Glu Thr Asp Val Leu Met Pro Ala Pro Ile Thr Tyr Ala His Arg
    130                 135                 140

Leu Val Gln Arg Gln Ala Glu Val Arg Lys Asn Gly Thr Leu Pro Trp
145                 150                 155                 160

Leu Arg Pro Asp Ala Lys Ser Gln Val Thr Phe Gln Tyr Asp Asp Gly
                165                 170                 175

Lys Ile Val Gly Ile Asp Ala Val Val Leu Ser Thr Gln His Ser Glu
            180                 185                 190

Glu Ile Asp Gln Lys Ser Leu Gln Glu Ala Val Met Glu Glu Ile Ile
        195                 200                 205

Lys Pro Ile Leu Pro Ala Glu Trp Leu Thr Ser Ala Thr Lys Phe Phe
    210                 215                 220

Ile Asn Pro Thr Gly Arg Phe Val Ile Gly Gly Pro Met Gly Asp Cys
225                 230                 235                 240

Gly Leu Thr Gly Arg Lys Ile Ile Val Asp Thr Tyr Gly Gly Met Ala

```
                245                 250                 255
Arg His Gly Gly Gly Ala Phe Ser Gly Lys Asp Pro Ser Lys Val Asp
            260                 265                 270

Arg Ser Ala Ala Tyr Ala Ala Arg Tyr Val Ala Lys Asn Ile Val Ala
            275                 280             285

Ala Gly Leu Ala Asp Arg Cys Glu Ile Gln Val Ser Tyr Ala Ile Gly
            290                 295                 300

Val Ala Glu Pro Thr Ser Ile Met Val Glu Thr Phe Gly Thr Glu Lys
305                 310                 315                 320

Val Pro Ser Glu Gln Leu Thr Leu Leu Val Arg Glu Phe Phe Asp Leu
                325                 330                 335

Arg Pro Tyr Gly Leu Ile Gln Met Leu Asp Leu Leu His Pro Ile Tyr
            340                 345                 350

Lys Glu Thr Ala Ala Tyr Gly His Phe Gly Arg Glu His Phe Pro Trp
            355                 360                 365

Glu Lys Thr Asp Lys Ala Gln Leu Leu Arg Asp Ala Ala Gly Leu Lys
            370                 375             380

<210> SEQ ID NO 10
<211> LENGTH: 407
<212> TYPE: PRT
<213> ORGANISM: Corynebacterium glutamicum

<400> SEQUENCE: 10

Met Ala Gln Pro Thr Ala Val Arg Leu Phe Thr Ser Glu Ser Val Thr
1               5                   10                  15

Glu Gly His Pro Asp Lys Ile Cys Asp Ala Ile Ser Asp Thr Ile Leu
            20                  25                  30

Asp Ala Leu Leu Glu Lys Asp Pro Gln Ser Arg Val Ala Val Glu Thr
        35                  40                  45

Val Val Thr Thr Gly Ile Val His Val Gly Glu Val Arg Thr Ser
    50                  55                  60

Ala Tyr Val Glu Ile Pro Gln Leu Val Arg Asn Lys Leu Ile Glu Ile
65              70                  75                  80

Gly Phe Asn Ser Ser Glu Val Gly Phe Asp Gly Arg Thr Cys Gly Val
                85                  90                  95

Ser Val Ser Ile Gly Glu Gln Ser Gln Glu Ile Ala Asp Gly Val Asp
            100                 105                 110

Asn Ser Asp Glu Ala Arg Thr Asn Gly Asp Val Glu Glu Asp Asp Arg
        115                 120                 125

Ala Gly Ala Gly Asp Gln Gly Leu Met Phe Gly Tyr Ala Thr Asn Glu
    130                 135                 140

Thr Glu Glu Tyr Met Pro Leu Pro Ile Ala Leu Ala His Arg Leu Ser
145                 150                 155                 160

Arg Arg Leu Thr Gln Val Arg Lys Glu Gly Ile Val Pro His Leu Arg
                165                 170                 175

Pro Asp Gly Lys Thr Gln Val Thr Phe Ala Tyr Asp Ala Gln Asp Arg
            180                 185                 190

Pro Ser His Leu Asp Thr Val Val Ile Ser Thr Gln His Asp Pro Glu
        195                 200                 205

Val Asp Arg Ala Trp Leu Glu Thr Gln Leu Arg Glu His Val Ile Asp
    210                 215                 220

Trp Val Ile Lys Asp Ala Gly Ile Glu Asp Leu Ala Thr Gly Glu Ile
225                 230                 235                 240
```

Thr Val Leu Ile Asn Pro Ser Gly Ser Phe Ile Leu Gly Gly Pro Met
            245                 250                 255

Gly Asp Ala Gly Leu Thr Gly Arg Lys Ile Ile Val Asp Thr Tyr Gly
        260                 265                 270

Gly Met Ala Arg His Gly Gly Ala Phe Ser Gly Lys Asp Pro Ser
    275                 280                 285

Lys Val Asp Arg Ser Ala Ala Tyr Ala Met Arg Trp Val Ala Lys Asn
290                 295                 300

Ile Val Ala Ala Gly Leu Ala Asp Arg Ala Glu Val Gln Val Ala Tyr
305                 310                 315                 320

Ala Ile Gly Arg Ala Lys Pro Val Gly Leu Tyr Val Glu Thr Phe Asp
            325                 330                 335

Thr Asn Lys Glu Gly Leu Ser Asp Glu Gln Ile Gln Ala Ala Val Leu
        340                 345                 350

Glu Val Phe Asp Leu Arg Pro Ala Ala Ile Ile Arg Glu Leu Asp Leu
    355                 360                 365

Leu Arg Pro Ile Tyr Ala Asp Thr Ala Ala Tyr Gly His Phe Gly Arg
    370                 375                 380

Thr Asp Leu Asp Leu Pro Trp Glu Ala Ile Asp Arg Val Asp Glu Leu
385                 390                 395                 400

Arg Ala Ala Leu Lys Leu Ala
            405

<210> SEQ ID NO 11
<211> LENGTH: 384
<212> TYPE: PRT
<213> ORGANISM: Komagataella phaffii

<400> SEQUENCE: 11

Met Ser Lys Asn Glu Thr Phe Phe Thr Ser Glu Ser Val Gly Glu
1               5                   10                  15

Gly His Pro Asp Lys Leu Cys Asp Gln Val Ser Asp Ala Val Leu Asp
            20                  25                  30

Ala Cys Leu Thr Val Asp Pro Leu Ser Lys Val Ala Cys Glu Thr Ala
        35                  40                  45

Ala Lys Thr Gly Met Val Met Val Phe Gly Glu Ile Thr Thr Lys Ala
    50                  55                  60

Gln Leu Asp Phe Gln Lys Ile Ile Arg Asp Thr Val Lys His Ile Gly
65                  70                  75                  80

Tyr Asp His Ser Asp Lys Gly Leu Asp Tyr Lys Thr Met Ser Val Leu
                85                  90                  95

Val Ala Ile Glu His Gln Ser Pro Asp Ile Ala Gln Gly Leu His Tyr
            100                 105                 110

Glu Lys Ala Leu Glu Glu Leu Gly Ala Gly Asp Gln Gly Ile Met Phe
        115                 120                 125

Gly Tyr Ala Thr Asp Glu Thr Asp Glu Lys Leu Pro Leu Thr Leu Leu
    130                 135                 140

Leu Ala His Gln Leu Asn His Glu Leu Ala Ser Cys Arg Arg Ser Gly
145                 150                 155                 160

Ser Leu Pro Trp Leu Arg Pro Asp Thr Lys Thr Gln Val Thr Ile Glu
                165                 170                 175

Tyr Lys Tyr Asp Asn Gly Ala Val Ile Pro Leu Arg Val Asp Thr Val
            180                 185                 190

Val Ile Ser Ala Gln His Ser Glu Glu Ile Thr Thr Ala Asp Ile Arg
        195                 200                 205

```
Val Gln Leu Thr Glu His Val Ile Lys Lys Val Ile Pro Ser His Leu
    210                 215                 220

Leu Asp Glu Lys Thr Lys Tyr His Ile Gln Pro Ser Gly Lys Phe Ile
225                 230                 235                 240

Ile Gly Gly Ile Ala Gly Asp Ala Gly Leu Thr Gly Arg Lys Ile Ile
                245                 250                 255

Val Asp Thr Tyr Gly Gly Trp Gly Ala His Gly Gly Gly Ala Phe Ser
                260                 265                 270

Gly Lys Asp Phe Ser Lys Val Asp Arg Ser Ala Ala Tyr Ala Ala Arg
            275                 280                 285

Trp Val Ala Lys Ser Leu Val His Ala Lys Leu Ala Arg Arg Cys Leu
        290                 295                 300

Val Gln Phe Ser Tyr Ala Ile Gly Val Pro Glu Pro Leu Ser Ile Tyr
305                 310                 315                 320

Val Asp Thr Tyr Gly Thr Ser Thr Tyr Ser Ser Asp Glu Leu Val Lys
                325                 330                 335

Ile Ile Asn Lys Asn Phe Asp Leu Arg Pro Gly Val Ile Val Lys Glu
                340                 345                 350

Leu Asp Leu Ala Arg Pro Ile Tyr Phe Lys Thr Ala Ser Tyr Gly His
            355                 360                 365

Phe Thr Asn Gln Glu Asn Pro Trp Glu Gln Pro Lys Val Leu Lys Leu
370                 375                 380

<210> SEQ ID NO 12
<211> LENGTH: 384
<212> TYPE: PRT
<213> ORGANISM: Saccharomyces cerevisiae

<400> SEQUENCE: 12

Met Ser Lys Ser Lys Thr Phe Leu Phe Thr Ser Glu Ser Val Gly Glu
1               5                   10                  15

Gly His Pro Asp Lys Ile Cys Asp Gln Val Ser Asp Ala Ile Leu Asp
                20                  25                  30

Ala Cys Leu Glu Gln Asp Pro Phe Ser Lys Val Ala Cys Glu Thr Ala
            35                  40                  45

Ala Lys Thr Gly Met Ile Met Val Phe Gly Glu Ile Thr Thr Lys Ala
        50                  55                  60

Arg Leu Asp Tyr Gln Gln Ile Val Arg Asp Thr Ile Lys Lys Ile Gly
65                  70                  75                  80

Tyr Asp Asp Ser Ala Lys Gly Phe Asp Tyr Lys Thr Cys Asn Val Leu
                85                  90                  95

Val Ala Ile Glu Gln Gln Ser Pro Asp Ile Ala Gln Gly Leu His Tyr
            100                 105                 110

Glu Lys Ser Leu Glu Asp Leu Gly Ala Gly Asp Gln Gly Ile Met Phe
        115                 120                 125

Gly Tyr Ala Thr Asp Glu Thr Pro Glu Gly Leu Pro Leu Thr Ile Leu
    130                 135                 140

Leu Ala His Lys Leu Asn Met Ala Met Ala Asp Ala Arg Arg Asp Gly
145                 150                 155                 160

Ser Leu Pro Trp Leu Arg Pro Asp Thr Lys Thr Gln Val Thr Val Glu
                165                 170                 175

Tyr Glu Asp Asp Asn Gly Arg Trp Val Pro Lys Arg Ile Asp Thr Val
            180                 185                 190

Val Ile Ser Ala Gln His Ala Asp Glu Ile Ser Thr Ala Asp Leu Arg
```

```
            195                 200                 205
Thr Gln Leu Gln Lys Asp Ile Val Glu Lys Val Ile Pro Lys Asp Met
    210                 215                 220

Leu Asp Glu Asn Thr Lys Tyr Phe Ile Gln Pro Ser Gly Arg Phe Val
225                 230                 235                 240

Ile Gly Gly Pro Gln Gly Asp Ala Gly Leu Thr Gly Arg Lys Ile Ile
                245                 250                 255

Val Asp Ala Tyr Gly Gly Ala Ser Ser Val Gly Gly Ala Phe Ser
                260                 265                 270

Gly Lys Asp Tyr Ser Lys Val Asp Arg Ser Ala Ala Tyr Ala Ala Arg
                275                 280                 285

Trp Val Ala Lys Ser Leu Val Ala Ala Gly Leu Cys Lys Arg Val Gln
            290                 295                 300

Val Gln Phe Ser Tyr Ala Ile Gly Ile Ala Glu Pro Leu Ser Leu His
305                 310                 315                 320

Val Asp Thr Tyr Gly Thr Ala Thr Lys Ser Asp Asp Glu Ile Ile Glu
                325                 330                 335

Ile Ile Lys Lys Asn Phe Asp Leu Arg Pro Gly Val Leu Val Lys Glu
                340                 345                 350

Leu Asp Leu Ala Arg Pro Ile Tyr Leu Pro Thr Ala Ser Tyr Gly His
                355                 360                 365

Phe Thr Asn Gln Glu Tyr Ser Trp Glu Lys Pro Lys Lys Leu Glu Phe
370                 375                 380
```

<210> SEQ ID NO 13
<211> LENGTH: 382
<212> TYPE: PRT
<213> ORGANISM: Saccharomyces cerevisiae

<400> SEQUENCE: 13

```
Met Ala Gly Thr Phe Leu Phe Thr Ser Glu Ser Val Gly Glu Gly His
1               5                   10                  15

Pro Asp Lys Ile Cys Asp Gln Val Ser Asp Ala Ile Leu Asp Ala Cys
                20                  25                  30

Leu Ala Glu Asp Pro His Ser Lys Val Ala Cys Glu Thr Ala Ala Lys
            35                  40                  45

Thr Gly Met Ile Met Val Phe Gly Glu Ile Thr Thr Lys Ala Gln Leu
        50                  55                  60

Asp Tyr Gln Lys Ile Val Arg Asp Thr Ile Lys Lys Ile Gly Tyr Asp
65              70                  75                  80

Asp Ser Ala Lys Gly Phe Asp Tyr Lys Thr Cys Asn Val Leu Val Ala
                85                  90                  95

Ile Glu Gln Gln Ser Pro Asp Ile Ala Gln Gly Val His Glu Glu Lys
            100                 105                 110

Asp Leu Glu Asp Ile Gly Ala Gly Asp Gln Gly Ile Met Phe Gly Tyr
        115                 120                 125

Ala Thr Asp Glu Thr Pro Glu Gly Leu Pro Leu Thr Ile Leu Leu Ala
    130                 135                 140

His Lys Leu Asn Met Ala Met Ala Asp Ala Arg Arg Asp Gly Ser Leu
145                 150                 155                 160

Ala Trp Leu Arg Pro Asp Thr Lys Thr Gln Val Thr Val Glu Tyr Lys
                165                 170                 175

Asp Asp His Gly Arg Trp Val Pro Gln Arg Ile Asp Thr Val Val Val
            180                 185                 190
```

-continued

```
Ser Ala Gln His Ala Asp Glu Ile Thr Thr Glu Asp Leu Arg Ala Gln
            195                 200                 205
Leu Lys Ser Glu Ile Ile Glu Lys Val Ile Pro Arg Asp Met Leu Asp
        210                 215                 220
Glu Asn Thr Lys Tyr Phe Ile Gln Pro Ser Gly Arg Phe Val Ile Gly
225                     230                 235                 240
Gly Pro Gln Gly Asp Ala Gly Leu Thr Gly Arg Lys Ile Ile Val Asp
                245                 250                 255
Ala Tyr Gly Gly Ala Ser Ser Val Gly Gly Gly Ala Phe Ser Gly Lys
            260                 265                 270
Asp Tyr Ser Lys Val Asp Arg Ser Ala Ala Tyr Ala Ala Arg Trp Val
        275                 280                 285
Ala Lys Ser Leu Val Ala Ala Gly Leu Cys Lys Arg Val Gln Val Gln
        290                 295                 300
Phe Ser Tyr Ala Ile Gly Ile Ala Glu Pro Leu Ser Leu His Val Asp
305                     310                 315                 320
Thr Tyr Gly Thr Ala Thr Lys Ser Asp Glu Glu Ile Ile Asp Ile Ile
                325                 330                 335
Ser Lys Asn Phe Asp Leu Arg Pro Gly Val Leu Val Lys Glu Leu Asp
            340                 345                 350
Leu Ala Arg Pro Ile Tyr Leu Pro Thr Ala Ser Tyr Gly His Phe Thr
        355                 360                 365
Asn Gln Glu Tyr Pro Trp Glu Lys Pro Lys Thr Leu Lys Phe
        370                 375                 380
```